US012336781B2

(12) United States Patent
Zabinski et al.

(10) Patent No.: US 12,336,781 B2
(45) Date of Patent: Jun. 24, 2025

(54) DEVICES, SYSTEMS, AND METHODS FOR MAINTAINING A STERILE SURGICAL FIELD

(71) Applicant: INTUITIVE SURGICAL OPERATIONS, INC., Sunnyvale, CA (US)

(72) Inventors: John W. Zabinski, Fremont, CA (US); Russell Blanchard, San Jose, CA (US); Humphrey W. Chow, Cupertino, CA (US); Gary Ettinger, Cupertino, CA (US); Sarah Galvis, Pleasanton, CA (US); Stefan Geiger, Union City, CA (US); Craig Gotsill, San Francisco, CA (US); Amy Kerdok, San Jose, CA (US); Justin Krom, Southington, CT (US); Daryl Oshatz, Mountain View, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 737 days.

(21) Appl. No.: 17/435,100

(22) PCT Filed: Mar. 5, 2020

(86) PCT No.: PCT/US2020/021139
§ 371 (c)(1),
(2) Date: Aug. 31, 2021

(87) PCT Pub. No.: WO2020/181063
PCT Pub. Date: Sep. 10, 2020

(65) Prior Publication Data
US 2022/0125542 A1    Apr. 28, 2022

Related U.S. Application Data
(60) Provisional application No. 62/813,973, filed on Mar. 5, 2019.

(51) Int. Cl.
*A61B 46/10*    (2016.01)
*A61B 50/13*    (2016.01)
(Continued)

(52) U.S. Cl.
CPC .............. *A61B 46/10* (2016.02); *A61B 50/13* (2016.02); *A61B 50/20* (2016.02); *A61B 50/33* (2016.02)

(58) Field of Classification Search
CPC ......... A61B 46/10; A61B 50/13; A61B 50/20; A61B 50/33; A61B 90/50
(Continued)

(56) References Cited

U.S. PATENT DOCUMENTS

| 5,170,804 A | 12/1992 | Glassman |
| 5,373,116 A | 12/1994 | Schneider |

(Continued)

FOREIGN PATENT DOCUMENTS

JP    H1149305 A    2/1999

OTHER PUBLICATIONS

International Search Report and Written Opinion for Application No. PCT/US2020/021139, mailed Sep. 1, 2020, 17 pages.

(Continued)

*Primary Examiner* — Joseph M Dietrich
*Assistant Examiner* — Michael T. Holtzclaw
(74) *Attorney, Agent, or Firm* — Jones Robb, PLLC

(57) ABSTRACT

A sterile drape assembly may comprise a drape and a cable guide coupled or configured to be coupled to the drape. The drape may comprise a first portion configured to cover a medical device holder and a second portion configured to cover a portion of an arm that supports the medical device holder. The cable guide may comprise two opposing guide-post arms extending in a first direction and defining a first opening and a side arm extending laterally from one of the (Continued)

guidepost arms, the side arm defining a second opening. The first opening is configured to receive and route a first transmission line along a first path. The second opening is spaced from the first opening and is configured to receive and route a second transmission line along a second path spaced from the first path.

19 Claims, 44 Drawing Sheets

(51) Int. Cl.
*A61B 50/20* (2016.01)
*A61B 50/33* (2016.01)

(58) Field of Classification Search
USPC .............................................. 606/1; 128/849
See application file for complete search history.

(56) References Cited

U.S. PATENT DOCUMENTS

| | | |
|---|---|---|
| 5,383,476 A | 1/1995 | Peimer et al. |
| 10,213,267 B2 * | 2/2019 | King ................. A61B 46/10 |
| 2004/0176797 A1 * | 9/2004 | Opolski ........... A61B 17/12022 |
| | | 606/213 |
| 2007/0157438 A1 * | 7/2007 | Judd ..................... H02G 11/02 |
| | | 24/115 R |
| 2008/0067302 A1 | 3/2008 | Olivera et al. |
| 2008/0250983 A1 | 10/2008 | Sundarrao |
| 2011/0083983 A1 * | 4/2011 | Walters ................. A61B 50/20 |
| | | 206/370 |
| 2011/0180436 A1 | 7/2011 | Von Posern et al. |
| 2012/0199704 A1 * | 8/2012 | Taylor .................... F16G 11/00 |
| | | 248/315 |
| 2014/0014117 A1 * | 1/2014 | Weinberg ............... A61B 46/23 |
| | | 128/849 |
| 2014/0353189 A1 * | 12/2014 | Lotosky-Compton ...................... |
| | | A61B 46/23 |
| | | 206/370 |
| 2018/0036091 A1 * | 2/2018 | Scholan ................. A61B 46/10 |
| 2018/0228564 A1 * | 8/2018 | Recanati ................ F16L 3/1075 |
| 2019/0099232 A1 * | 4/2019 | Soto ........................ A61B 90/39 |

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

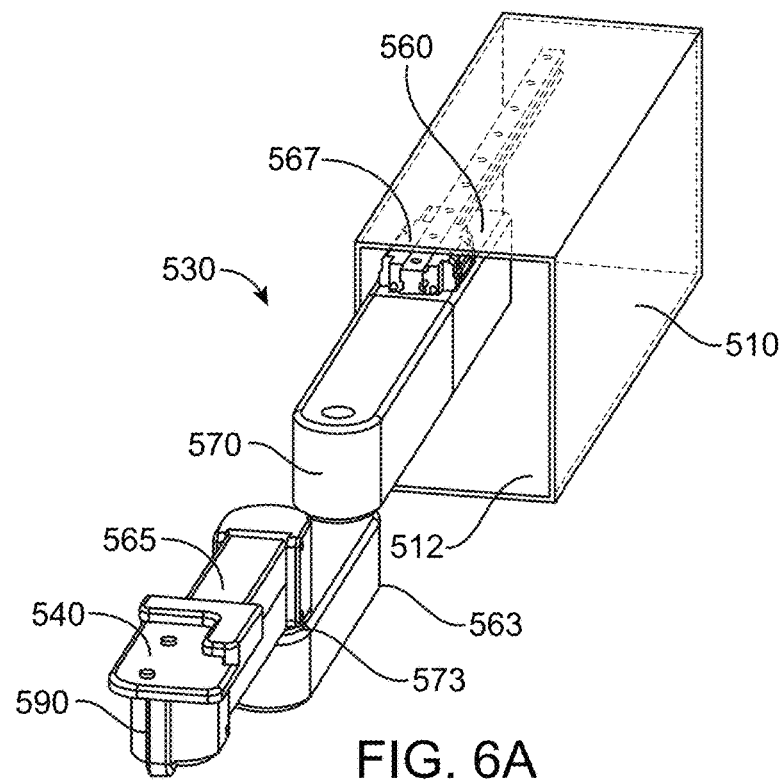
FIG. 6A
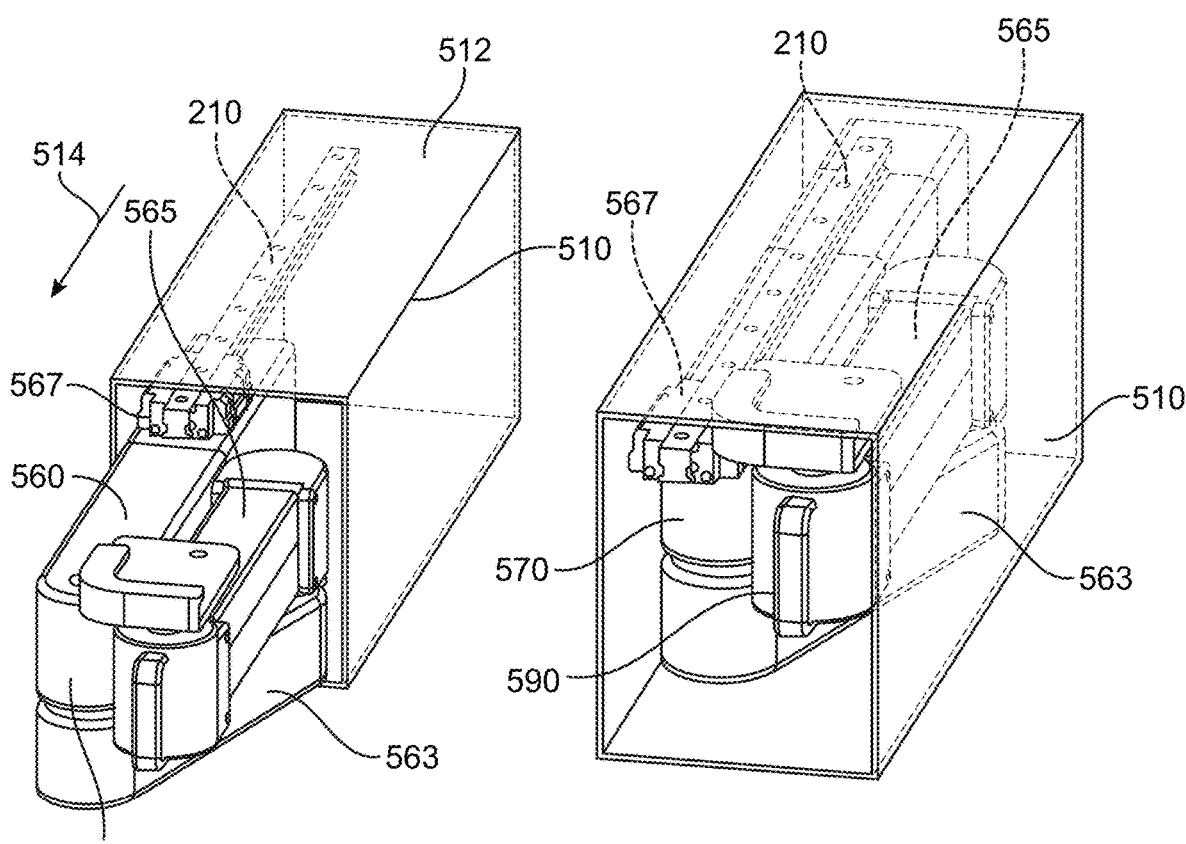
FIG. 6B
FIG. 6C

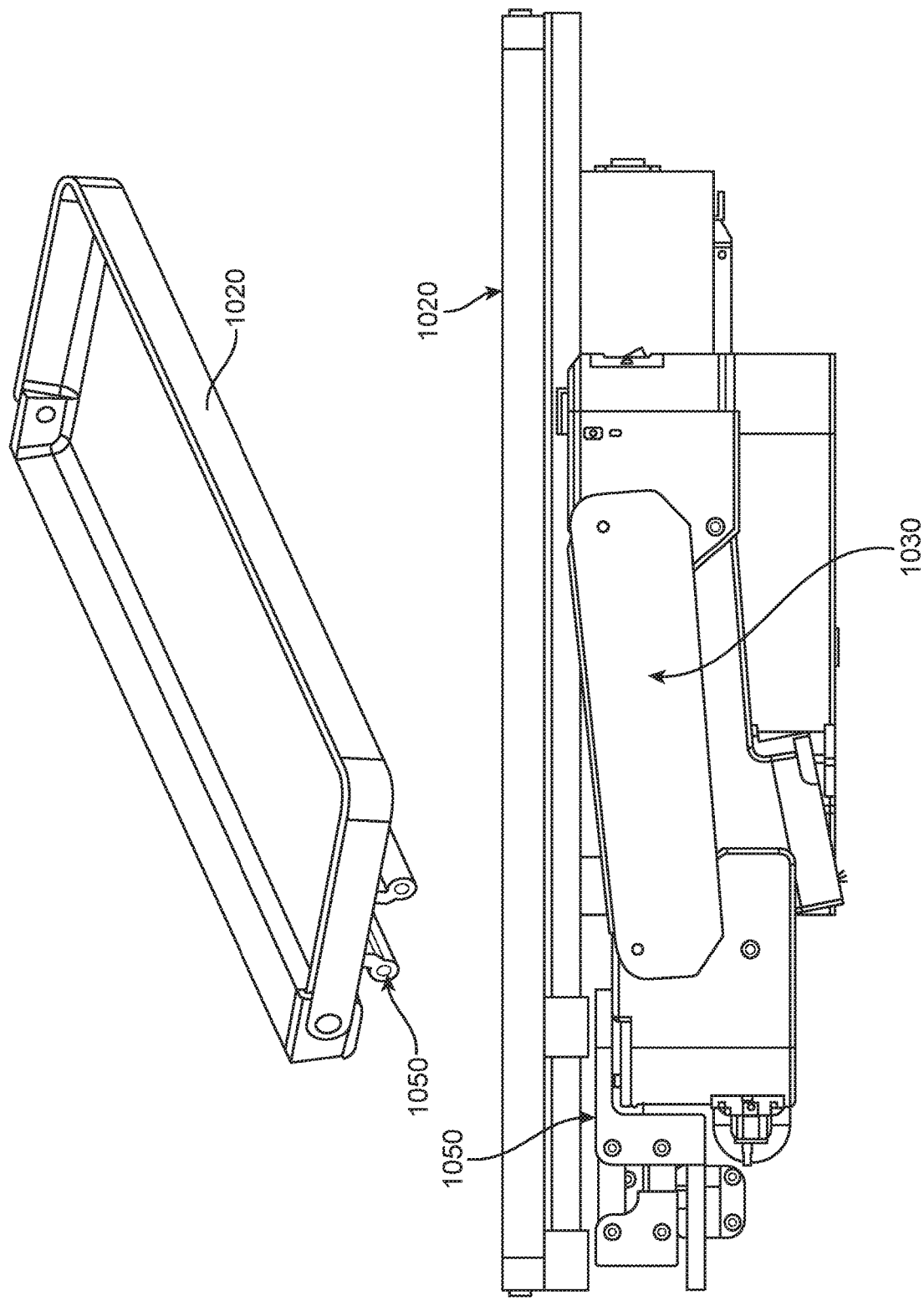

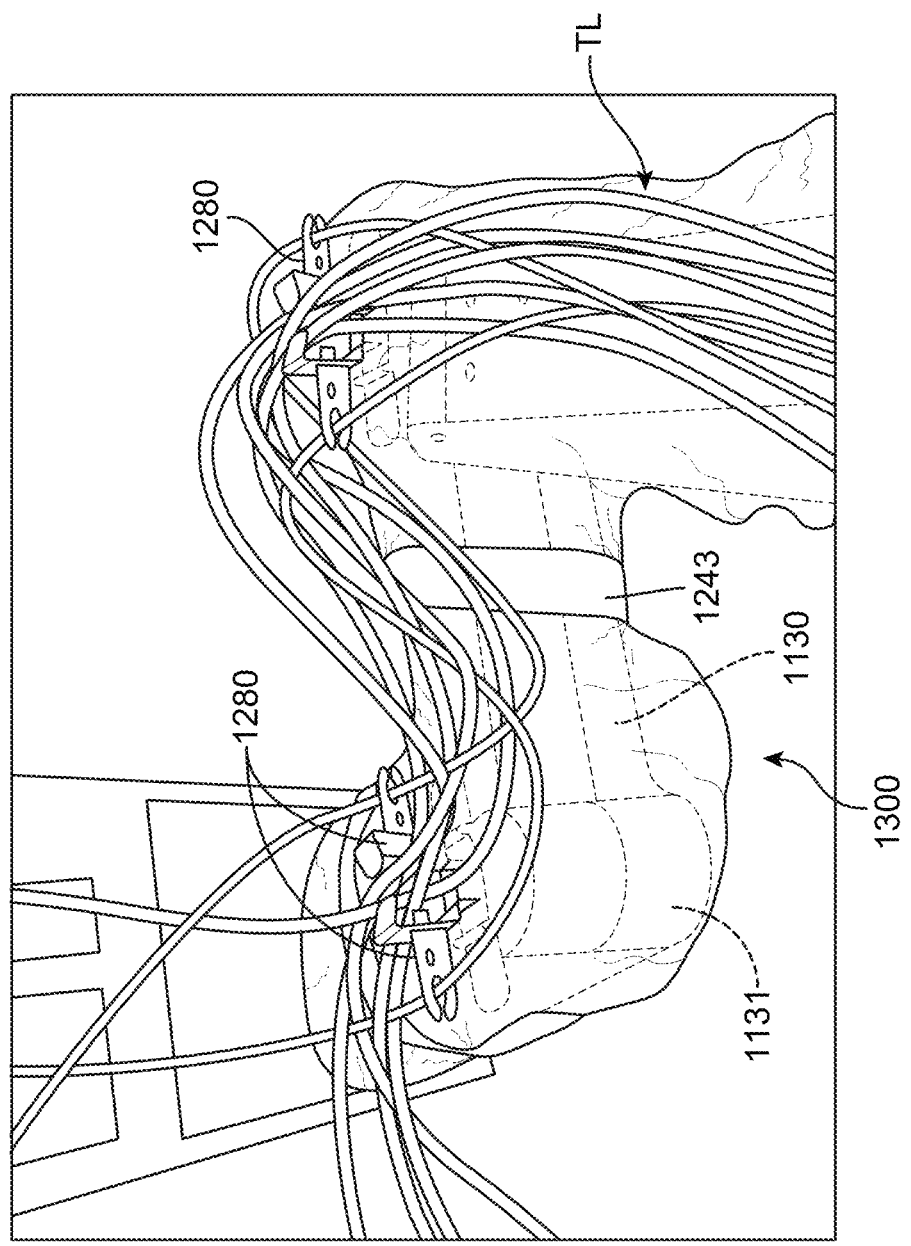

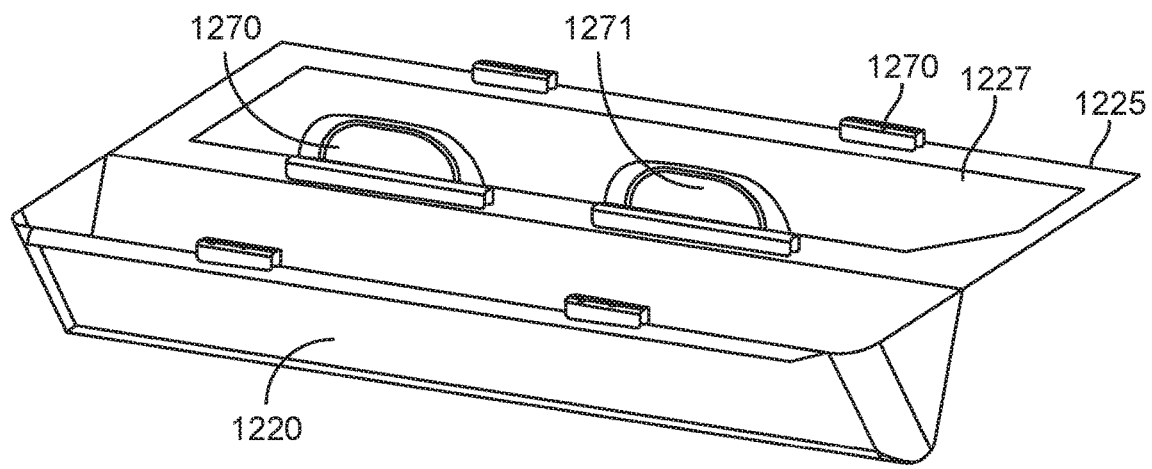
FIG. 12A
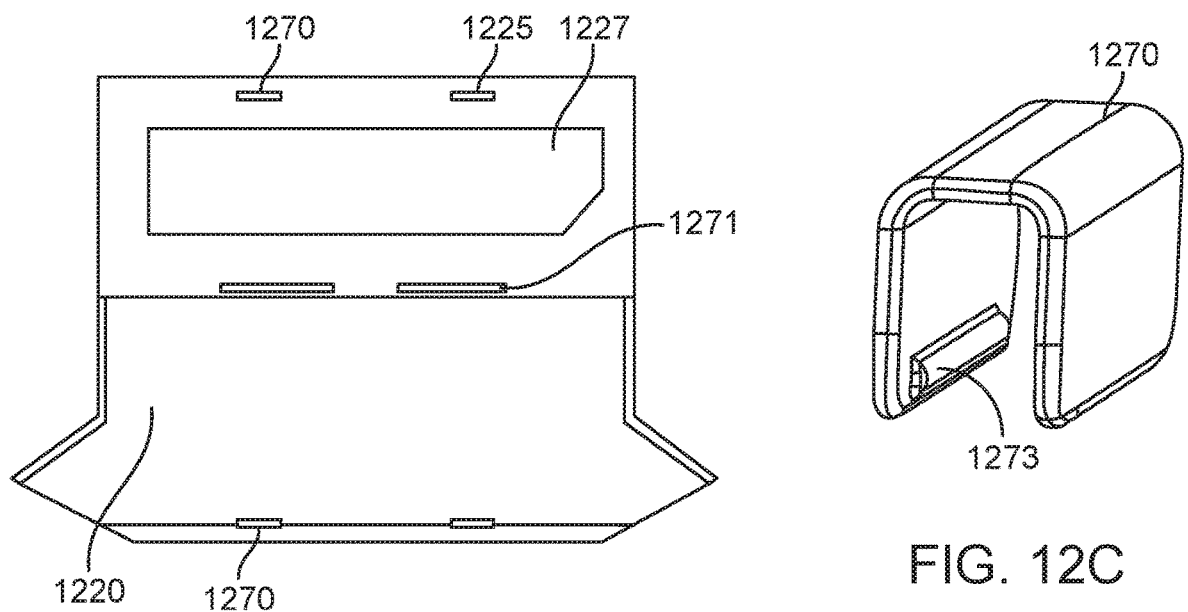
FIG. 12B
FIG. 12C

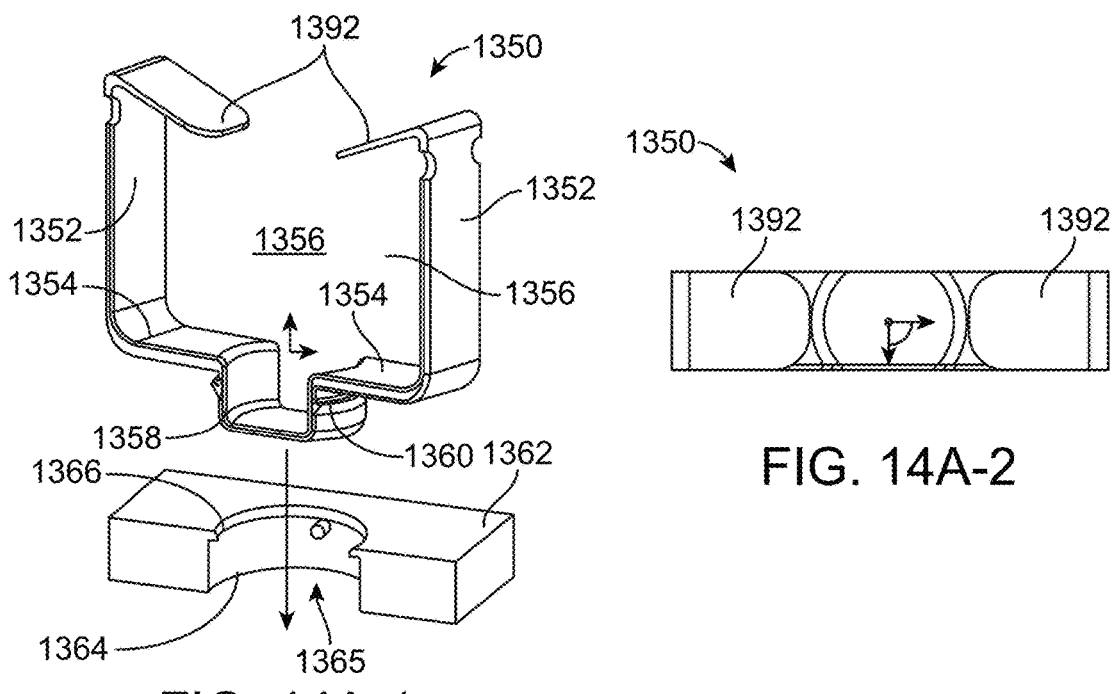
FIG. 14A-1
FIG. 14A-2
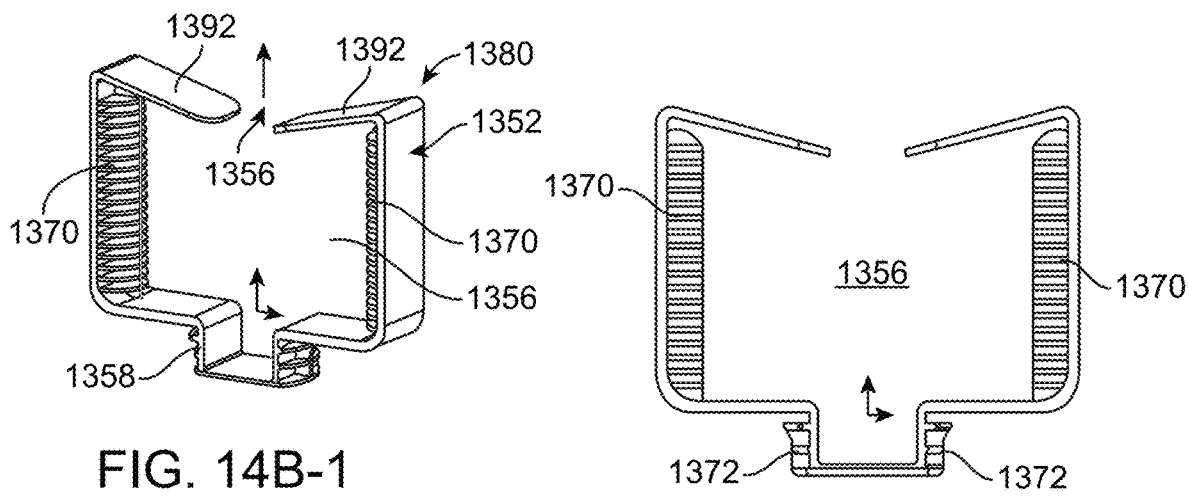
FIG. 14B-1
FIG. 14B-3
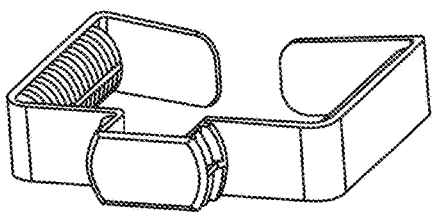
FIG. 14B-2

DEVICES, SYSTEMS, AND METHODS FOR MAINTAINING A STERILE SURGICAL FIELD

This application is a U.S. national stage application under 35 U.S.C. § 371(c) of International Application No. PCT/US2020/021139, filed Mar. 5, 2020, which claims priority to and the benefit of the filing date of U.S. Provisional Patent Application 62/813,973, entitled "DEVICES, SYSTEMS, AND METHODS FOR MAINTAINING A STERILE SURGICAL FIELD," filed Mar. 5, 2019, the entire contents of each of which are incorporated by reference herein in its entirety.

TECHNICAL FIELD

Aspects of the present disclosure relate to devices, systems, and methods for maintaining sterility of a surgical field while utilizing various instruments and devices that may be nonsterile or make contact with equipment in a nonsterile field.

INTRODUCTION

Minimally invasive surgery seeks to minimize patient trauma by introducing therapeutic, diagnostic, and imaging instruments through small incisions or natural orifices. One group of such instruments are manually operated. Another group of such instruments are teleoperated by using a computer-assisted surgical system (a telesurgical system), in which a surgeon operates an input control unit to remotely control one or more instruments operated by a manipulator unit to which the one or more instruments are coupled.

Whether operated manually or via a telesurgical system, many instruments are coupled to auxiliary equipment that support the instruments' clinical purpose. For example, electrosurgical instruments are coupled to electrosurgical generator units (ESUs) that provide mono- and bipolar energy to the instrument as required. In addition, other auxiliary equipment and associated medical devices may be used to support a surgical procedure. For example, suction/irrigation devices that may be used during various surgeries require operable coupling to corresponding irrigation fluid and vacuum sources. Similarly, endoscope instruments and other imaging devices require supporting imaging and illumination equipment. Thus, various auxiliary function equipment is typically used during minimally invasive surgery to support medical devices used at a remote surgical site in performing functions such as insufflation supply, cautery smoke evacuation, ultrasonic energy generation, etc. As used herein, medical devices include both instruments used for manipulating tissue and sensing an environment (e.g., imaging, pressure, oxygen etc.) at a remote surgical site, as well as devices used to supply suction, irrigation, light, and other types of flux proximate a remote surgical site.

As a result of the many auxiliary function units that are used to support modern surgery, and the various connections (e.g., via transmission lines) between the auxiliary function equipment and the corresponding medical devices, the operating room becomes a complex and crowded environment during surgery. For example, maintaining a sterile field around a patient during surgery can pose challenges. In particular, it can be challenging to maintain sterility in applications that involve use of a variety of medical devices to perform a surgical procedure that may come into and out of use and/or require connection via transmission lines (e.g., electrical and/or data cables) to equipment that is typically not sterile and is maintained outside of the sterile field. For example, in various surgical applications, including various minimally-invasive surgical applications, medical devices, such as electrosurgical instruments, insufflation/evacuation tubing, imaging instruments, and the like are connected to auxiliary function equipment that supply and control the operation of those medical devices. Such auxiliary function equipment may be in a portion of the operating theatre that is not part of the sterile surgical field, and is therefore generally not sterilized. Providing robust and continued connection of medical devices in the sterile field to such equipment outside the sterile field is thus needed to ensure surgical procedures can occur efficiently and sterile conditions maintained.

A need exists to facilitate connection of the various medical devices that are used during a surgical procedure and are in the sterile field to equipment outside the sterile field without risking a breach of the sterile field or medical devices used in the sterile field. Further, a need exists to provide a convenient and accessible place to hold surgical instruments and other medical devices while not in use, but that maintains their sterility. In addition, a need exists to provide medical devices with a relatively large reach into, and range of movement within, the sterile field while still allowing them to be connected via transmission lines to equipment outside of the sterile field. A need also exists to manage transmission lines during surgical procedures that may have multiple instruments and multiple transmission lines running from the sterile field to auxiliary equipment outside the sterile field.

SUMMARY

Exemplary embodiments of the present disclosure may demonstrate one or more of the above-mentioned desirable features. Other features and/or advantages may become apparent from the description that follows.

Various embodiments include a sterile drape assembly comprising a drape and a cable guide coupled or configured to be coupled to the drape. The drape may comprise a first portion configured to be cover a medical device holder and a second portion configured to cover a portion of an arm that supports the medical device holder. The cable guide may comprise two opposing guidepost arms extending in a first direction and defining a first opening configured to receive and route a first transmission line along a first path. The cable guide may also comprise a side arm extending laterally from one of the guidepost arms, the side arm defining a second opening spaced from the first opening and is configured to receive and route a second transmission line along a second path spaced from the first path.

Various embodiments also include a method comprising arranging a drape over an am supporting a medical device holder and attaching a cable guide to the arm by inserting a base portion of the cable guide into a complementary receptacle in the arm such that a portion of the cable guide is on a first side of the drape and the receptacle is on a second side of the drape opposite the first side of the drape.

Various embodiments also include a medical system, comprising an arm, a medical device holder coupled or mountable to the arm, a drape configured to cover the medical device holder and at least a portion of the arm in a coupled or mounted state of the medical device holder to the arm, and a cable guide. The cable guide may comprise a base portion coupled or configured to be coupled to a complementary receptacle of the arm. The cable guide may further comprise two opposing guidepost arms extending from the base portion and defining an opening configured to receive and route a transmission line. In a coupled state of the base portion to the receptacle, the guidepost arms are positioned on a first side of the drape and the arm is positioned on a second side of the drape, with the first side being opposite from the second side.

For a fuller understanding of the nature and advantages of the present teachings, reference is made to the following description and drawings. Other aspects, objects, and advantages of the present teachings will be apparent from the drawings and detailed description that follows.

BRIEF DESCRIPTION OF THE DRAWINGS

The present disclosure can be understood from the following detailed description, either alone or together with the accompanying drawings. The drawings are included to provide a further understanding of the present disclosure, and are incorporated in and constitute a part of this specification. The drawings illustrate one or more exemplary embodiments of the present teachings and together with the description serve to explain certain principles and operation.

FIGS. 2A-1 to 2J show several views of various exemplary embodiments of medical device holders in accordance with the present disclosure.

FIGS. 3A-1 to 4 show several views of various exemplary embodiments of medical device holder accessories in accordance with the present disclosure.

FIGS. 6A-6C show perspective views of extended, partially extended, and retracted configurations of an exemplary embodiment of an arm relative to a base in accordance with the present disclosure.

FIGS. 10A-1 and 10A-2 show partial cut-away, perspective views of an exemplary embodiment of arm and subcomponents thereof in accordance with the present disclosure.

FIG. 10A-3 shows a side elevational view of an exemplary embodiment of the arm of FIGS. 10A-1 and 10A-2.

FIGS. 10B-1 and 10B-2 show views of an exemplary embodiment of an arm with another embodiment of a medical device holder in accordance with the present disclosure.

FIG. 10B-3 shows a schematic illustration of another exemplary embodiment of a medical device holder in accordance with the present disclosure.

FIGS. 11E and 11F show further views of exemplary embodiments of arms, drapes, and medical device holders in accordance with the present disclosure.

FIGS. 12A and 12B show perspective and plan views, respectively, of an exemplary embodiment of a combined drape and medical device holder in accordance with the present disclosure.

FIG. 12C shows a perspective new of an exemplary embodiment of a clip for retaining the drape of FIGS. 12A and 12B.

FIGS. 14A-1 and 14A-2 show exploded, perspective and top views, respectively, of an exemplary embodiment of a cable guide in accordance with the present disclosure.

FIGS. 14B-1 to 14B-3 show exploded and perspective views of another exemplary embodiment of a cable guide in accordance with the present disclosure.

DETAILED DESCRIPTION

Figure 1:
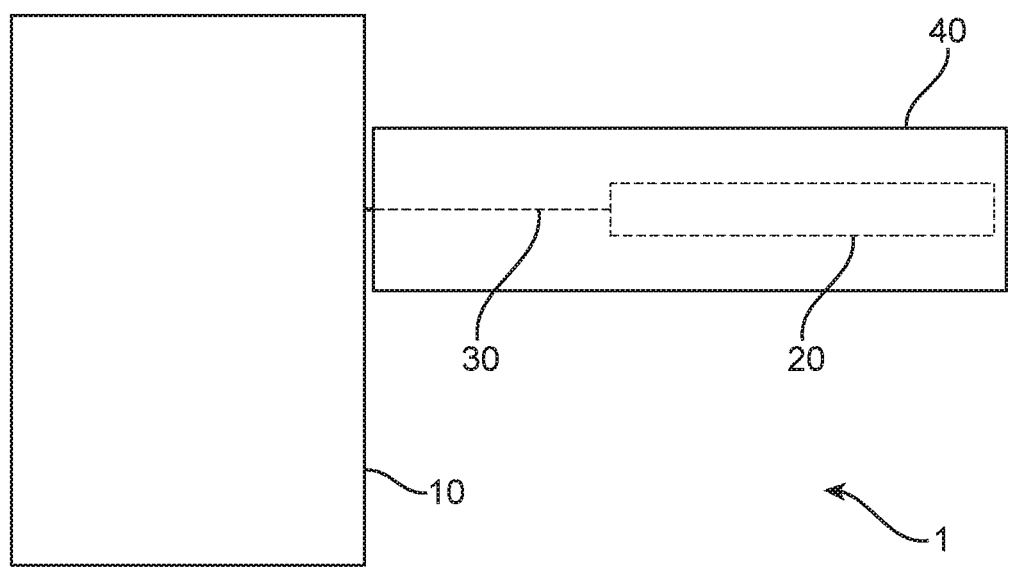
FIG. 1 shows a schematic illustration of a system as described herein.

The various disclosed embodiments include a medical device holder configured to securely hold one or more medical instruments. Thus, the various exemplary embodiments of medical device holders disclosed herein may prevent or reduce a risk of medical instruments rolling or otherwise falling off the holder. In this manner, damage to and potential reduction in the lifespan of medical instruments, which may be vulnerable devices with delicate components that can become damaged if they fall a holder, can be decreased. Additionally, various disclosed embodiments of medical device holders allow the holder to be easily moved in different positions and locations during a medical procedure. This can provide a more efficient workflow system, allowing users to easily move the holder in different positions depending on the specific procedure being performed at any given time frame during the medical procedure.

Various embodiments discussed herein also provide instrument and cable organization, thus also contributing to a more efficient workflow system. For example, embodiments of a medical device holder can include mechanisms to organize the instruments and cables so that a user may easily know the location of each instrument before reaching for the instrument, thus improving the user's efficiency during the medical procedure. Additionally, such organization features may route cables on the medical device holder so that they do not interfere with the tips of the medical instruments when disposed on the holder. Furthermore, the cable organization and routing structures in accordance with various exemplary embodiments can separate monopolar and bipolar cables in order to prevent capacitive coupling between such cables.

Various disclosed embodiments also provide a medical device holder that may be sterilizable and/or covered with a sterilized drape.

Various disclosed embodiments of the medical device holder may include one or more components that assist with organization, access to, and maintaining sterility of various medical devices that may be used during a surgical procedure. Additionally, a medical device holder has a sufficient length to receive a shaft and back end housing mechanisms of various sized surgical instruments designed for use with telesurgical systems. The medical device holder may also have a width sufficient to hold two or more such surgical instruments. Medical device holders in accordance with various embodiments of the disclosure also can facilitate ease of swapping out medical devices, such as imaging instruments, during a surgical procedure by providing a support area large enough to easily and safely hold two or more medical devices at the same time.

Various disclosed embodiments according to the present disclosure include an arm configured for attachment to a base, one or more medical device holders, a monitor, etc. Such an arm may be an arm having a single link or an arm having multiple kinematic links. Additionally, the disclosed arm may be movable (both horizontally and vertically) and pivotable relative to the structure to which the arm is attached. Various disclosed embodiments provide an arm that facilitates an efficient workflow system by allowing the arm to be moved into multiple positions relative to the structure to which the arm is attached. Similarly, the arm-medical device holder connection can permit a variety of orientations of the medical device holder relative to the arm and thus within the operating theatre. In various embodiments, the arm and medical device holder can provide a wide reach and range of positions within the surgical sterile field while still allowing medical devices to remain connected to equipment outside the sterile field, with a minimal risk of a breach in the sterile field due to unintended contact with the non-sterile field.

An arm, in the various exemplary embodiments discussed herein, allows sterilized medical devices to be staged prior to surgery. For example, the arm may be attached to the medical device holder, and the medical devices may be disposed on the medical device holder such that their transmission lines are neatly routed along the arm, which can be provided with a sterile drape, before the medical procedure. Clips and/or posts on the arm help to organize and route the cables along the arm, allowing convenient and easy access for personnel outside the sterile field to access connectors on transmission lines to connect them with auxiliary function equipment outside the sterile field.

Various disclosed embodiments also include an arm that can assume different lengths. For example, in some embodiments the arm may be foldable and retractable in order to assume the different lengths. Such may also contribute to the efficient workflow system by allowing a user to easily move the arm (and thus the medical instruments disposed on the holder) to various positions during the course of a medical procedure. For example, the arm may move from a first position disposed over a patient to a second position remote from the patient but still within the sterile field. Moreover, the ability to fold or move from an extended length to a retracted length can provide for convenient stowage of the arm when not in use.

Various disclosed embodiments also include a drape configured to provide a sterile environment during a surgical procedure. The drape has a size and shape tailored for the structure over which the drape is disposed. The various embodiments include drapes comprising different materials in order to optimize the use of each portion of the drape. For example, a portion of the drape, which receives a medical instrument, may include an absorbable material.

A drape, according to the various embodiments discussed herein, include one or more troughs for storage of medical instruments, cables, etc., which may help to provide a more efficient workflow system by allowing the medical instruments, their transmission lines, and other devices that may be used during a surgical procedure to be neatly organized. Additionally, medical instruments may be conveniently and ergonomically stored during the medical procedure so that a user may easily access the instruments during the procedure.

Various disclosed embodiments also include surgical drapes comprising various transmission line routing features that can be positioned to extend along a length of draped parts to provide organization and routing of transmission lines from medical instruments on the medical device holder back to equipment outside the sterile field. Keeping such transmission lines routed and organized reduces personnel accidentally snagging or tripping on the transmission lines, which can cause damage to medical devices and/or personnel. It also reduces the risk of mixing up transmission lines associated with different medical devices. In addition, such routing features can allow for appropriate slack to be let in and out of transmission lines as a medical device holder that holds the medical devices is moved throughout the sterile field, which can in turn ensure medical device transmission lines remain connected to auxiliary equipment and the medical devices remain held on the medical device holder regardless of movement and repositioning of the medical device holder, including by virtue of repositioning of an arm to which the medical device holder is attached.

Various disclosed embodiments also include a base that may have a variety of forms and be configured to store and house the arm and/or medical device holder. Such a base can include a storage compartment sized to receive the arm with or without a medical device holder attached. In various exemplary embodiments, the base can be wheeled for easy transport to, from, and with an operating room. Further, in an exemplary embodiment, the base is an auxiliary system that holds one or more auxiliary function supply equipment that provides auxiliary functionality to medical devices used during a surgical procedure.

With reference to FIG. 1, a system 1 for holding medical equipment in accordance with various exemplary embodiments is depicted schematically. The system 1 includes a base 10 to which a medical device holder 20 is attached through a mechanical arm 30. The medical device holder 20 may comprise a tray, for example. In some embodiments, medical device holder 20 is connected to base 10 through arm 30. In some embodiments, the arm 30 and/or medical device holder 20 may be removably coupled to the base 10. Similarly, the medical device holder 20 may be removably coupled to the arm 30. In some embodiments, the system 1 may further include a sterile drape 40 that is disposed over medical device holder 20 and/or arm 30 (both shown in FIG. 1) to provide a sterile barrier. In some embodiments, the system 1 may include a sterile drape 40 can be a flat sheet that is disposed around medical device holder 20 and/or arm 30 to provide a sterile barrier, that is, the sterile drape 40 has a size and a shape so that it envelopes and surrounds the medical device holder 20 and/or arm 30 on some or all of its/their sides. In other embodiments, the sterile drape 40 may be configured as an enclosed sleeve-like object to receive the arm 30 and/or medical device holder 20. Various exemplary embodiments of drapes, which may be used as the sterile drape 40, are discussed further below.

Base 10 may be a cart and/or an auxiliary system that includes various auxiliary function equipment, such as for image processing, electrocautery energy generation, system central processing, and/or insufflation/evacuation. In other embodiments, base 10 may be any cart or stationary base for attachment to medical device holder 20 and arm 30. For example, the various embodiments of the medical device holder 20 and arm 30 can be provided as part of a moveable stand, similar to a Mayo stand. Alternatively, the arm 30 and medical device holder 20 may be configured to be coupled to other components of an operating theatre, such as a patient bed or a manipulator system in a telesurgical system.

As discussed further below, in an exemplary embodiment, medical device holder 20 and arm 30 may be housed in a base 10 when not in use, which may be convenient to move the base 10, and consequently the holder 20 and arm 30, out of the way when not in use. In preparation for a surgical procedure, medical device holder 20 and arm 30 may be removed from a storage position within the base 10 such that medical device holder 20 is placed in proximity, including over, a patient's bed. Drape 40 may also be disposed over medical device holder 20 and arm 30 in order to provide a sterile environment. One or more medical devices, such as imaging instruments (e.g., endoscopes), surgical instruments, and/or insufflation/evacuation tubing, may be disposed over sterile drape 40 and supported by medical device holder 20. Medical device holder 20, arm 30, and base 10 may allow a surgeon to easily access the medical devices held by medical device holder 20 during the surgical procedure.

The system 1 may further include a variety of features that provide for efficient management and connection of transmission lines that connect the various medical devices held by the medical device holder 20 to equipment that is not within the sterile field, such as for example to equipment that may be part of or positioned at the base 10 when the base 10 is not part of the sterile field.

Medical Device Holder

Medical device holder 20 is configured to hold a variety of medical instruments and with their transmission lines attached during, for example, a medical procedure. Various exemplary embodiments of a medical device holder according to the present disclosure enable secure holding of medical devices, for example in the sterile field, when not in use, such as prior to the surgical procedure when setup is occurring or during the surgical procedure when medical equipment is not actively in use. Thus, medical device holder 20 may prevent the medical instruments from rolling off or falling off medical device holder 20. A length of medical device holder 20 may be sufficient to receive a shaft and back end housing mechanisms of various sized surgical instruments, including endoscopes, configured for use in telesurgical systems. A width of medical device holder 20 may be sufficient to hold two or more such instruments. In one embodiment, medical device holder 20 may have dimensions of 15 inches (38.1 cm)×30 inches (76.2 cm) for the overall lateral dimensions surrounding the face intended to hold the instruments. In other embodiments, medical device holder 20 may have a width ranging from 15 inches (38.1 cm) to 25 inches (63.5 cm) (inclusive); a length ranging from 20 inches (50.8 cm) to 30 inches (76.2 cm) (inclusive), and a thickness of up to three inches (7.6 cm) (inclusive).

Figures 1, 2A:
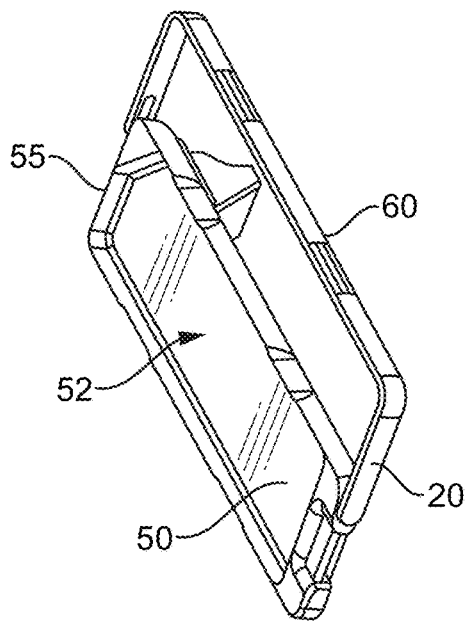

With reference to FIG. 2A-1, an embodiment of a medical device holder 20 includes a tray 50 and a support frame 60. Tray 50 includes a generally flat surface 52 with an upwardly protruding lip 55 around its outer perimeter. Thus, tray 50 may provide a flat working surface, while protruding lip 55 provides a barrier that prevents and/or minimizes the risk of instruments disposed on tray 50 from rolling off or falling off. In some embodiments, protruding lip 55 may be wide enough to include one or more recesses configured to hold a variety of objects such as, for example, clips, specimen containers, or transmission lines (not shown in FIG. 2A-1). In other exemplary embodiments, the tray 50 may have various surface features, such as recesses etc. that provide areas to hold items, such as sutures, scissors, etc. and/or portions of medical devices themselves. Various other embodiments of medical device holders with similar type tray structures having receptacles and other surface features are described further below. In some embodiments, the lip 55 may extend upwardly from the flat surface 52 up to three inches. It may be desirable to choose a height of the lip that accomplishes the desired outcome of preventing medical devices from rolling or falling off the tray while not posing an impediment from personnel removing the devices from the tray 50.

Figures 2, 2A:
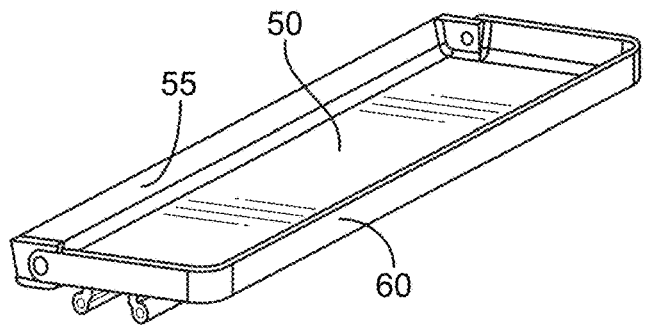
Figures 2, 2A, 3:
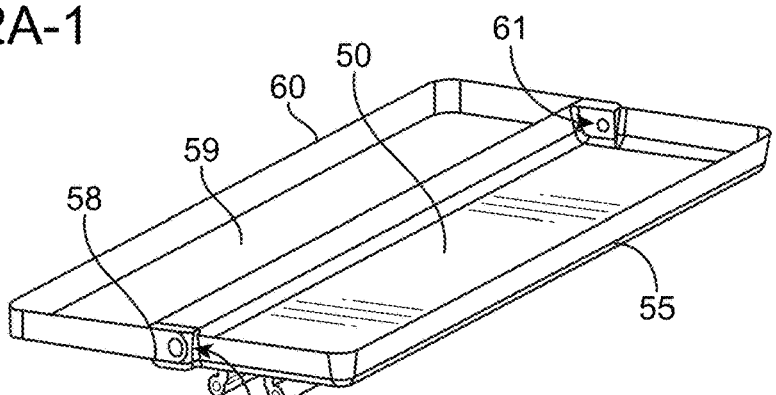

Support frame 60 may be pivotably attached to tray 50, e.g., at pivot couplings 61, 62 shown in FIG. 2A-3, such that support frame 60 rotates relative to tray 50, allowing support frame 60 to fold over tray 50 (FIG. 2A) or extend outwardly from tray 50 (FIGS. 2A-1, 2A-3). The tray 50 further includes one or more stops 58 (only one is illustrated in FIG. 2A-2) which permit the support frame 60 to rotate relative to the tray 50, but limit the range of rotational motion of the frame 60 relative to the tray 50. In some embodiments, the stops 58 may be oriented so that the frame 60 cannot rotate past a horizontal position (e.g., past 180 degrees from the folded position), as illustrated in FIGS. 2A-2, 2A-3, that is, the support frame 60 and the tray 50 are in the same or parallel planes. In some embodiments, as illustrated best in FIG. 2A-3, support frame 60 may be of the same height as protruding lip 55 so as to provide a uniform height of the medical device holder whether in the folded or open, extended configuration. In the folded configuration shown in FIG. 2A-2, support frame 60 and protruding lip 55 may be in a nesting relationship such that support frame 60 surrounds protruding lip 55. FIG. 2A-2 shows support frame 60 as being disposed on the outside of protruding lip 55 in the folded configuration. It is also contemplated, however, that support frame 60 may be disposed and nested on the inside of protruding lip 55 in the folded configuration. Moreover, the support frame 60 need not be nested with the protruding lip 55, and the present disclosure contemplates embodiments in which the support frame 60 has a larger perimeter or smaller perimeter than the protruding lip 55. Each of the support frame 60 and the tray 50 can have dimensions as discussed above with respect to medical device holder 20 of FIG. 1.

In the folded configuration, medical device holder 20 may be configured for easy storage, for example, but not limited to, within a base 10 as discussed further below.

Support frame 60 may pivot outwardly relative to tray 50 in order to move from the folded configuration to the open configuration. In the open configuration, as shown in FIG. 2A-3, support frame 60 may be planar with regard to protruding lip 55 such that a top surface of support fame 60 is generally flush with a top surface of protruding lip 55. Support frame 60 may form an opening 59 in the open configuration. As discussed further below, in the open configuration, the support frame 60 may support a sterile drape (such as the sterile drape 40 or other drape disclosed herein) or other flexible material so as to provide a flexible support pouch supported by the frame 60. In an embodiment, by placing a drape over the entire medical device holder 20, including both the tray 50 and the support frame 60 in the open configuration, the drape can provide a second holding region (within opening 59) for medical devices and their associated transmission lines. Such embodiments are described further below with reference to FIGS. 11A, 11B, as well as FIGS. 2C and 2D.

Tray 50 and support frame 60 may be made of a variety of materials such as, for example, plastic, metal, metal alloys, such as stainless steel, and/or other medical grade materials. In addition, the tray 50 and support frame 60 may be made of materials that are sterilizable, such that for example, a sterile drape may not be needed to be placed at least over the tray 50 during the surgical procedure. Tray 50 may include the same or different material from support frame 60. In some embodiments, tray 50 may be formed of a thin sheet of stainless steel over a thermoplastic body, and support frame 60 may be formed of a thermoplastic material.

FIGS. 2A-4 and 2A-5 show medical device holder 20 attached to an exemplary embodiment of arm 30 which, as discussed with reference to FIG. 1, can be used to support the medical device holder 20 and connect the medical device holder 20 to a base 10. An arm 30 supporting the medical device holder 20 may allow for movement of the medical device holder 20, and any medical devices held by medical device holder 20, into a variety of positions during a surgical procedure, as discussed further below. Tray 50 and support frame 60 can help to minimize the risk of medical devices falling off medical device holder 20 while medical device holder 20 is being moved into the variety of positions, thus protecting and enhancing the life and sterility of the medical devices. Although the arm 30 in FIGS. 2A-4 and 2A-5 is shown as having various joints, such a configuration is exemplary and non-limiting, and an arm without such joints, as well as an arm in accordance with any of the embodiments described herein, can be used to support the medical device holder 20.

Figures 2, 2A, 3, 4:
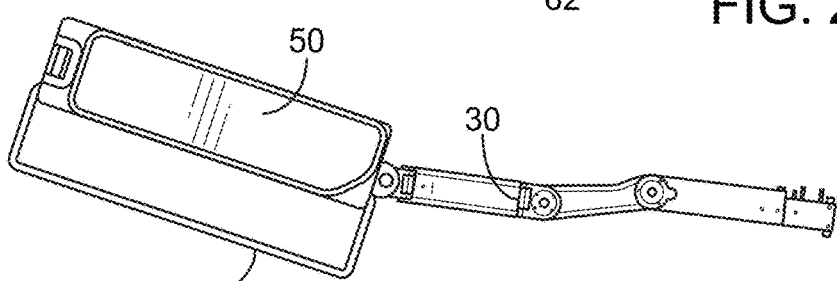
Figures 2, 2A, 3, 4, 5:
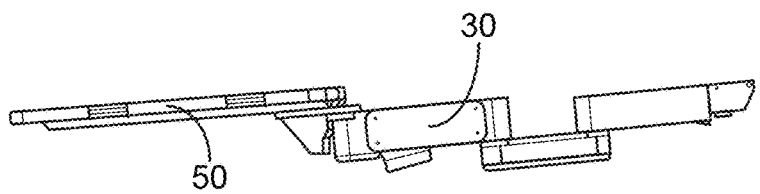
Figure 2B:
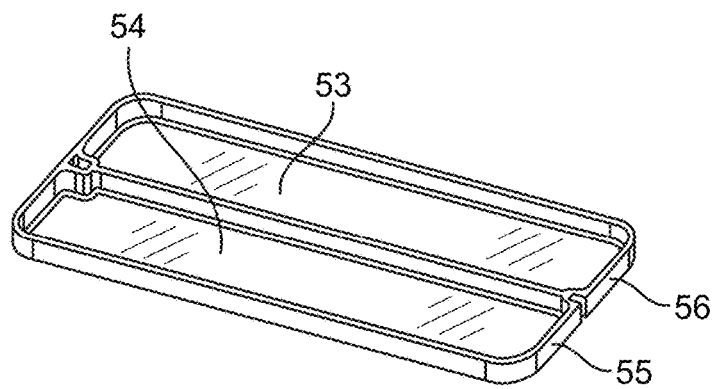

In some embodiments, as shown in FIG. 2B, medical device holder 20 may include a first tray 53 and a second tray 54, each with a protruding lip 56 extending from a flat, planar surface, similar to the structure of tray 50. First tray 53 and second tray 54 may be pivotally connected such that first tray 53 and/or second tray 54 rotates relative to each other into a folded configuration or an open configuration in a manner similar to how the support frame 60 and tray 50 fold and open in the embodiment of FIGS. 2A-1 through 2A-5. For simplicity, only the open configuration is depicted in FIG. 2B. Protruding lips 56 may be of similar size and shape on first tray 53 and second tray 54. Similarly, the overall dimensions of the trays 53 and 54 can be similar to place the trays in a nesting relationship when in the folded configuration. Alternatively, though not shown, the trays 53 and 54 could have different dimensions. Additionally, a portion of one of the protruding lips 56 may separate first tray 53 from second tray 54 such that the portion of the protruding lips 56 provides a barrier between the trays 53, 54 in the open configuration.

In other embodiments, protruding lips 56 on first tray 53 and on second tray 54 may be a continuous and unitary member, and the first tray 53 and second tray 54 may not be pivotably coupled and rotatable to the folded configuration; instead the trays 53 and 54 may be a monolithic, fixed structure.

Figures 1, 2C:
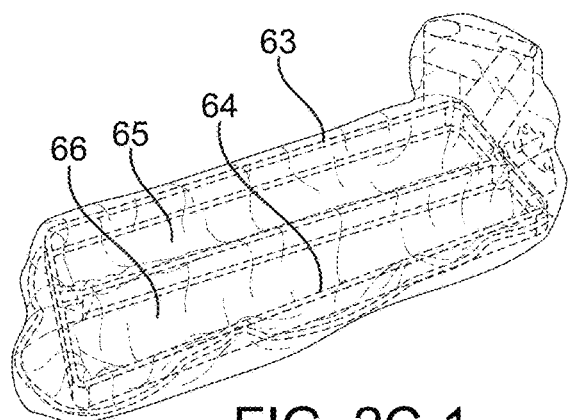
Figures 2, 2C:
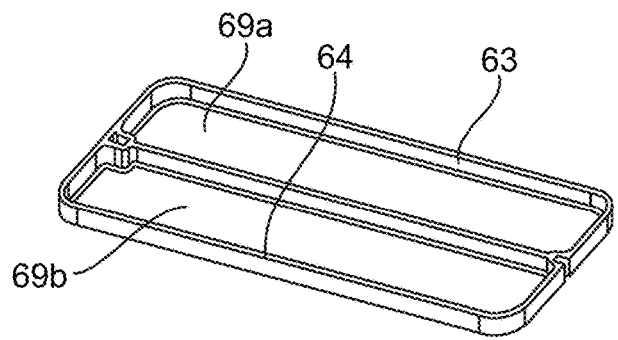

As shown in FIGS. 2C-1 and 2C-2, instead of having a first tray 53 and second tray 54 with the corresponding surfaces, a medical device holder 20 can have a similar configuration as described with respect to FIG. 2B, but with a first support frame 63 and a second support frame 64, each forming openings 69a and 69b and having structures similar to support frame 60 described in the embodiment of FIGS. 2A-1 through 2A-5. To provide surfaces for holding medical devices, a sterile drape or other sterilizable pouch, which can be permanently attached to the frames, can be provided to form wells 65, 66 (or other sized and shaped receptacles) extending from the support frames 63, 64 through the openings 69a and 69b. In some embodiments, the wells 65, 66 may be 8 inches×30 inches×7 inches deep. The drape or other sterilizable pouch disposed in the first support frame 63 may be the same or different from that disposed in the second support frame 64. One or more medical devices and/or cables may be stored within the wells 65, 66 thus formed.

Similar to the configuration described with reference to FIG. 2B, the overall dimensions of the support frames 63, 64 can be similar to place the frames in a nesting relationship when in the folded configuration. Alternatively, though not shown, the support frames 63, 64 could have different dimensions. Additionally, protruding lip 55 may separate support frames 63, 64 such that protruding lip 55 provides a barrier between the frames in the open configuration.

Figure 2D:
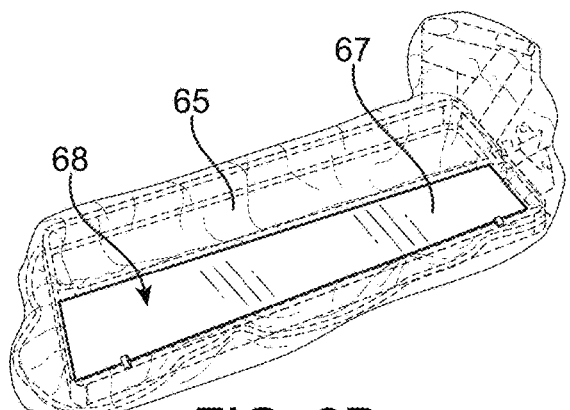

In one embodiment, an optional removable surface 67 may be disposed on a top portion of one of the wells 65 or 66, thus covering one of the openings 69a or 69b, as shown in FIG. 2D. Removable surface 67 may be configured to hold and secure one or more medical devices and/or miscellaneous items, similar to a tray. The removable surface 67 can be sized to provide a friction fit with the interior of the support frame 60, 63, 64, e.g., the interior surface of protruding lip 55, sufficient to hold medical devices without deforming the removable surface 67 or causing it to fall through the opening of the support frame. A top surface 68 of removable surface 67 may be planar or recessed slightly below a top surface of the support frame in which it sits. In the latter case, the support frame 64 provides a protruding lip surrounding the support surface 67, similar to the trays in the other embodiments described above. The removable surface 67 may be made of, for example, plastic, metal, paperboard, foam, rubber, etc. In addition, it may be provided with a textured surface (not shown) to provide better friction and prevent slipping and/or rolling of medical devices placed thereon. In some embodiments, the top surface 68 may include one or more widthwise and/or lengthwise depressions or grooves (not illustrated) to aid in organizing instruments, and inhibiting rolling of instruments on the top surface.

Drapes, pouches, and removable surfaces as described herein may be made of medical grade materials that are disposable or reusable. In the latter case, the materials should be sterilizable.

Figure 2E:
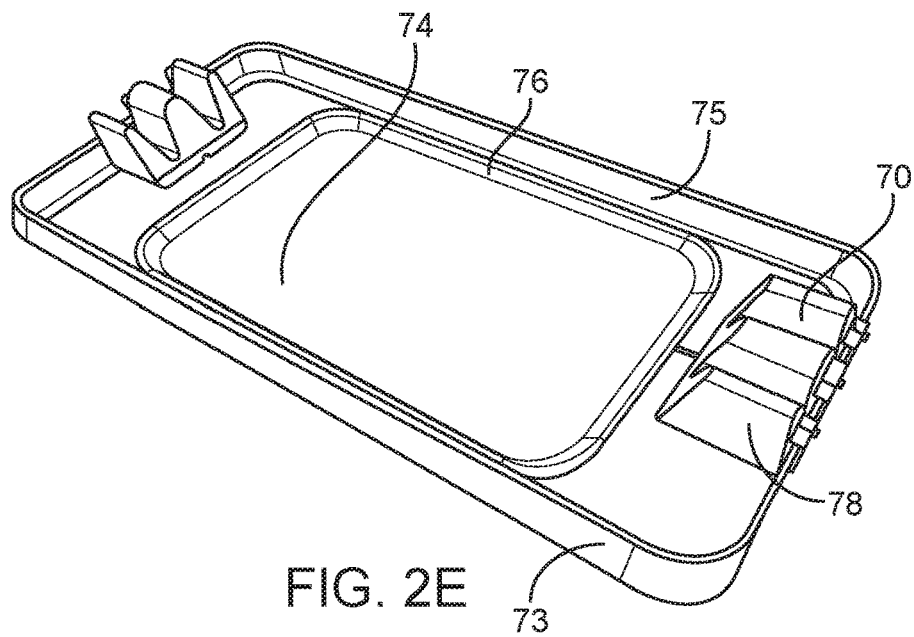

In some embodiments, as shown in FIG. 2E, a medical device holder 20 can include a first larger outer tray 73 (also referred to herein as "first tray" or "outer tray") and a second smaller inner tray 74 (also referred to herein as "second tray" or "inner tray") supported within the outer tray 73. In other words, the inner tray 74 can nest within the outer tray 73. Each of the trays 73, 74 can have a protruding lip 75, 76, respectively, extending from a flat, planar surface such as those described elsewhere herein By way of non-limiting examples, the first and second trays can each be formed of metal or thermoplastic, with the inner tray 74 having dimensions generally the same as other trays described in the exemplary embodiments above and the outer tray 73 having sufficiently larger dimensions to hold the inner tray 74. In an exemplary embodiment, the inner tray 74 has dimensions of the largest dimensions provided above with respect to other tray embodiments and the outer tray 73 has dimensions of 13 inches×20 inches. The arrangement of the trays allows the inner tray 74 to be removably held by the outer tray 73. Protruding lip 75 may have a height substantially equal to or larger than protruding lip 76. In an exemplary embodiment, protruding lip 75 can be slightly larger (e.g., 0.25 inches to 1 inches larger) than protruding lip 76 to accommodate the inner tray 74. As discussed above, both first tray 73 and second tray 74 may be configured to secure and hold one or more medical devices, such as, for example, an endoscope and/or various surgical instruments. First tray 73 may also include one or more recesses 70 on either or both end of the tray to hold one or more tips and/or shafts of medical devices in a secure manner, such as via a friction fit, and/or to capture and route transmission lines connected to the cables. Thus, for example, the handle of a medical device can be disposed on second tray 74 and the tip of the medical device can be secured within recess 70 of first tray 73. As shown in FIG. 2E, recesses 70 may provide additional stability to minimize and/or prevent the endoscope from rolling off of first and second trays 73, 74. Further, such recesses can protect delicate tips of medical devices when not in use. Recess(es) 70 can be formed integrally in or with outer tray 73 or can be part of a separate block 78 attached to the bottom or edge (or both) of the tray. In some embodiments, recesses 70 may have a V-shaped cross section, while in other embodiments may have a flared cross-section, such as the cross-section of a trumpet bell.

In the embodiment of FIG. 2E, inner tray 74 may be disposed on outer tray 73 without any separate attachment means. Alternatively, inner tray 74 may be secured to outer tray 73 with one or more attachment mechanisms such as, for example, an adhesive, a hook-and-loop-pile type fastener (e.g., Velcro), etc. Such attachment mechanisms may allow inner tray 74 to be removably attached to outer tray 73 without damaging or destroying the trays or the attachment mechanism. It is also contemplated that outer tray 73 includes a friction-inducing material in order to minimize any sliding of inner tray 74 relative to outer tray 73.

Figure 2F:
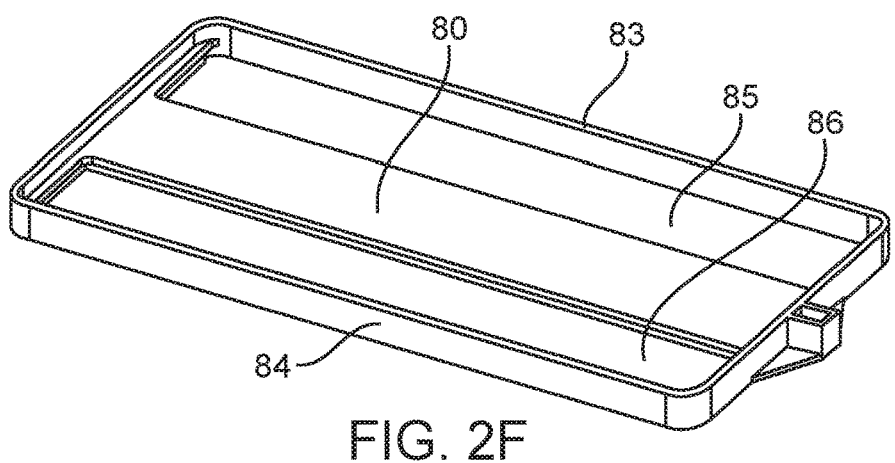

In the embodiment of FIG. 2F, medical device holder 20 includes a center tray 80, with support frames 83, 84 having openings 85, 86 on opposite sides of the tray 80. This embodiment can function similarly to any of the embodiments described herein, as would be apparent to one having ordinary skill in the art. In an embodiment, the frames 83, 84, and tray 80 can be pivotably connected to provide a tri-fold configuration, including pivots and stops similar to those described with reference to FIGS. 2A-2 and 2A-3, or can be fixedly connected and integral (e.g., monolithic structure). As discussed above, one or more drapes or sterilizable pouches can be disposed in the frames 83, 84 (see FIGS. 2C-1 and 2D) to provide wells to hold, e.g., medical devices and associated transmission lines. Additionally, medical instruments and other components may be disposed on tray 80. In an embodiment, the entire medical device holder, including the tray 80, can be draped.

Figure 2G:
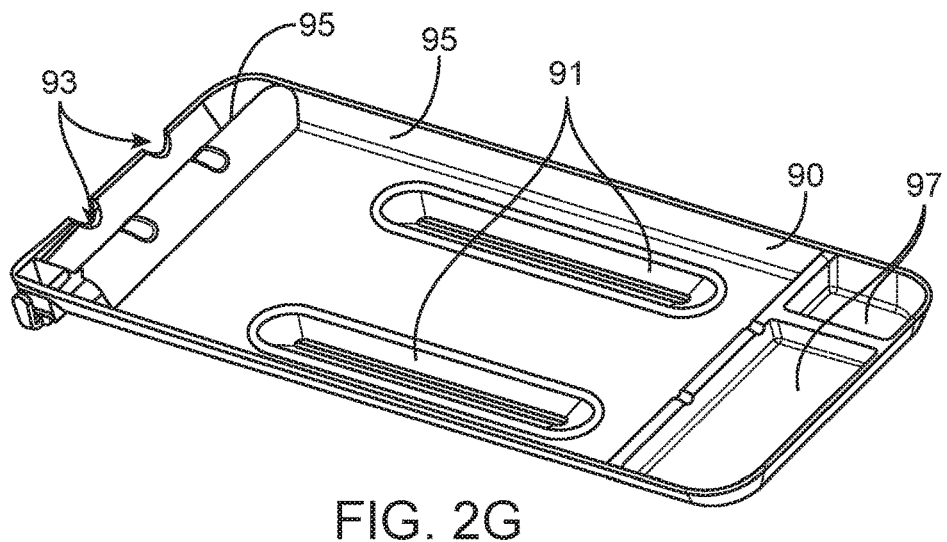

In some embodiments, as shown in FIG. 2G, medical device holder 20 includes a tray 90 with a flat, planar surface and one or more depressions to form receptacles 91 therein. Receptacles 91 can be sized and shaped to receive one or more medical instruments. Thus, receptacles 91 may be a cavity on tray 90 in order to securely maintain the medical devices on tray 90, and thus minimize the risk of the medical devices falling off tray 90. As shown in FIG. 2G, medical device holder 20 may include additional storage compartments, such as recesses 93 sized and shaped to receive and route transmission lines of medical devices. Recesses 93 may be formed in a separate member from a protruding lip 95 of the tray or may be formed on a top surface of protruding lip 95. Additionally or alternatively, medical device holder 20 can include compartments 97 to store a variety of miscellaneous objects. Compartments 97 may be a unitary member with protruding lip 95, or compartments 97 may be formed separately from protruding lip 95. As shown in FIG. 2G, protruding lip 95 may form an outer side surface of compartments 97. Areas of the tray 90 also can be made of different materials. For example, foam, rubber or another deformable material may be used for the regions including the recesses 93 and compartments 97, while the region having the receptacles 91 may be made of another material, such as stainless steel or other medical grade metal or plastic. In an exemplary embodiment, the main body region with the receptacles 91 can be sterilizable and reusable, and the end regions forming the compartments 97 and/or recesses 93 can be disposable and configured to be attached via friction fit or other removable coupling mechanisms on the main body portion.

Figure 2H:
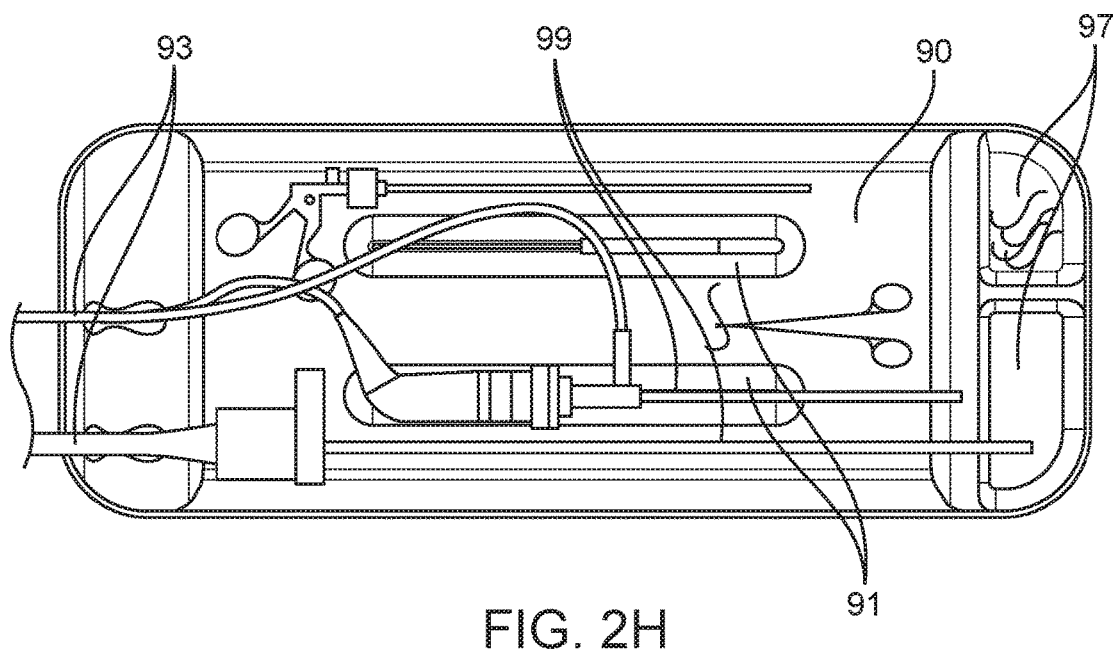

FIG. 2H shows a plan view of the medical device holder 20 of FIG. 2G showing various surgical instruments 99 in the receptacles 91 and on the flat surface of the tray 90, as well as other devices, which may be used during a surgical procedure, placed in the receptacles 91 and compartments 97. Also shown in FIG. 2H is how transmission lines connected to the instruments 99 can be received and routed through the recesses 93, with tips of the instruments being placed to reside over the compartments 97.

Figure 21:
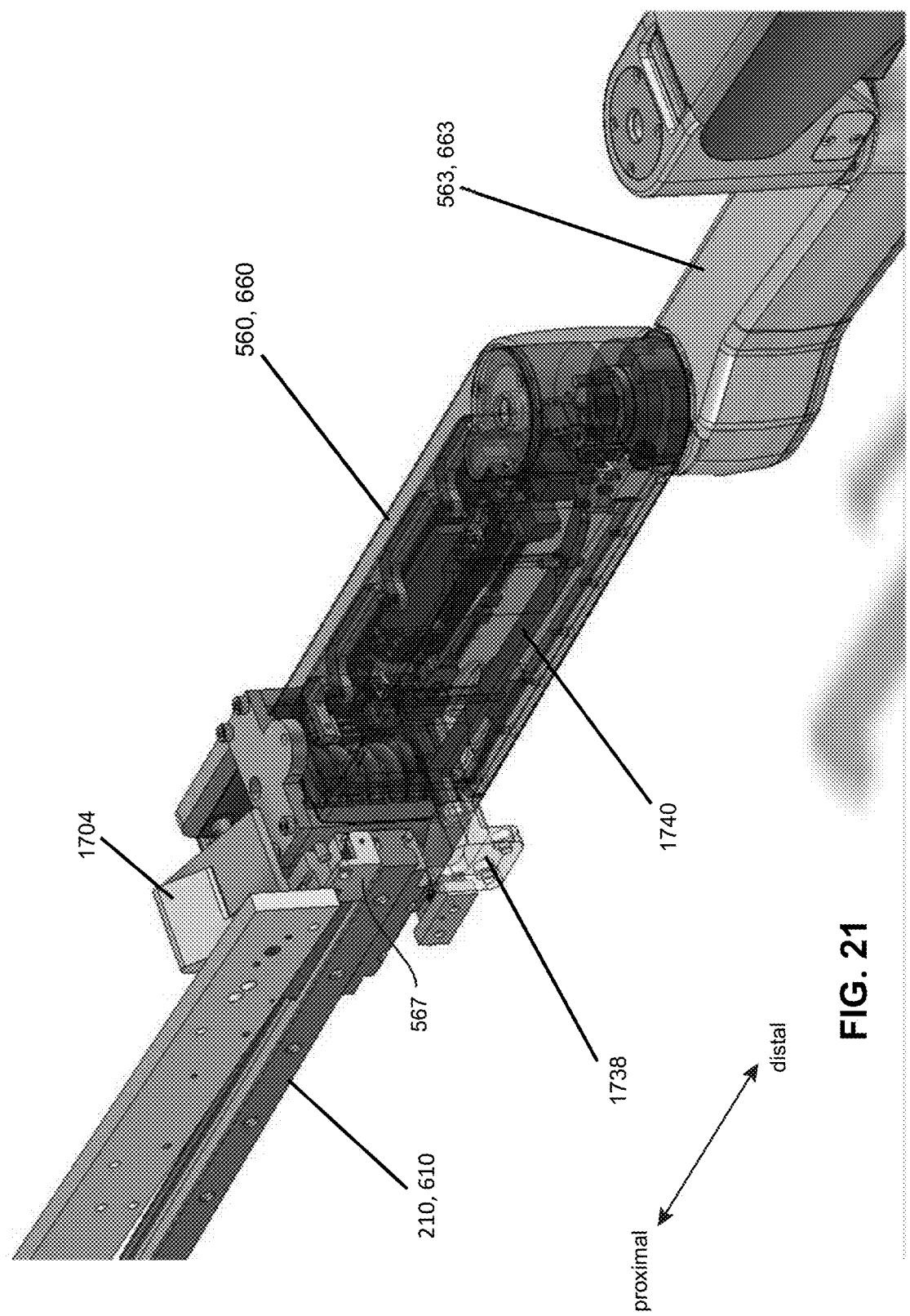
FIG. 21 shows a perspective view, with portions transparently shown, of another exemplary embodiment of an internal lock mechanism for a link member.

Receptacles in trays of medical device holders disclosed herein may be of varying sizes and shapes and may be configured to receive one or multiple medical devices and at least a portion of their cables. For example, as shown in FIG. 21, a tray 100 can have a receptacle or set of receptacles 101 configured to store the shafts of two or more endoscopes or other instruments, with the tips of the shafts secured within recesses 103 at one end of the tray sized to provide a friction fit to hold the tips of the shafts. Additionally, the handles of the endoscopes or other instruments may be disposed in a second receptacle 104, or set of receptacles. As shown in FIG. 21, the receptacles 101 can be dimensioned to receive at least a portion of the transmission lines of the two endoscopes to facilitate transmission line organization.

Figure 2I:
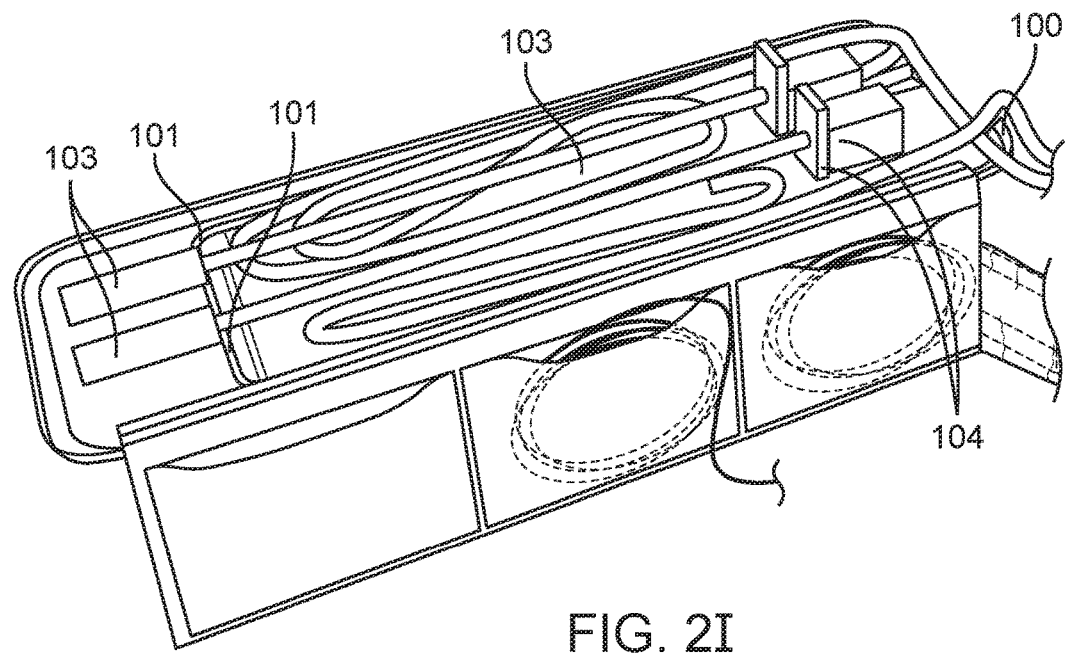
Figure 2J:
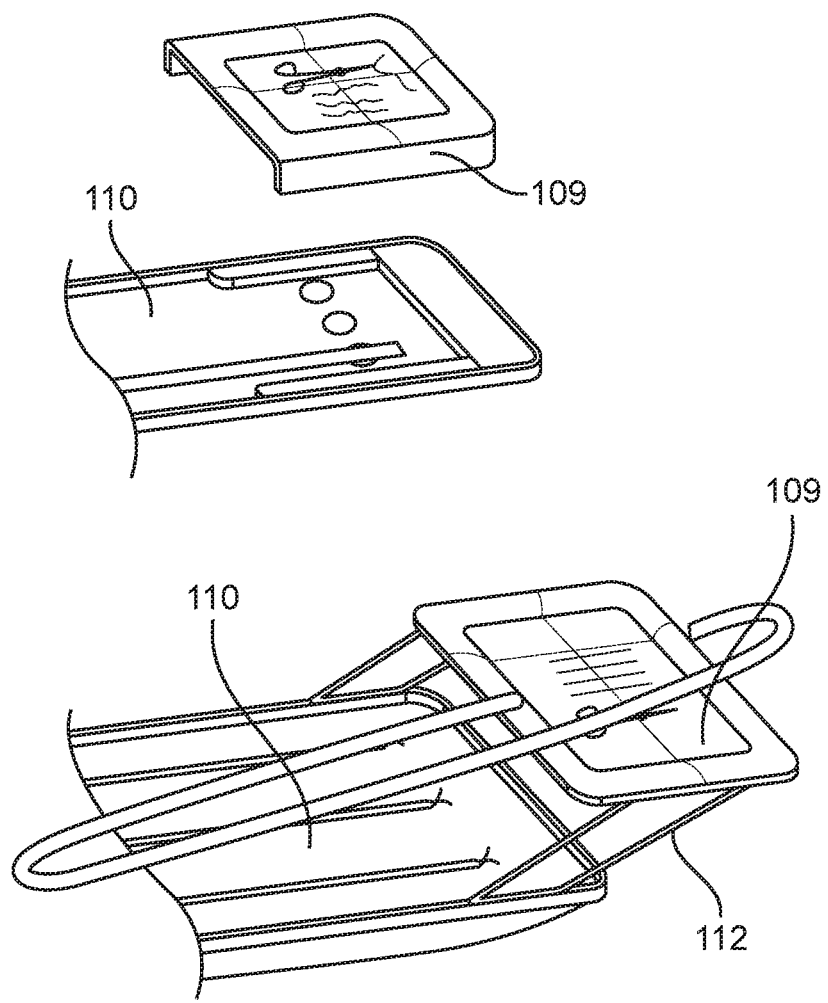

Medical device holders in accordance with various embodiments can include a variety of other components that assist with organization, access to, and maintaining sterility of various devices that may be used during a surgical procedure. With reference to FIG. 2J, a smaller, accessory tray 109 can be included that is configured to be removably and/or movably coupled to tray 110. Such an accessory tray 109 can be useful to hold various smaller devices, such as for example, needles and scissors, that are useful in surgical procedures. The accessory tray 109 may be removably attached to be clipped or snap-fit into position over a portion of the tray, as shown in the upper illustration of FIG. 2J. In another embodiment, the accessory tray 109 can be raised above the tray 110, as shown in the lower illustration in FIG. 2J. For example, one or more legs 112 can attach the accessory tray 109 to tray 110. Optionally, the legs can be pivotable relative to the tray 110, and optionally allow pivoting motion of the accessory tray 109 relative to tray 110. By way of a non-limiting example, the legs 112 may form one or more four-bar linkages with the tray 110 and the accessory tray 109. Therefore, the legs 112 may allow accessory tray 109 to pivot from a first configuration disposed over and adjacent tray 110, to a second configuration in which the accessory tray 90 is vertically displaced relative to tray 110. Legs 112, accessory tray 109, or both, may optionally include locks or the like to secure the tray 109 in the lower orientation, the raised orientation, or both. One of ordinary skill in the art would appreciate a variety of manners in which the accessory tray can be attached to and located relative to any of the trays or support frames of medical device holders described above, without departing from the scope of the present disclosure. Accessory tray 109 may include one or more of the additional features described with reference to the exemplary embodiment of FIG. 2G-2I, such as various recesses, compartments, pouches, receptacles, and may be made of, for example, plastic, metal, paperboard, foam, rubber, etc., including sterilizable materials if intended to be reusable.

Figures 1, 3A:
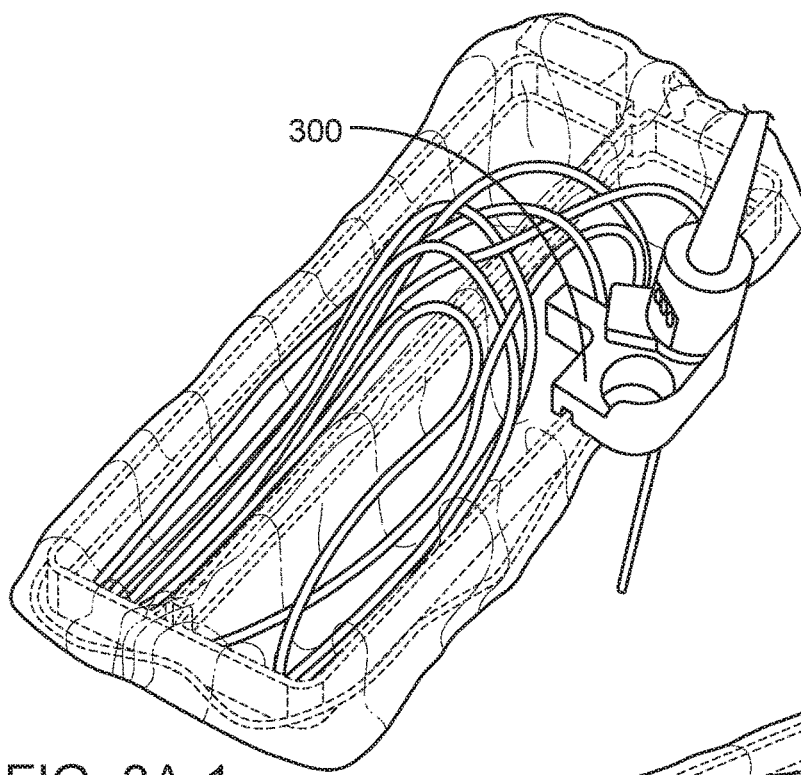
Figures 2, 3A:
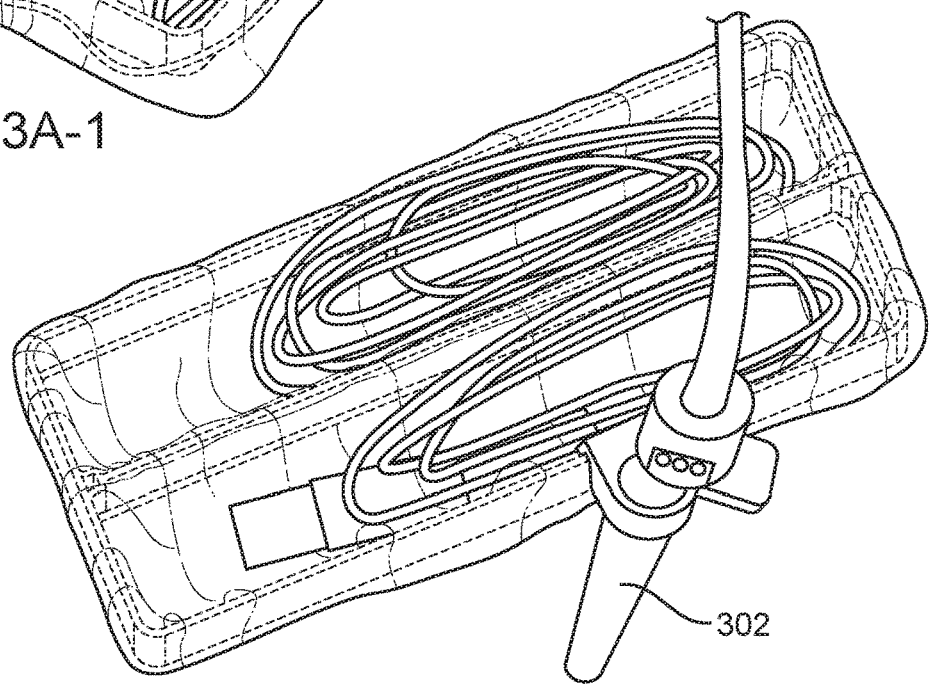

In other embodiments, various other storage devices can be included as part of a medical device holder 20. As shown in FIGS. 3A-1 and 3A-2, a holster 300 having a receptacle sized and shaped to receive a shaft of a surgical instrument, including an endoscope, can be attached to the outer periphery of the medical device holder 20. In one embodiment, holster 300 is clipped onto the protruding lip of a tray or a frame, with the receptacle oriented vertically. Holster 300 can be removably or fixedly secured to medical device holder 20. As shown in FIG. 3A-1, holster 300 may be used to secure medical instruments in a vertical position. As shown in FIG. 3A-2, holster 300 may include an elongated sheath or cover 302 extending downward from the holster, of a length sufficient to cover and protect the surgical instrument, including a distal tip of the surgical instrument.

Figure 3B:
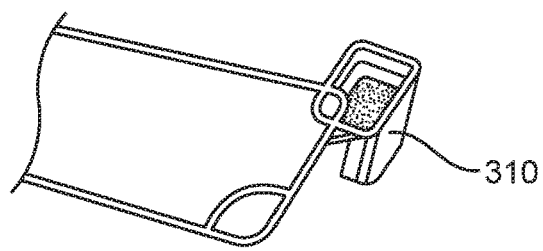

Other storage compartments include removable or fixedly coupled cartridges 310, as shown in FIG. 3B. Such cartridges 310 may be, for example, clipped onto a protruding lip of a tray or the frame. A variety of objects may be stored within cartridges 310, such as, for example, sutures, gauze, etc. Cartridges 310 also can be used to store liquids, such as liquids to clean various medical devices, such as endoscopes, for example, during a medical procedure.

Figures 1, 3C:
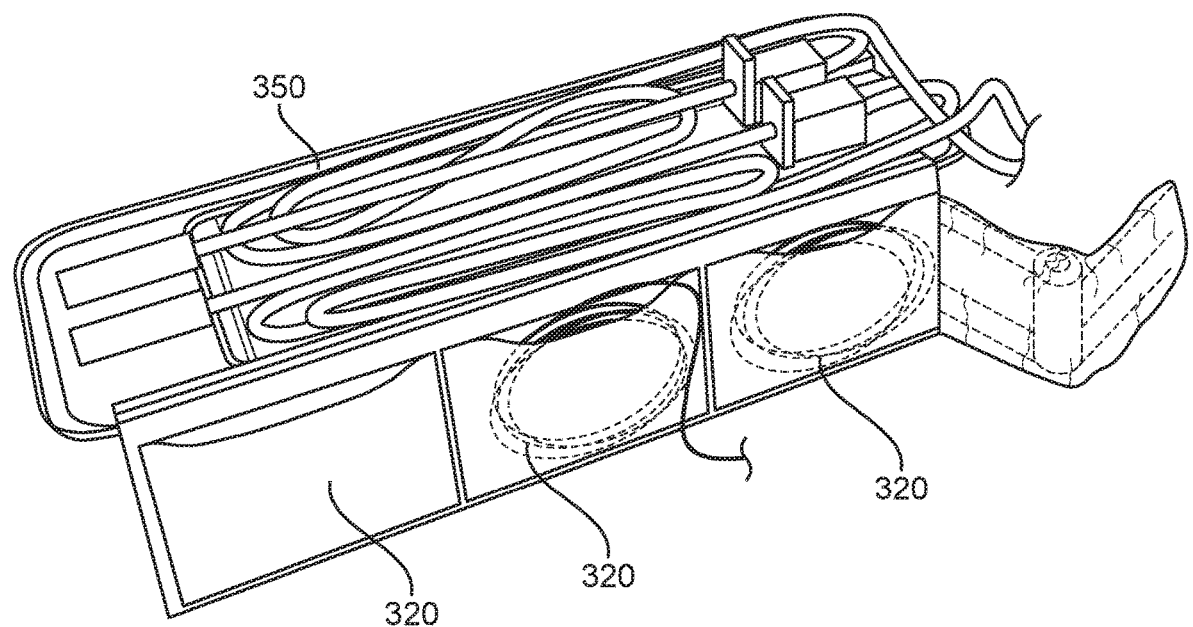
Figures 2, 3C:
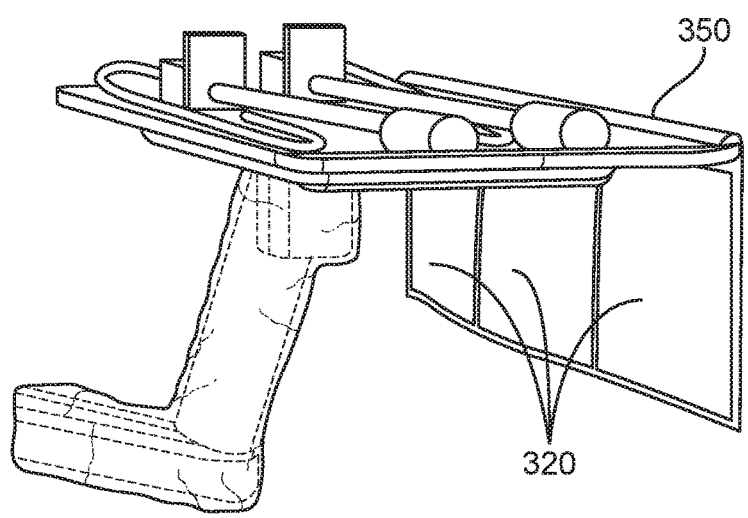
Figure 4:
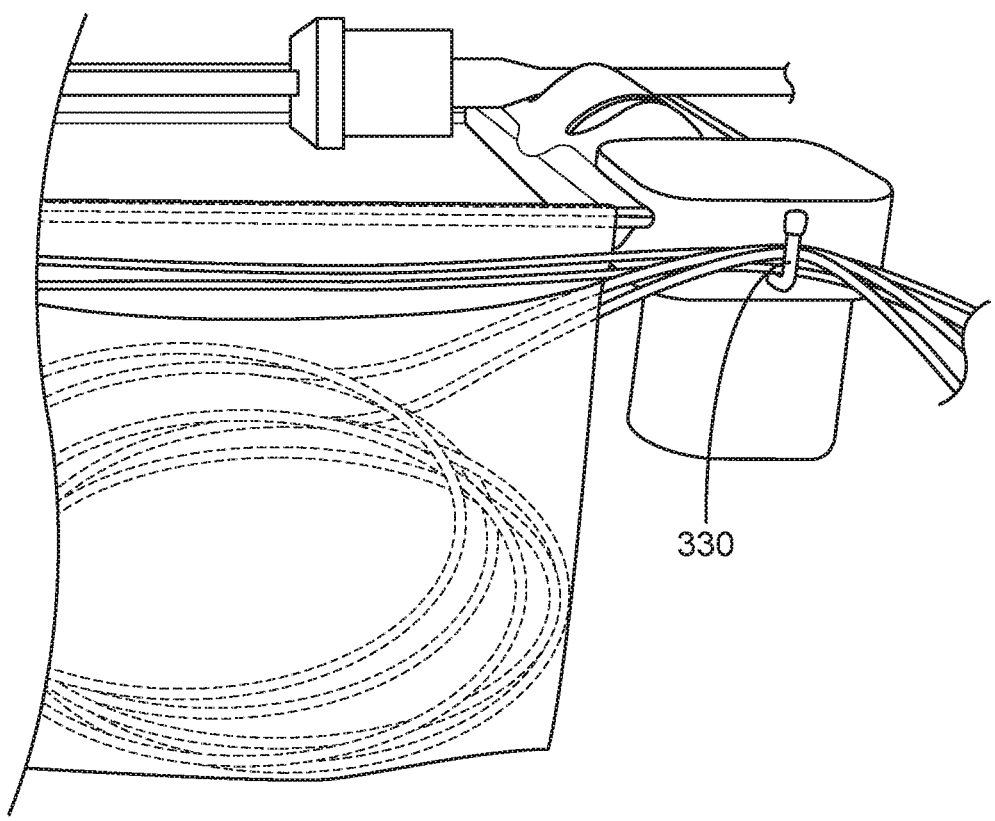

A medical device holder in accordance with various embodiments also may include one or more pouches (e.g., pockets) 320 that hang from an outer periphery of the frame or tray of the medical device holder. As shown in FIGS. 3C-1 and 3C-2, pouches 320 can be removably attached or fixedly secured to a side or other edge surface of a tray 350, for example, to the protruding lip, or support frame (not shown). In some embodiments, pouches 320 are attached to a tray or support frame using an adhesive, a clip, a snap-fit mechanism, or other suitable attachment device. As shown in FIGS. 3C-1 and 3C-2, pouches 320 hang downward from the tray 350. Pouches 320 can be sized and shaped to provide convenient storage for a variety of objects including, for example, transmission lines of medical devices, as depicted in FIG. 3C-1. Pouches 320 may each be connected together or may each form separate members when attached to medical device holder 20. In the example of FIGS. 3C-1 and 3C-2, three pouches are shown, but any number is within the scope of this disclosure. The pouches 320 may all be the same size, or the pouches 320 may be differently sized. Pouches 320 can be made of flexible and durable material such as, for example, polyethylene (PE), polypropylene (PP), polystyrene (PS), or polyvinyl chloride (PVC). In one embodiment, the tray and/or support frame of the medical device holder and the pouch can be sterile or formed of a material which is sterilizable. In another embodiment, the pouch can be packaged as a sterile, disposable component and configured to be attached to a reusable and sterilizable tray and/or support frame. In some embodiments, a pouch may be up to 11 inches deep, such as, for example, 6-8 inches deep, and have a width up to the length or width of the tray from which it is hung.

Medical device holder 20 also can include or be configured to receive a variety of transmission line routing features. For example, various clips, hooks, and the like can be used to organize and route transmission lines of medical devices. FIG. 4 provides an example of a hook 330 that may be used to route transmission lines, which can be placed in pouches, as shown, or not. Hook 330 may be used to prevent sagging, tangling, and general disorganization of transmission lines when medical instruments are held by a medical device holder. Various other transmission line routing structures are discussed further below.

It is within the scope of this disclosure that various aspects of the above-discussed embodiments of medical device holder 20 may be combined. Thus, the features of each of these embodiments may be combined with features of the other embodiments. Various features of the different embodiments are not mutually exclusive and, instead, can be combinable as those have ordinary skill in the art would understand Medical device holder 20 provides enhanced instrument and cable organization compared to conventional surgical instrument trays, such as Mayo stands. For example, the flexible support wells, trays with lips and various receptacles, tip and transmission line recesses, pouches and other storage compartments and devices provide for easy storage of the medical devices, associated transmission lines, and other devices that may be used during a surgical procedure. Moreover, the medical device holders and related systems can provide for an overall efficient workflow prior to and during a surgical procedure. Additionally, medical device holders and related systems can allow medical devices to be easily switched in and out of use during a surgical procedure.

Further, medical device holders in accordance with various embodiments are configured to minimize the risk of medical devices falling off the medical device holder, thus reducing the risk of potential damage to such medical devices and increasing the lifespan of thereof.

Support Arm for Medical Device Holder

As mentioned above, medical device holder 20 can be fixed to or removably coupled to an arm 30 extending from a base 10. In embodiments wherein the medical device holder 20 can be removably coupled to the arm 30, the medical device holder 20 can be provided sterilized, and additionally may be sterilizable (e.g., autoclavable) to provide for reuse. Providing a removable medical device holder 20 that is sterile or sterilizable may allow for simplicity in the setup of the operating theatre, and potentially reuse of the medical device holder 20 over multiple procedures. Further, a sterile drape over the medical device holder 20 may not be required in such an embodiment. It also may facilitate post-procedure reprocessing of medical devices held on the medical device holder 20 by allowing the medical device holder 20 with medical devices held thereon to be removed from the arm 30 and moved to a remote location for cleaning. Moreover, removal of the medical device holder 20 from the arm 30 may facilitate storage of the arm and any base to which it is attached.

In addition, permitting the medical device holder 20 to be removable from arm 30 can enhance the use of the medical device holder 20. For example, a user may disconnect medical device holder 20 from arm 30 in order to move medical device holder 20 to another position in the operating room that is remote from arm 30 and base 10.

All of these various features can result in creating an overall efficient workflow.

Figure 5A:
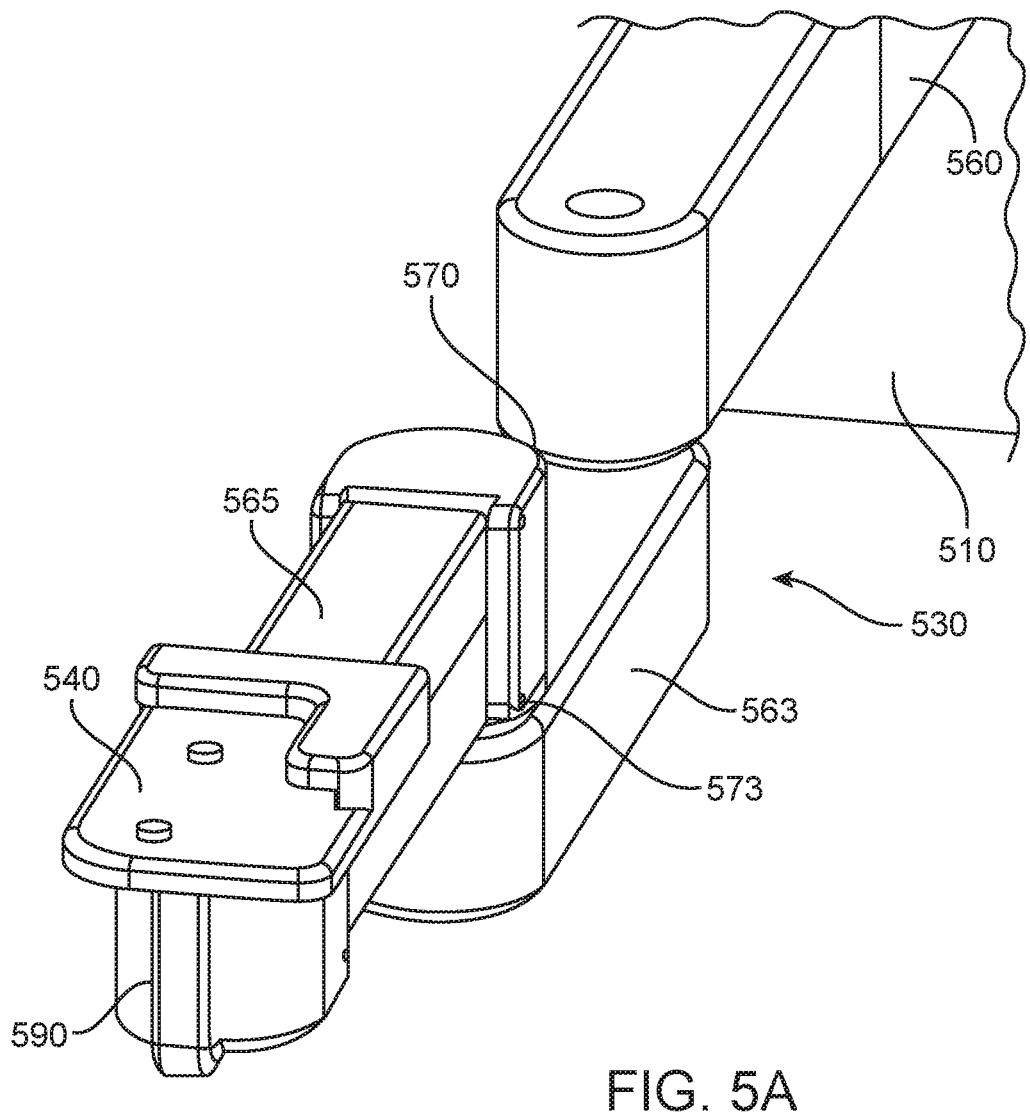
FIG. 5A shows a perspective view of an exemplary embodiment of an arm in an extended configuration in accordance with the present disclosure.
Figure 5B:
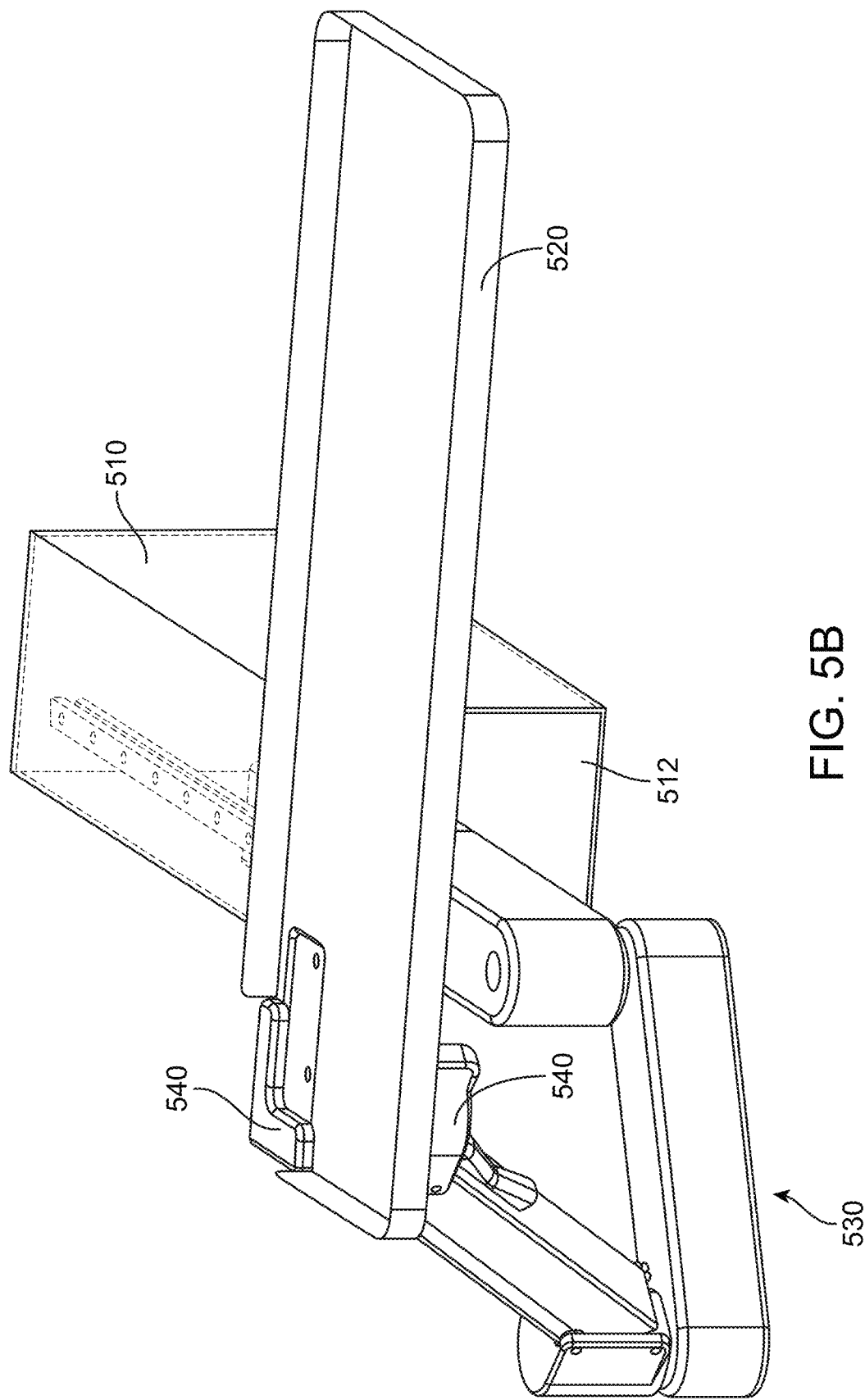
FIG. 5B shows a perspective view of an exemplary embodiment of the arm of FIG. 5A with a medical device holder attached in accordance with the present disclosure.

FIGS. 5A and 5B show an embodiment in which an arm 530 attaches to a base 510 at one end and includes a sterile adapter member 540 at a distal end of the arm 530 opposite the end that attaches to the base 510. Arm 530 may be used as arm 30, and base 510 may be used as base 10. Arm 530 and base 510 can have a variety of configurations with the embodiment depicted in FIGS. 5A and 5B being nonlimiting; additional details and embodiments of arms and bases, and connections thereof, in accordance with the present disclosure are discussed below. By including a sterile adapter member 540 on the arm 530, a sterile medical device holder 520 (e.g., from a package or otherwise sterilized prior to use) can be coupled to the sterile adapter member 540 by way of integrated attachment features (e.g., clips, grooves, undercuts, etc.) or by sterile bolts, screws, and/or other fasteners provided and used to secure the medical device holder 520 to the arm 530 (see FIG. 5B). Medical device holder 520 is shown as a tray in FIG. 5B but any of the medical device holder configurations described herein can be used. Thus, in the embodiment of FIGS. 5A and 5B, sterile draping of only the arm 530, and the sterile adapter 540, may be needed. Alternatively, the sterile adapter 540 with the fasteners can be provided as a separate sterile component along with the medical device holder 520, thus requiring draping only of the arm 530. In either case, the fastening mechanism(s) used to attach the medical device holder, sterile adapter, and arm can be such as to operate through the drape.

Other connections of the medical device holder 20 to an arm 30 are envisioned as well. For example, whether for the embodiment of FIGS. 5A and 5B or other embodiments, including when the medical device holder 20 is fixedly coupled to arm 30 (in which case draping of the arm 30 and medical device holder 20 is envisioned), the medical device holder 20 can be rotatably or pivotably coupled to the arm 30 to allow some range of movement relative to the arm 30. In this way, the medical device holder may be moved into a variety of orientations and positions to facilitate access to medical devices on the medical device holder 20 or clearing of areas within the sterile field by moving the medical device holder 20 out of the way. In an exemplary embodiment, a medical device holder can rotate in a plane of the medical device holder and relative to a distal end of the arm over a range from 0 degrees to 360, and any sub-range therein. In an exemplary embodiment, the coupling mechanism between the arm and the medical device holder may allow for rotation in either direction. Moreover, the rotatable coupling mechanism can provide sufficient friction so that the angular position of medical device holder 20 relative to the arm 30 is maintained as the medical device holder 20 assumes a variety of positions. By way of a non-limiting example, a coupling mechanism may include a rotating shaft (not illustrated) extending from the arm, supported by rotary bearings (not illustrated) in the arm, and the sterile adapter member may include an undercut or flexible tabs (not illustrated) which permits the sterile adapter member to snap onto the rotating shaft. Those having ordinary skill in the art would recognize various other rotatable coupling mechanism could be used to couple the medical device holder to the arm.

Additionally, medical device holder 20 may be coupled to arm 30 so as to provide a slight tilt of the medical device holder 20 (e.g., along a pitch and/or roll axis of the medical device holder), relative to the arm 30. Thus, medical device holder 20 may move upward and downward relative to arm 30. Providing the ability to slightly tilt may allow the medical device holder to absorb unintended bumps or movements that may otherwise cause the medical device holder to become dislodged from the arm or affect the securement mechanisms.

While the present disclosure contemplates the use of arms with a single link member and relatively simple structure, such as generally a beam extending from a base 10, various exemplary embodiments contemplate an arm that is jointed and can provide a range of motion and positioning, relative to both the base and the medical device holder, that enhances user access, flexibility of use, and reach into the sterile field, while maintaining secure holding of medical devices and connection of medical devices to auxiliary equipment outside the sterile field, as well as organized cable routing. Moreover, various arm configurations can provide safety features that may minimize the risk of damage and/or undesirable or unexpected movements of equipment within the operating theatre.

Figure 6D:
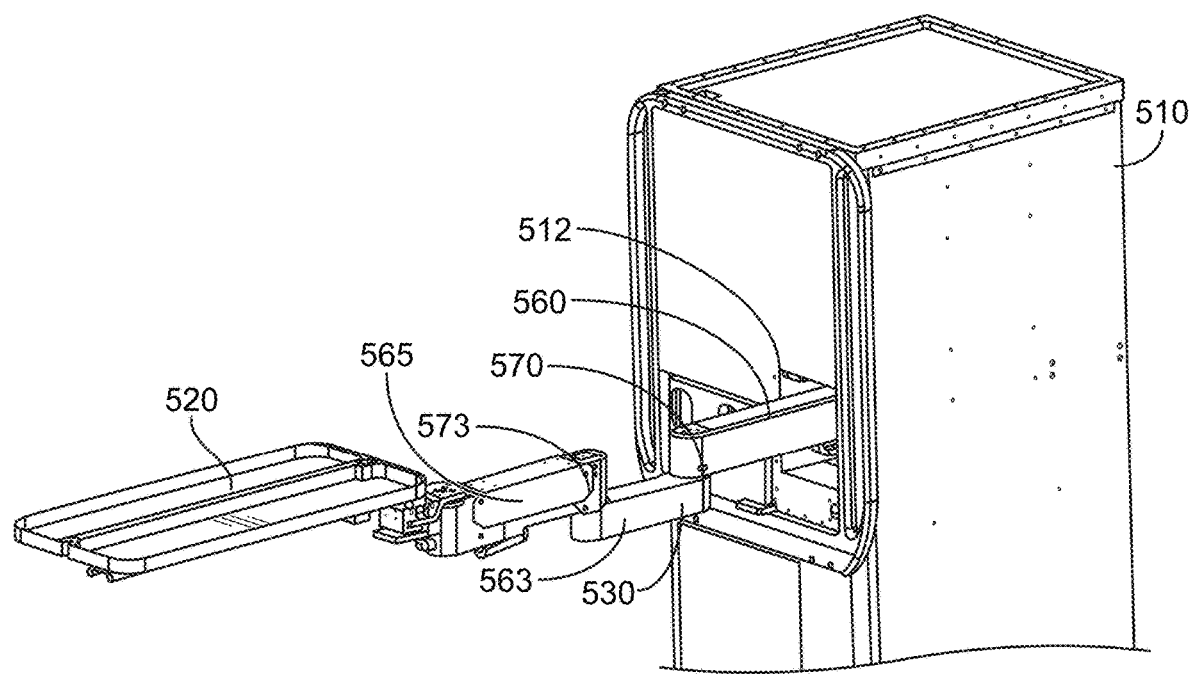
FIGS. 6D and 6E show further illustrations of various extended configurations of the arm of FIGS. 6A-6C with a medical device holder attached relative to a base in accordance with the present disclosure.
Figure 6E:
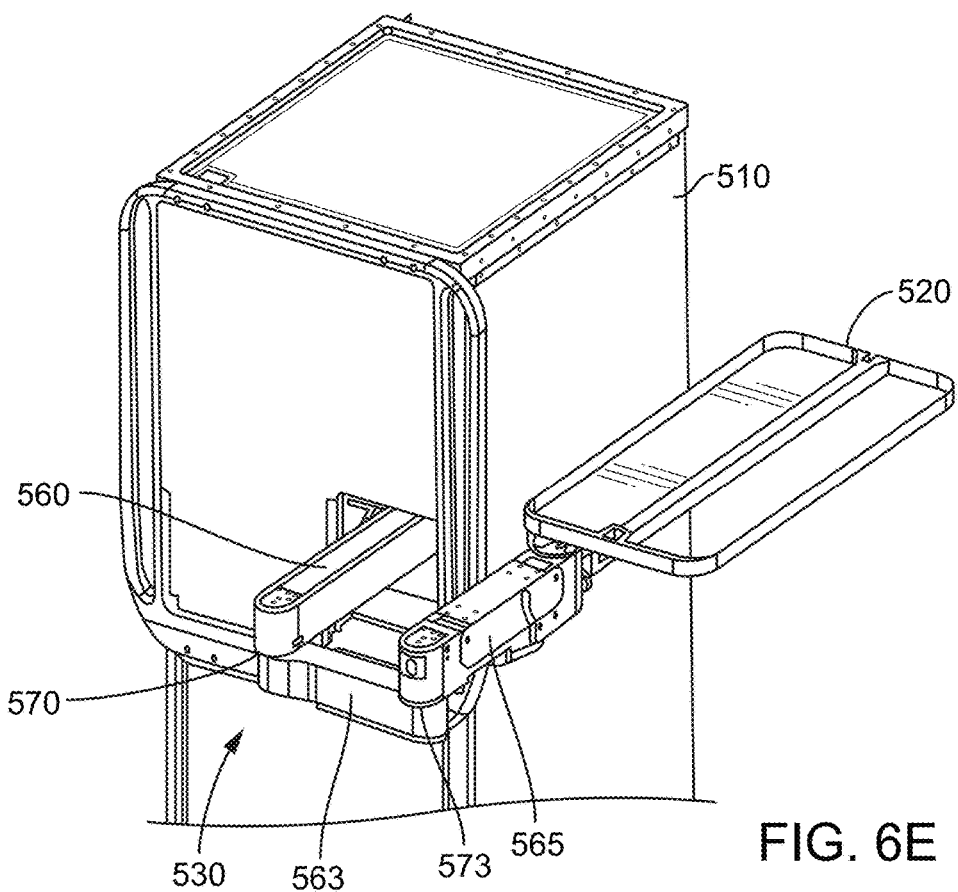

In an exemplary embodiment, as shown with reference again to FIGS. 5A and 5B, and to FIGS. 6A-6C, arm 530 can be configured to have an extended and a retracted configuration relative to the base 510. In some embodiments, the base 510 comprises a compartment 512 and the arm 530 is received within the compartment 512 in a retracted configuration, as shown in FIG. 6C and described further below. In some embodiments, the base 510 may comprise other portions in addition to the compartment 512, as illustrated in FIGS. 6D and 6E.

As shown, arm 530 includes a first link member 560, a second link member 563, and a third link member 565. The first and second link members 560, 563 and the second and third link members 563, 565 can be rotatably coupled at first and second joints 570, 573, respectively. Further, as described above, a medical device holder can be connected by a rotatable coupling at a distal end of the third link member 565, with the sterile interface adapter connection shown and described in FIGS. 5A and 5B being one non-limiting embodiment of such a connection; other connections between third link member 565 and a medical device holder can be used.

In some embodiments, the arm 530 is configured to allow repositioning of the holder without risk of the transmission lines becoming detached from the base 510 or the medical devices being pulled off of the holder due to a change in cable distance between the transmission line ends, regardless of the position of the medical device holder. It may therefore be advantageous for the first link member 560 to have a fixed position after deployment (discussed in greater detail below) into the extended position, with the transmission lines being routed through a retaining device, e.g., a clip, at the end of the first link member 560 (also discussed in greater detail below). The remaining link members can be rotationally coupled to each other with transmission lines routed through guide features attached to one or more of the rotational joints so as to minimize the change in length of the transmission lines during repositioning of the arm and medical device holder.

The range of motion of the arm 530 may be limited to assist in minimizing inadvertent contamination of the sterile medical device holder and sterile portion of the arm 530 and transmission lines, for example, by coming into contact with the non-sterile base. The fixed position of a first transmission cable guide device, e.g., clip, after the first link member is deployed, can be selected to enforce adequate distance between the non-sterile base and the sterile portion of the transmission lines, so that a draped arm can be manipulated by a sterile user without fear of contamination. Additional features, described elsewhere herein, may also be used to enforce this, such as, by way of non-limiting examples, locking out the first link member 560 when deployed to prevent the first link member 560 from sliding back (retracting back) into the base 510, limiting the rotational range of motion of the second link member 563 when draped, and including in the system mechanisms which tend to promote moving the holder is fully extended before providing the ability to drape the holder and arm 530.

As discussed further below, first link member 560 connects to base 510 such that first link member 560 can move in translation relative to base 510. This can allow the arm 530 to extend and retract in translation toward and away from the base 510, as illustrated in the positions of the first link member 560 shown in FIGS. 6A-6C. Additionally, in various exemplary embodiments, a pivoting connection may be used such that at least when first link member 560 reaches an extended configuration from the base 510, as shown in FIGS. 6A and 6B, it can also pivot to some degree of rotation relative to the base 510 (e.g., about an axis parallel to the axes of rotation of the first and second joints 570, 573).

Thus, first link member 560, second link member 563, and third link member 565 are configured to be folded relative to each other to provide a compact configuration for the arm 530 when not in use, for example, to be retracted into base 510, as discussed further below, and also to provide a range of orientations of the arm 530 and the medical device holder as those having ordinary skill in the art would appreciate. FIG. 6A shows first link member 560, second link member 563, and third link member 565 in an extended position (such that arm 530 extends outward from base 510). In this extended position, second link member 563 is pivotable relative to first link member 560 around first joint 570, while the first link member 560 is fixed relative to the base 510. Second link member 563 is pivotable relative to third link member 565 around second joint 573. Due to the pivoting movement of first, second, and third link members 560, 563, 565 about the first and second joints 570, 573, the arm 530 may assume a variety of positions. Reference is made to FIG. 5B showing an example of an orientation of the link members at different rotational positions about the first and second joints 570, 573. The first and second joints 570, 573 may be modest friction joints to hold positions once moved, but easy enough to pivot by a user wanting to move the arm to differing configurations. In an exemplary embodiment the range of motion about the joint axes can be about +/−180 degrees or more. In an embodiments, one or more of the joints can comprise a shaft attached to an end of a link, e.g., second link 563, extending vertically; one or both of the adjoining link(s), e.g., the first link 560 and the third link 565, include rolling bearings secured between a vertical bore formed in the link and a cap, with a hole in the cap for one end of the shaft to protrude.

Each of the first and second joints 570, 573 can alternatively have locking features (not shown) to separately lock into place in order to separately lock the position of first, second, and third link members 560, 563, 565, relative to the adjoining link(s) and/or base 510. Thus, for example, first joint 570 may be locked in order to lock first link member 560 in a first position while second link member 563 may pivot relative to first link member 560.

In some embodiments of a locking feature, the first link member 560 may include a horizontally pivotable lever that extends into and engages a detent formed in the base 510 when the first link member 560 is fully extended from the base 510 and the second link member 563 is rotated away from the folded, stow position. Rotating the second link member 563 from the folded position relative to the first link member 560 releases the lever and permits it to engage into the detent in the base 510, thus locking the first link member 560 in place relative to the base 510. Depressing the exposed end of the lever, either manually or by returning the second link member 563 to the folded position relative to the first link member, pivots the other end of the lever out of the detent, thus unlocking the first link member 560 from the base 510.

In some embodiments, a hard stop feature is included, that is only activated when the arm link members are deployed and the sterile drape is attached. Such a hard stop feature may prevent the second link member 563 from rotating back toward the stowed (fully folded) position more than 90 degrees relative to the first link member 560 (see FIG. 6E). A hard stop feature may minimize accidental breach of sterility if the medical device holder is moved toward the side of the base 510 or if the second link member 563 is moved to the stowed position. A hard stop feature also may prevent deactivation of the first link member detent, described above, which keeps the first link member 560 in the extended position during use.

When first, second, and third link members 560, 563, 565 are fully extended, arm 530 can have an overall length ranging from about 20 inches (50.8 cm) to about 40 inches (101.6 cm), for example about 30 inches (76.2 cm) to about 35 inches (88.9 cm). Such an extension length may allow arm 530 to extend a sufficient distance from the base 510, which may be located in a nonsterile field, to position an attached medical device holder safely within the sterile, surgical field. Thus, such an extension length may allow arm 530 to freely move within the sterile field, providing workflow flexibility to the user, while maintaining an adequate distance from the nonsterile environment, thus protecting the sterile environment from the nonsterile environment.

FIGS. 6B and 6C illustrate an exemplary process of moving arm 530 from the retracted position (FIG. 6C) to a partially extended position (FIG. 6B) to allow further positioning of the arm 530 relative to the base 510, such as in a fully extending position shown in FIG. 6A. In order to maneuver arm 530, first link member 560 can be moveably coupled to, for example, a slide rail 210 connected to the base 510. The moveable coupling allows the first link member 560 to translate, e.g., slide, relative to the base 510 and to be moved away from the base 510 as shown in FIG. 6B. By way of a non-limiting example, a bearing block 567 may be mounted to the first link member 560, e.g., to a top surface of the link member, which contains ball bearings (not illustrated). The bearings roll against the rail 210, portions of which extend through the bearing block 567, and other portions of the rail 210 are mounted to the base 510 to provide low friction linear motion with high stiffness in the other directions. However, other couplings are envisioned that can provide translational movement of the first link member 560 relative to the base 510, with the sliding rail being a non-limiting embodiment. In other embodiments, the entire arm 530 could be pivoted and pitched down from a vertical orientation to a final extended horizontal position, or yawed horizontally 90 degrees to the final position, or may include a four-bar linkage in the place of the linear slide rail described above.

In the embodiment shown, the base 510 includes a compartment 512 in which the arm 530, when in the folded configuration, can be housed when the arm 530 is in the retracted position (FIG. 6C). To slide the arm 530, the distal end of the third link member 565 can be pulled, causing the first link member 560 to slide along the slide rail 210 in the direction 514 from the configuration in FIG. 6C to that in FIG. 6B. The arm 530 generally can move to the position in FIG. 6B while in the folded configuration. Thus, FIGS. 6B and 6C illustrate a folded configuration in which the arm 530 can move in translation relative to the base 510. FIG. 6C illustrates a fully retracted configuration such that first joint 570 is disposed within base 510. FIG. 6B illustrates a partially extended position such that first joint 570 and second joint 573 are in a position to allow unfolding of the first, second, and third link members 560, 563, 565 relative to each other, for example, in the embodiment shown the first and second joints 570, 573 are disposed exterior of base 510. In the partially extended position, a proximal end portion of first link member 560 may still be disposed within base 510.

As shown in FIGS. 6A-6C, arm 530 includes a handle 590 or other grasping mechanism that can be used to allow a user to pull the arm 530 in direction 514. In some embodiments, handle 590 may be disposed on third link member 565. It is also contemplated that the movement of first link member 560 from the first retracted position of FIG. 6C to the partially extended position of FIG. 6B can occur in an automated manner, rather than manually, such as via motors driving the movement of the first link member 560 along the slide rail 210 or via another motor-driven movement mechanism (e.g., worm gear etc.). In that case, handle 590 may be provided to override a malfunction of such automated movement.

During the extension process of arm 530, and once first link member 560 has assumed the partially extended position of FIG. 6B and the second link member 563 has been partially rotated relative to the first link member 560 to engage the locking lever (discussed above), the first link member 560 may be locked into position to keep from translating along the slide rail 210 and back to the retracted position of FIG. 6C. Such locking also can prevent first link member 560 from moving horizontally or vertically relative to base 510 until arm 530 is in the extended position.

To further extend the arm from the partially extended position of FIG. 6B to the fully extended position of FIG. 6A, the third link member 565 can continued to be pulled in the direction of extension, which begins to cause the second link 563 member to rotate about first joint 570 so that second link member 563 becomes unfolded from first link member 560. Simultaneously or subsequent to the unfolding of second link member 563, the third link member 565 can be rotated about second joint 573 causing third link member 565 to unfold relative to second link member 563 so that third link member 565 becomes unfolded from second link member 563. Eventually, arm 530 can thus reach the fully extended configuration shown in FIG. 6A.

It is also noted that second link member 563 and third link member 565 need not be unfolded in order for arm 530 to assume the partially extended configuration, in which configuration the arm 530 can provide a sufficient distance into the sterile field as has been described above. In other embodiments, the arm 530 cannot be draped in a partially extended position, requiring the user to unfold the three link members to drape the arm 530. Once the arm 530 is draped, cable guide (discussed elsewhere herein) engage one or more hard stops that require a minimum angle, e.g., a 90-degree angle, between the first link member 560 and second link member 563 (as discussed elsewhere herein).

In order to move arm 530 from the extended position of FIG. 6A to the retracted position of FIG. 6C, the reverse order of operation as described above can occur. For example, third link member 565 can be pushed in a direction toward the base 510 and rotated to cause rotation of second link member 563 about first joint 570 in the opposite direction as the rotation in the unfolding step. Once fully folded, third link member 565 can continue to be moved toward the base 510, causing the eventual movement of the entire arm 530, in the folded configuration, along the rail 210 to the retracted position of FIG. 6C. As mentioned above, it is envisioned that any of the movements of the arm 530 can be automated using motors and controls.

Referring now to FIGS. 6D and 6E, the three-link jointed arm 530 holding a medical device holder 520, which in FIGS. 6D and 6E has an embodiment similar to that of FIGS. 2A-1 through 2A-5 but is not limited to such a configuration, is shown to illustrate a range of motion relative to an exemplary base 510. FIG. 6D shows the arm 530 in the fully extended configuration, as described above with reference to FIG. 6A. As depicted, with the attachment of the medical device holder 520 to the arm 530, a considerable reach into the sterile field from the base 510 can be achieved. From such a position, FIG. 6E further illustrates how the second link member 563 can be rotated to roughly 90 degrees relative to the first link member 560 about first joint 570, and the third link member 565 can in turn be rotated about 90 degrees relative to the second link member 563 about second joint 573 to move the arm 530 and the medical device holder 520 generally away from the surgical field and tucked back, yet outside of the base 510. Such an arrangement again can provide ease of use of the entire system before, during, and after a surgical procedure to provide a range of stable motion of the medical device holder in positions both within the sterile field and outside of it. The further incorporation of one or more hard stops (discussed above), which can be activated when a drape is installed, enforces the rotational placement of the link members into a configuration that helps avoid contact between the sterile medical device holder 520 and the non-sterile cart or base 510. Additional rotary range-of-motion hard stops may enforce arm positions toward the side of the cart opposite to that illustrated in FIG. 6E, which may minimize the chance of breech of sterility in the extreme position of FIG. 6E.

In the embodiment of FIGS. 6A-6E, the arm 530 shows link members 560, 563, 565 as having central longitudinal axes that remain generally parallel to each other. Additionally, the central longitudinal axis of second link member 563 is disposed below the central longitudinal axis of first link member 560 and of third link member 565 in order to provide a greater degree of motion to arm 530 and to allow arm 530 to be stored in the retracted position within base 510. In some embodiments, the central longitudinal axis of first link member 560 and of third link member 565 may be coplanar and remain at the same height regardless of the pivoting orientation of first, second, and third link members 560, 563, 565.

Figure 7:
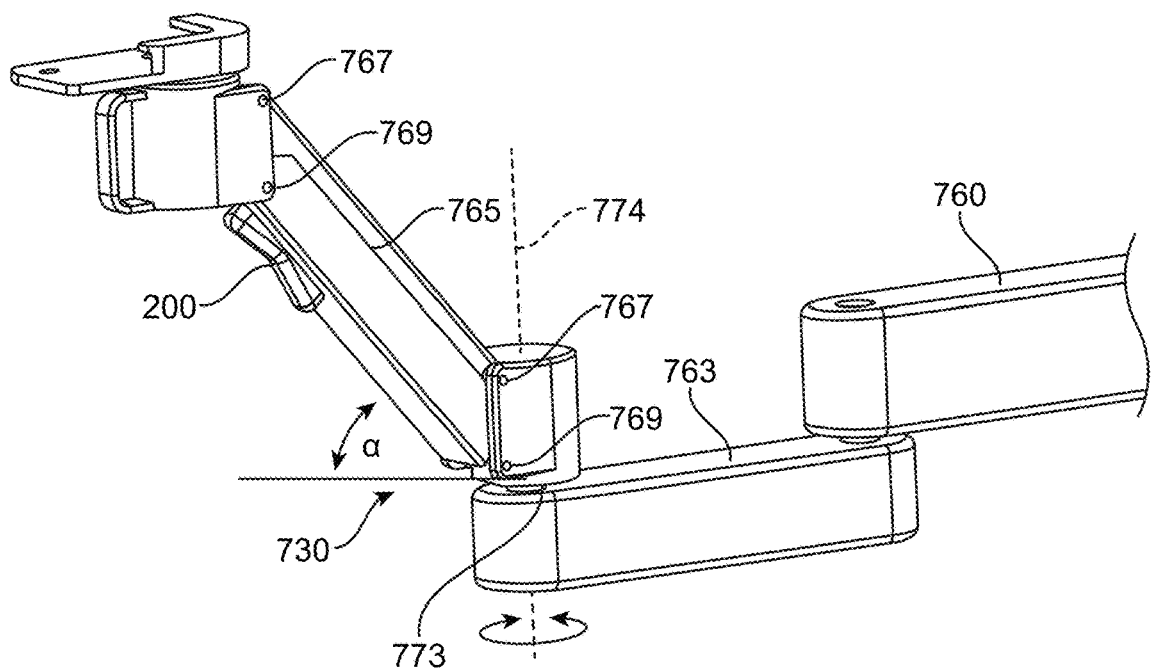
FIG. 7 shows distal portions of an exemplary embodiment of an arm in a raised configuration in accordance with the present disclosure.

In various embodiments, it may be desirable to allow additional movements of an arm, to further customize and add position and orientation flexibility of a medical device holder. FIG. 7 illustrates another embodiment of an arm having a three link jointed configuration. Specifically, FIG. 7 illustrates an arm 730, which may be used as the arm 30. The arm 730 has a first link member 760, a second link member 763, and a third link member 765, similar to the arm 530 described with reference to FIGS. 6A-6E. In addition, the arm 730 further includes a coupling of the third link member 765 (that can be a parallelogram linkage structure) that allows the third link member 765 to not only rotate around the joint 773 (i.e., around axis of rotation 774), but also to move up and down over an angle $\alpha$ between a position in which the longitudinal axis of the third link member 765 is generally parallel to that of the second link member 763 and a position in which the longitudinal axis of the third link member 765 is angled relative to the longitudinal axis of the second link member 763. More specifically, the third link member 765 may be moved from a first parallelogram orientation to a second parallelogram orientation which is different from the first parallelogram orientation. The first parallelogram orientation may be a rectangular orientation of the third link member 765, and the second parallelogram orientation may be non-rectangular. The parallelogram linkage can permit this movement without altering an orientation of the distal end of the arm 730 so as to maintain the medical device holder (not shown) in a generally planar orientation (e.g., the surface generally parallel to the ground) as the distal end of the third link member 765 moves vertically. The range of motion of the vertical movement of the third link member 765 can range from +/−5 inches (12.7 cm) to −+/−10 inches (25.4 cm), for example about +/−8 in (20.3 cm), measured as movement of the distal end of the third link member 765. In other words, the third link member 765, in addition to being rotatable about axis 774 via joint 773, can rotate through angle $\alpha$. By way of a non-limiting example, a four-bar linkage may be part of, or used as, third link member 765. In such an embodiment, an upper link of third link member 765 is attached at both ends via pins 767 and can pivot around plain bearings to rotary joint housings, and a bottom link, parallel to the top link, of third link member 765 is also attached to and can pivot about the rotary joint housings via pins 769. If the distance between pins 767, 769 is the same in both housings, and the length of the top and bottom links are equal, the medical device holder (not shown) will remain parallel to the ground. In some embodiments, the range of angle $\alpha$ is +/−40 degrees, but other values for the range of this angle may also be used.

Arm 730 also can include a motor to move third link member 765 vertically to the position generally parallel to second link member 763 through the range of angular motion denoted by angle $\alpha$. The motor may be disposed on arm 730, or arm 730 may be remotely connected to the motor. For example, a DC brush motor may be operably connected to cause the angular motion of the third link member 765. A vertical motion switch 200 may be accessed by a user in order to activate the motor to move, for example, third link member 765 from the horizontal position to the inclined position illustrated in FIG. 7. Switch 200 may be operably coupled to the motor and can be disposed on arm 730. Alternatively (not shown), a switch may be provided on a portion of the medical device holder and configured to be operably coupled to a motor that raises the third link member 765.

In yet other embodiments, it is envisioned that the entire arm 30 can have a limited range of vertical movement over an angle relative to the base. This can be useful, for example, if a patient bed were to raise up and hit the arm and/or if the medical device holder were to get caught under something or a force applied from above. Configuring the arm to allow some tolerance in movement vertically can enhance overall stability of the system in various potential use conditions.

Some embodiments may include a mechanism which permits a limited range of vertical movement of the arm over an angle relative to the base. By way of a non-limiting example, one such mechanism may include a yoke having a horizontally oriented bore. The yoke is attached to the bearing block, e.g., bearing block 567, which cooperates with the linear slide rail 210, discussed above with reference to FIGS. 6A-6C. The proximal end of the first link member is pivotably connected to the yoke, instead of being rigidly connected to the bearing block, by a horizontal pin so that the first link member can rotate in a pitch direction with respect to the bearing block and, therefore, relative to the base, but is constrained in all other directions. The first link member is counterbalanced or otherwise forced upward by a compression spring positioned on the proximal side of the yoke's pivot and held against a hard stop formed on the base. This allows movement of the arm downward against the force of the spring when excessive downward loads are applied to the medical device holder or to the arm. In some embodiments, a sensor may be provided to detect this movement and alert the user of the excessive load, e.g., by closing a circuit to sound a buzzer, energize a light, or the like. This could prevent overbalance of the base due to an operating room table moving down and making an undetected collision with the arm. In yet other embodiments, a weight may be used to counterbalance the arm in the place of or in addition to the compression spring. In other embodiments, a second pivot may be provided with a counterbalance at the proximal end of the arm to perform this same function for excessive loads that are applied upward.

In some embodiments, arm 30 may include a counterbalancing mechanism to offset any weight placed on arm 30. Thus, arm 30 may maintain its vertical position even when a weight is deposited on arm 30, for example, if a user were to lean on the top of arm 30. In some embodiments, arm 30 may be counterbalanced for about a 30 lb payload with the arm fully extended. In general terms, this payload must be large enough to not falsely trigger, but should be much lower than that needed to overbalance the cart or base. The load causing overbalance of the cart or base is dependent on the distance from the point of application of the load to the base, so the most extended orientation of the arm can be used to determine a payload above that which is normally anticipated and thus should be tolerated before movement of the arm relative to the base.

In some embodiments, arm 30 may include a back-drivable mechanism to inhibit, and may prevent, arm 30 from inadvertently moving horizontally. For example, arm 30 may be inhibited or prevented from moving horizontally if a user were to accidentally fall into arm 30. Such may inhibit or prevent arm 30 from inadvertently moving and causing medical instruments to fall off medical device holder 20. The back-drivable mechanism of arm 30 may be accomplished by the structures of the first and second joints 570, 573 for the various three link jointed arm embodiments described herein.

Figure 8:
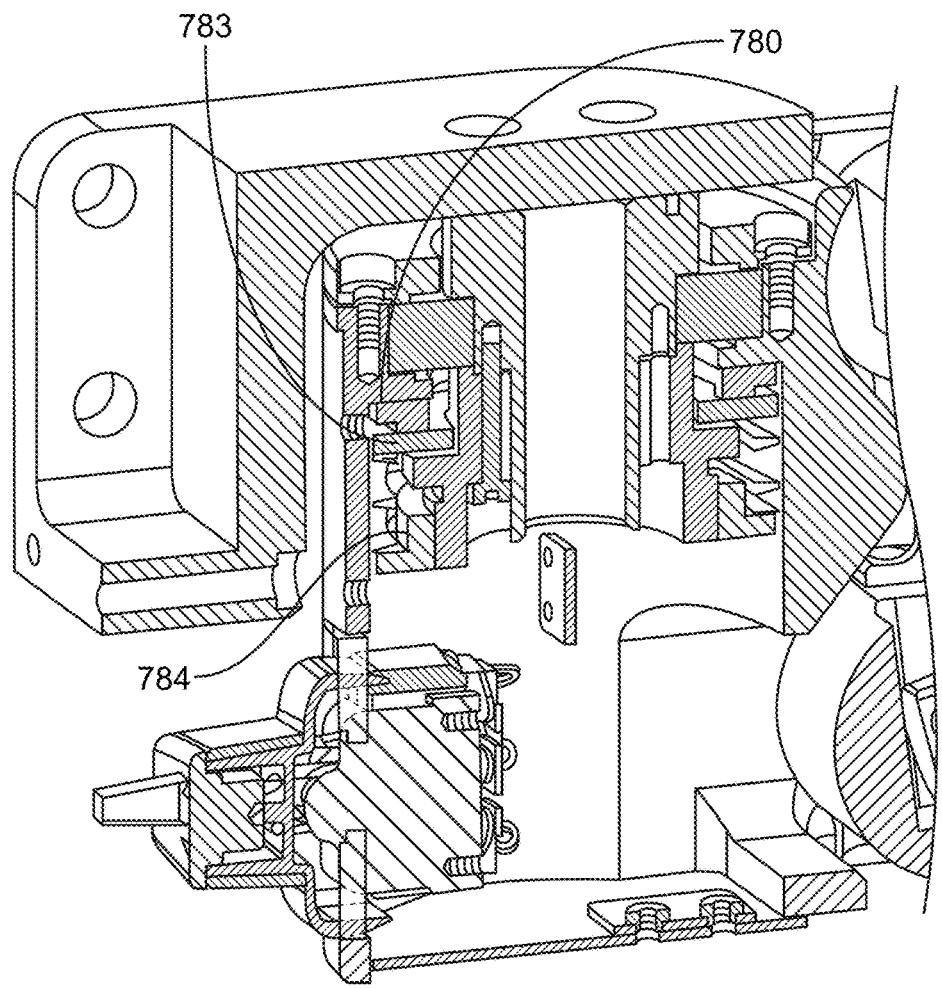
FIG. 8 shows a perspective, cross-sectional view of components of an exemplary joint for an arm in accordance with the present disclosure.

The couplings at the joints between the link members of the arm in various embodiments described herein can have a variety of features that permit smooth and controlled operation. It is desirable to have joint structures that allow for the medical device holder, and arm, to be relatively easily moved without drifting. For example, as shown in FIG. 8, the joint coupling can be a SCARA (Selective Compliance Assembly Robot Arm) joint that includes a friction or brake pad 780, a rotor, which may be single sided, 783, and a spring 784, which may be a wave spring. The brake pad 780 generates controlled rotational friction when pushed against the rotor 783 by the wave spring 784. Spring 784 allows the friction to be maintained at an approximately consistent level independent of brake pad wear. The brake pad 780 is fixed to one link member via fasteners, and the rotor 783 is constrained against rotation relative to the interfacing link member but can move axially toward and away from the brake pad to compensate for brake pad wear. In a non-limiting example, pins are provided in the link member which extend through corresponding mating holes in the rotor.

Figure 9A:
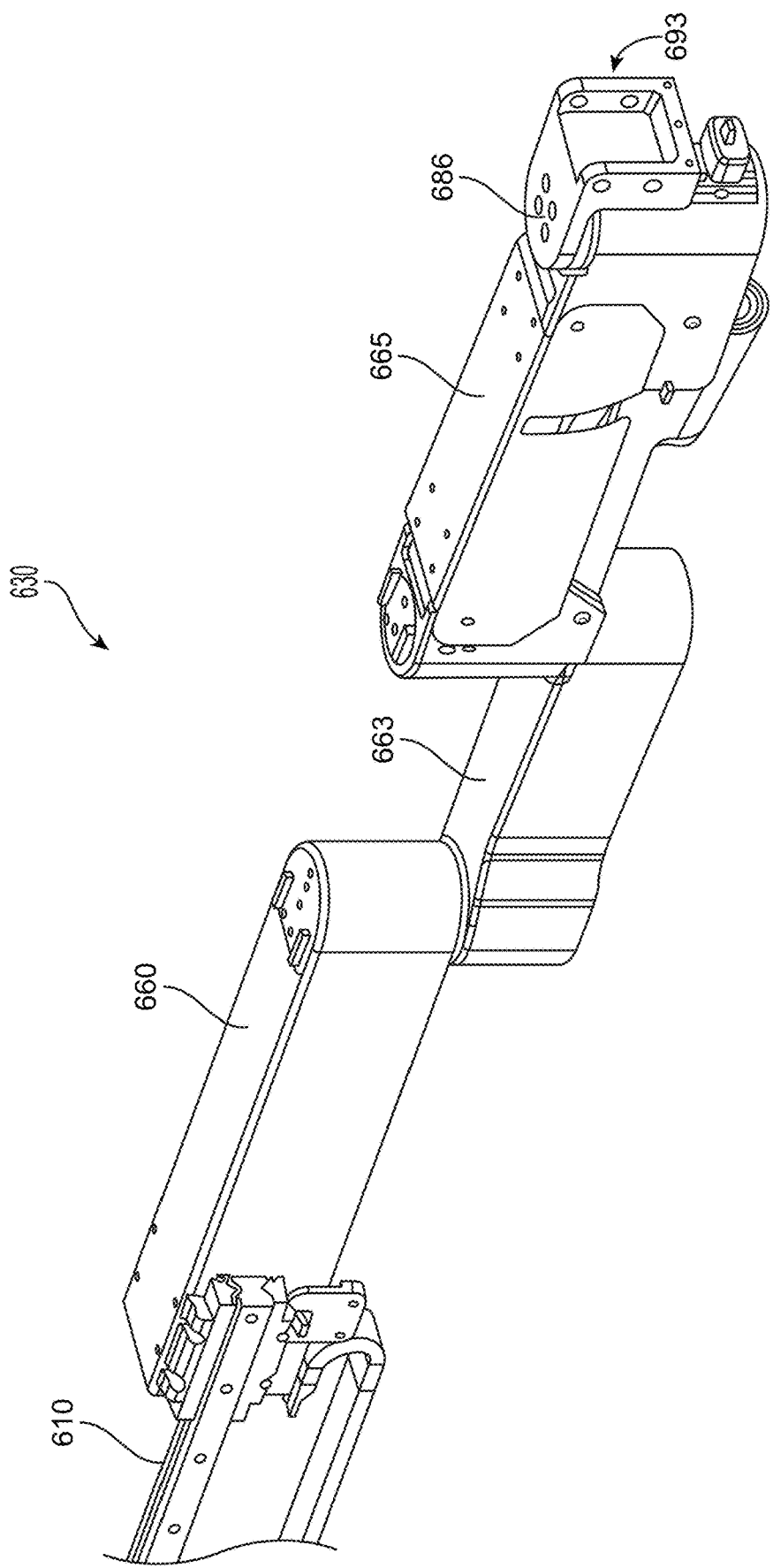
FIG. 9A shows a perspective view of another exemplary embodiment of an arm in an extended configuration in accordance with the present disclosure.

FIG. 9A depicts another exemplary embodiment of an arm having three link members coupled by joints in a manner similar to that described with respect to the embodiment of FIGS. 6A-6E. Specifically, FIG. 9A illustrates an arm 630, which may be used as the arm 30. In the embodiment of FIG. 9A, the first link member 660 attaches at a side of the link member 660, rather than its top, to a slide rail 610 to allow translational movement of the arm relative to the base (not shown). A breakaway mechanism (not shown) also can be provided between the first link member 660 and the bearing block mounting the first link member 660 to the slide rail 610. Also, the third link member 665, having the parallelogram linkage 695, can include a back-drivable lead screw (not shown) to provide protection against overload of the arm by payload of the medical device holder and/or lifting of the arm from the underside, such as by a patient or operating table being lifted into the medical device holder or arm from underneath. In some embodiments, backdriving may be achieved by providing a lead screw and a mating lead nut, with the lead nut including ball bearings to create a low friction interface with the lead screw. Varying the pitch and motor friction to rotate freely upon exertion of a specific axial load allows backdriving.

Figure 9B:
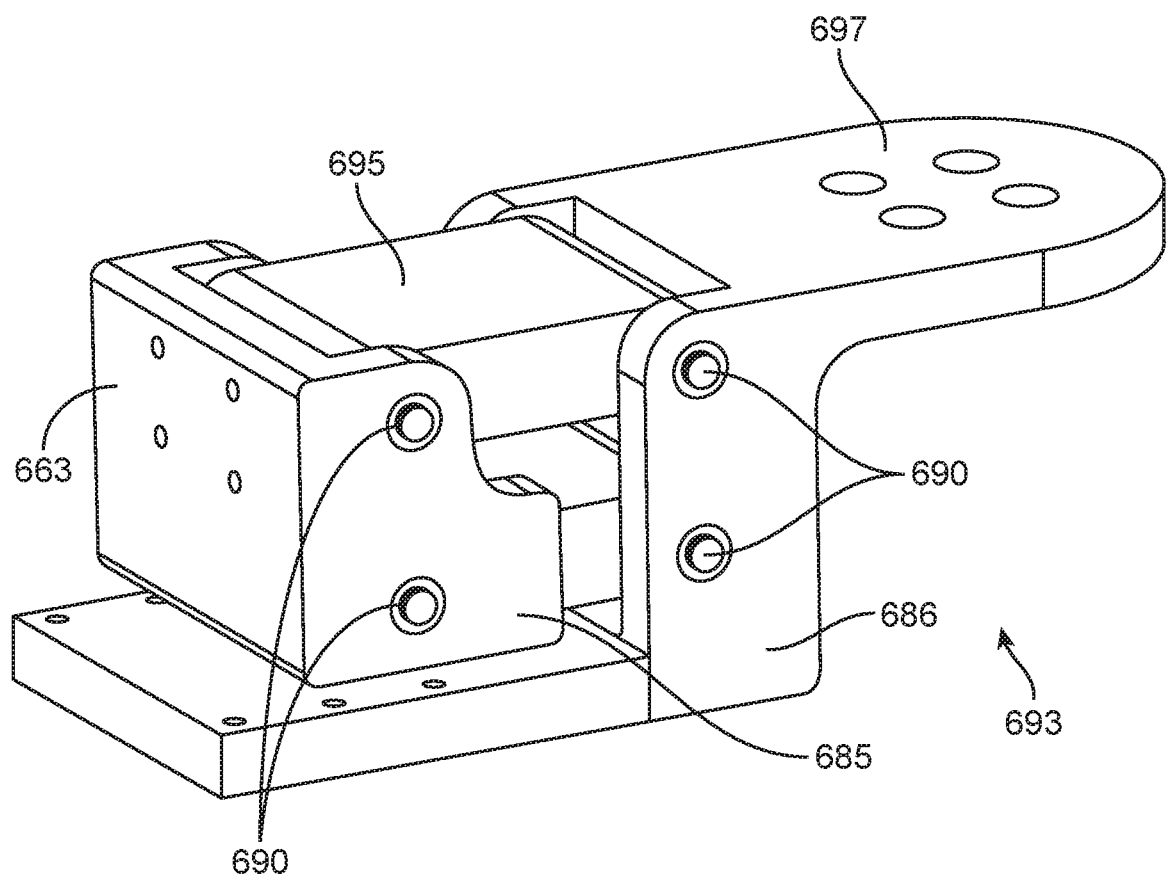
FIG. 9B shows a perspective view of a linkage of the arm of FIG. 9A in accordance with the present disclosure.

Further, in the embodiment of FIG. 9A, and with additional reference to FIG. 9B, it is contemplated that the medical device holder can be coupled to the distal end of the arm 630 via a connecting member 693 that serves as a floating "hand" to permit vertical movement of the medical device holder relative to the second link member 663 while the medical device holder remains horizontal, that is, level with the floor. This may be useful in situations where the patient or operating table rises up to place a significant force under the medical device holder, or if the user inadvertently moves the device holder downward into the patient by activating the motor. The connecting member shown in FIG. 9B includes a first member 685 connected to a second member 686 via needle bearings 690. A parallelogram linkage 695 connects first member 685 to second member 686 in order to provide a range of motion of about 30 mm to about 45 mm between the first and second members 685, 686. Second member 686 may be mounted and attached to arm 630, for example at the distal end joint of the arm 630 at laterally extending flange 697, and first member 685 can be attached to medical device holder (not shown). This can allow the connecting member 693 and medical device holder to pivot around the joint at the end of the arm 630. Parallelogram linkage 695 provides a connection between first and second members 685, 686 in order to connect arm 630 with medical device holder 520 (not shown). In some embodiments, the connecting member 693 can be a sterile adapter member that attaches a medical device holder to the arm, for example, in an embodiment in which the tray is a sterile tray as discussed above. In this manner, the connecting member 693 constrains the link members to only move vertically and remain level.

In an embodiment, a portion of the connecting member 693 can be a contact switch. In this way, if something, such as a patient on an operating table or part of the table is under the medical device holder and comes into contact with the connecting member 693, the action of the parallelogram linkage 695 can be actuated to slightly lift the medical device holder upwardly relative to the arm in a gentle controlled motion to avoid damage to sensitive components of the arm or to the patient. In an exemplary embodiment, the connecting member 693 can be designed to move once a payload of the entire medical device holder and its devices supported thereon is on the patient. The parallelogram linkage 695 is passive and thus can be moved at any speed. In an embodiment, however, the vertical movement permitted by the parallelogram linkage 695 is from 30 mm-45 mm of travel in about 1-1.5 seconds.

In various exemplary embodiments, arms (such as any of the arms 30, 530, 630, and 730) may be made relatively lightweight so that the maximum payload is a predetermined amount, about 90 N in an exemplary embodiment, including the weight of medical device holder 20. Further, one or more joints may include a breakaway mechanism. The coupling mechanisms between an arm and a base also may allow for the arm to be provided as field-replaceable units.

An arm 30 in accordance with various exemplary embodiments disclosed herein may also include one or more sensors to monitor the position of arm 30, as well as various automated control features to permit adjustments or movements of the arm and/or medical device holder so as to provide enhanced safety.

Figures 1, 10A:
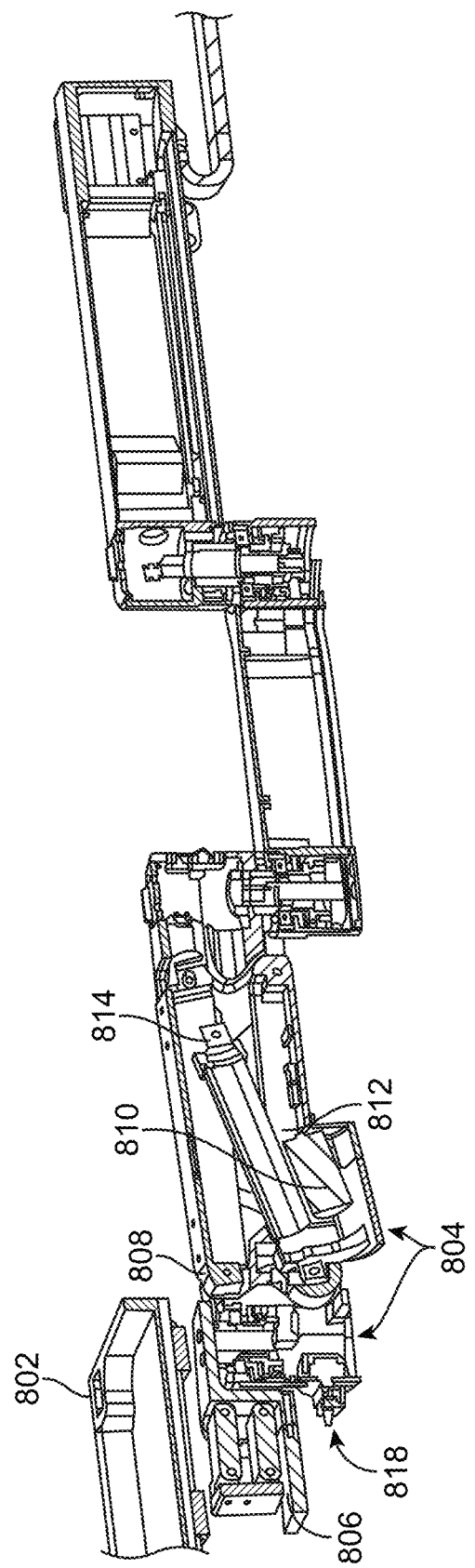
Figures 2, 10A:
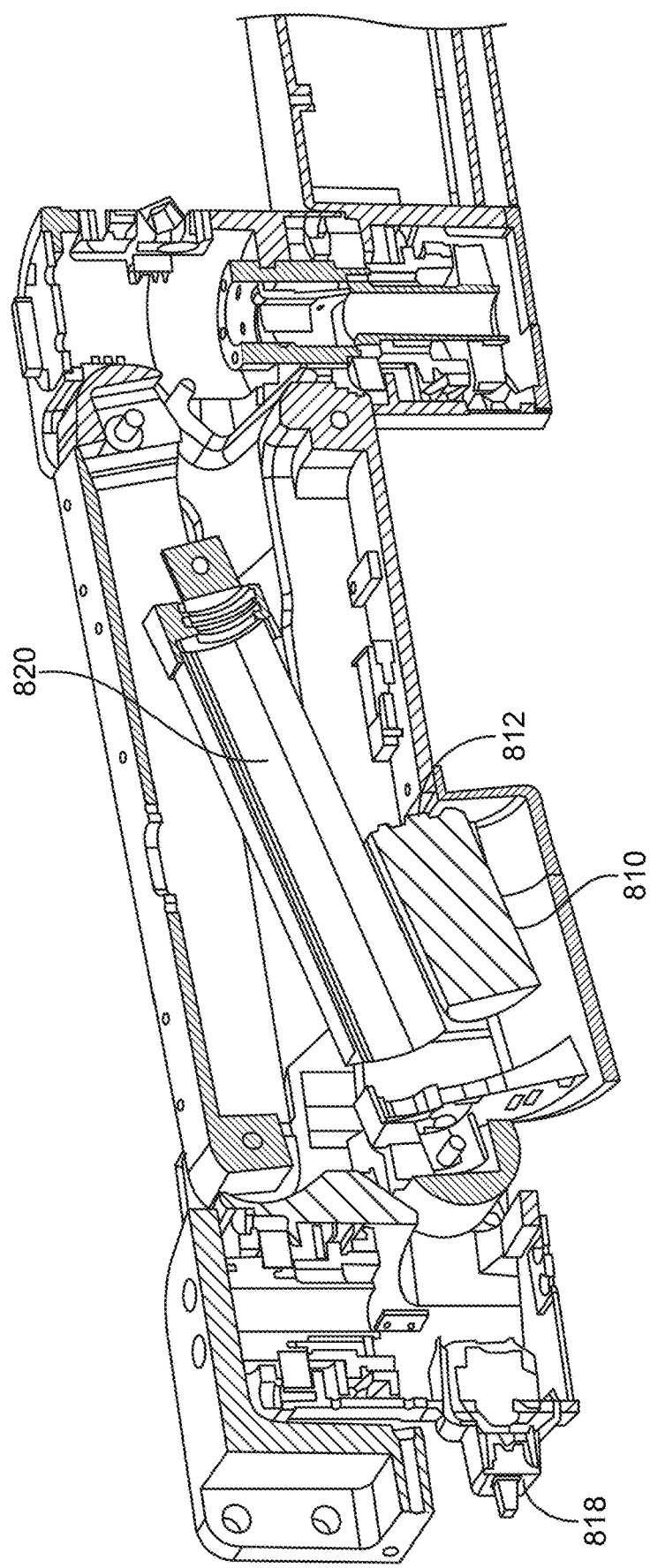
Figures 3, 10A:
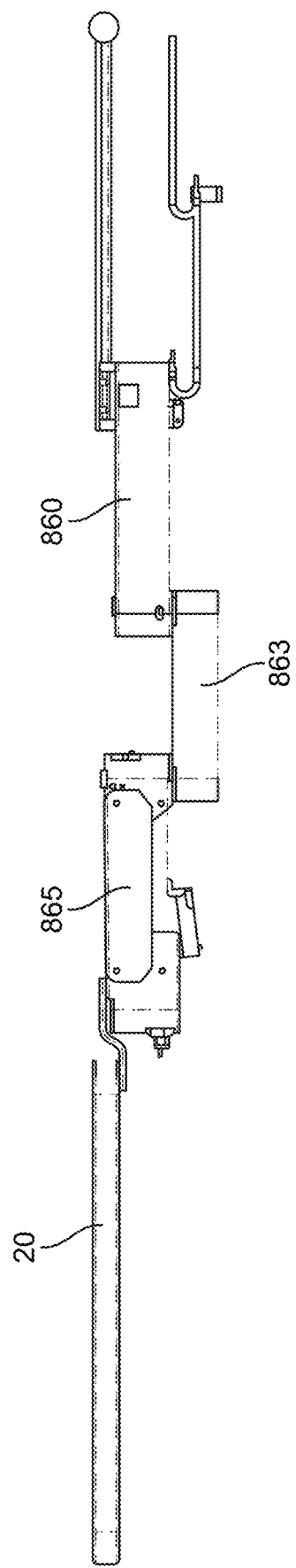

Arm 30 may include various electronics components. For example, FIGS. 10A-1 to 10A-3 illustrate an embodiment of an arm 830, which may be used as the arm 30. As shown in FIG. 10A-3, the arm 830 comprises a first link member 860, a second link member 863, and a third link member 665 coupled together by joints, similar to the embodiment of FIG. 9A. The arm 830 comprises various electronics components. Such electronic components may include a stow momentary switch 802, which may be disposed underneath the drape when the drape is placed over the arm. The electronic components may also include contact switches to detect contact between various portions of the arm, medical device holder, and external objects. For example, contact switch 804 may be located on the underside of the wrist and parallelogram to detect contact between the underside of the medical device holder and distal portion of the arm. A contact switch 806 may be located to detect contact between the arm or medical device holder and an external object. Other components include an LED 808 for notification of contact with the underside of the medical device holder and/or distal portion of the arm with an external object, such as a patient, a DC brush motor 810 (low duty cycle, low usage), an electronic brake 812 at the motor (normally on), an absolute position sensor 814, and additional switches for tray position and/or drape presence.

More specifically and with continued reference to FIGS. 10A-1 and 10A-2, in some embodiments a stow momentary switch 802 includes a snap-action micro-switch that is triggered only when the medical device holder is fully extended, and is used to prevent motorized vertical movement that could cause collisions and damage between the third link member and the holder. Concerning the switches for detecting contact between the underside of the holder and the distal portion and the arm, a most distal switch 806 is positioned at the floating hand (described above) and is positioned to detect contact between the holder and an object. The next two contact switches 804 are positioned to detect contact between distal portions of the arm that could come into the sterile field. The LED 808 lights up to alert the user of contact with the underside of the holder and distal arm, as discussed above. The DC brush motor is an example of any motor 810 that is suitable to adjust vertical position of the holder; a DC brush motor may be advantageous because of its simplicity of control and low cost, as precision control is not needed. An electronic brake 812 prevents backdriving of the lead screw 820 and inadvertent vertical movement; however, the brake can optionally be tuned to allow backdriving at a specific load. An absolute position sensor 814 measures the vertical location of the holder, as the holder must be in a center vertical position for the link members to fold without contacting each other. A Z-axis adjustment switch 818, positioned anywhere on the arm, but advantageously near the distal end of the arm, e.g., at the end of the third link member, may be a Hall-effect switch to activate motor 810. Activation of motor 810 causes the motor 810 to rotate the lead screw 820 in its lead nut (not illustrated), thus causing the four-bar linkage of the third link member to change shape and thereby raise the third link member into the angled orientation described herein, e.g., with reference to FIG. 7, and thus raise the medical device holder 20 upwardly.

Arm 30 may, in some embodiments, also includes one or more additional components which may inhibit or prevent patient harm due to contact with the underside of the holder, including: a counterbalance for a flip-up arm, torque sensors, kick panels/switch array, proximity sensors, and counterbalance wrist and tray in Z-axis parallelogram. Additionally, arm 30 may include a hard stop and a pivot point counterbalance. More specifically, if provided, a torque sensor could measure patient load, output of which may be used to autonomously drive the arm out of the way using a motor. A kick panel switch array is positioned to recognize any contact with an object, such as with the patient, any may need to cover every surface of the holder. As with the torque sensor, its output may be used to autonomously drive the arm out of the way using a motor. Proximity sensors can be implemented to detect when was an object is near the sensor and thus their outputs may be used to set off an indicator (e.g., an alarm), move the arm, or both, and may have to cover all surfaces of the holder and have to 'see' through the drape. A counterbalanced wrist and tray in a Z parallelogram involves providing a counterbalance within the most distal (third) link member so that it would act like the floating hand, which may warrant precise friction control of back-driving the lead screw.

Figures 2, 10B:
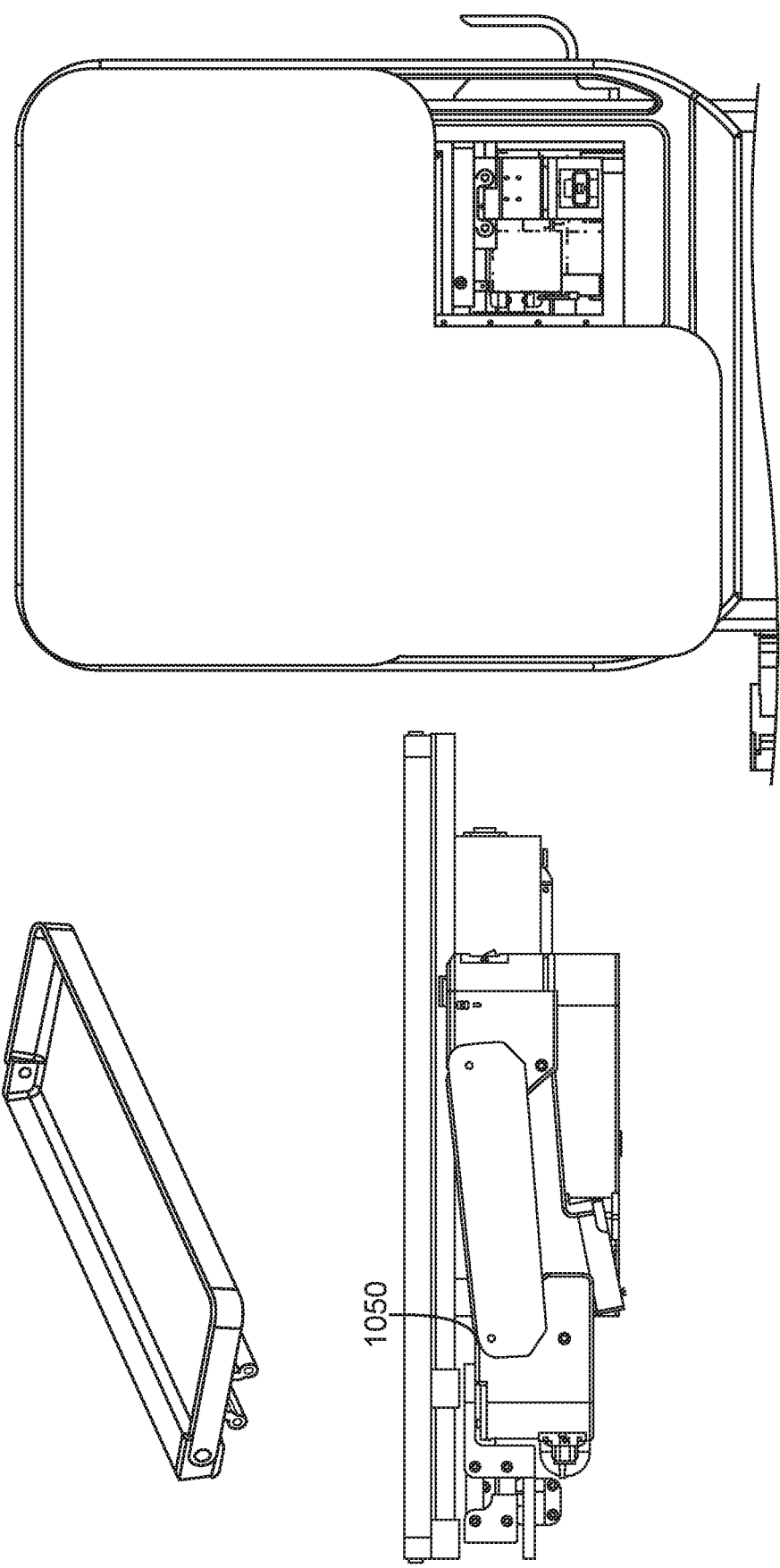
Figures 3, 10B:
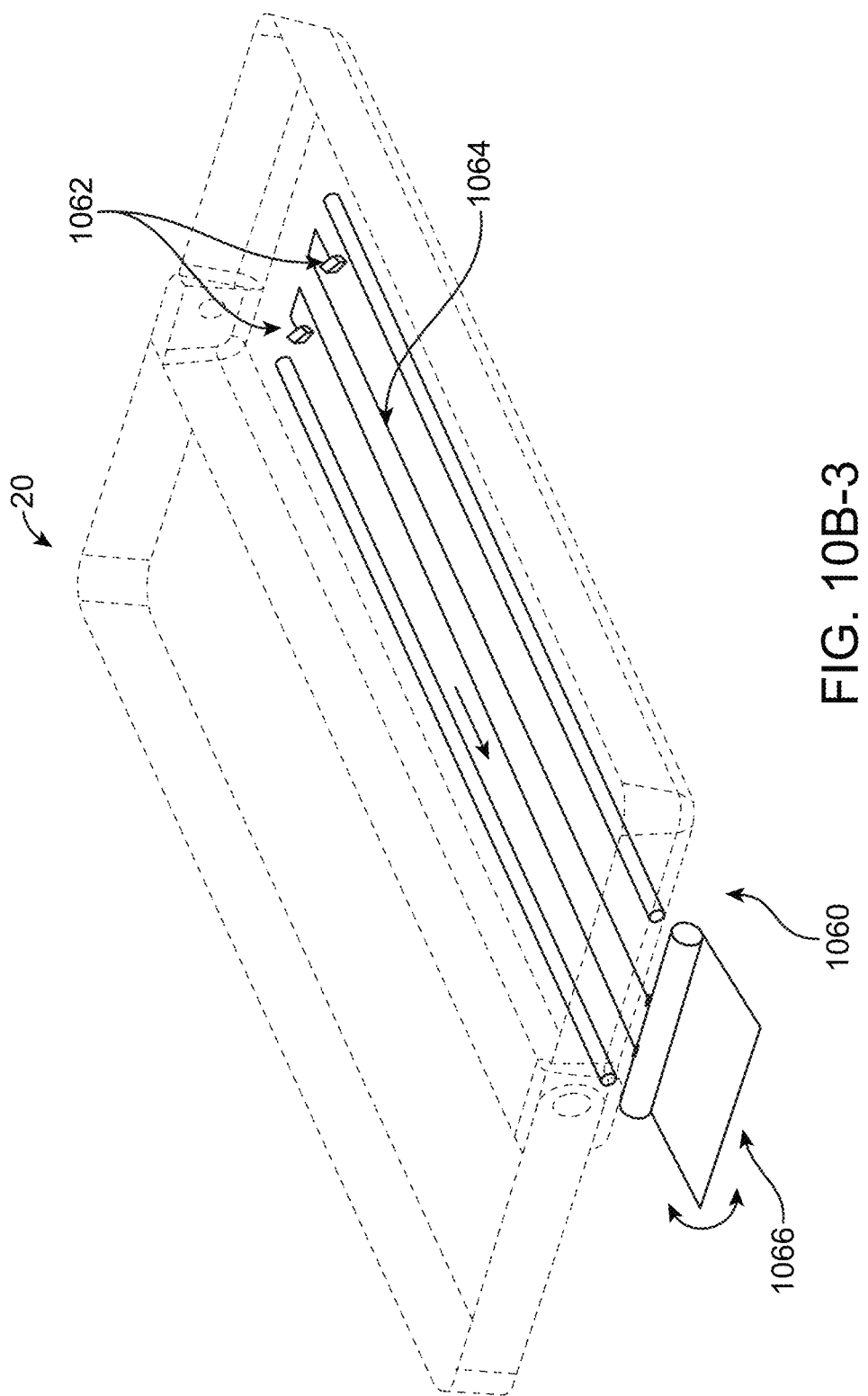

In some embodiments, medical device holder 20 may be attached to and stored with arm 30 in the retracted configuration. In such a configuration, the medical device holder 20 may be intended to be reused and provided with a sterile drape, rather than sterilized for each use. For example, FIGS. 10B-1 and 10B-2 illustrate an embodiment of a medical device holder 1020, which may be used as the medical device holder 20, coupled to an embodiment of an arm 1030, which may be used as the arm 30. As shown in FIGS. 10B-1 and 10B-2, a medical device holder 1020 can be coupled to arm 1030 along a linear guide rail system 1050 to allow the medical device holder 1020 to be slid back over the arm 1030 such that the arm 1030, along with the medical device holder 1020, can have a compact, retracted configuration suitable for storage, such as within a base 10 as has been described above with respect to the arm 30. In some embodiments, a linear guide rail system 1050 may include a guide rail with two shafts mounted to the bottom of the medical device holder 1020 along its entire length. A bearing block (not visible in FIGS. 10B-1 and 10B-2), is attached to the arm 1030, and the medical device holder 1020 slides linearly on the shafts with respect to the fixed bearing block. In the embodiment of FIGS. 10B-1 and 10B-2, the medical device holder 1020 has the configuration as in FIGS. 2A-2 and is shown in the folded configuration.

As shown in FIGS. 10B-1 and 10B-2, linear rail system 1050 couples the medical device holder 1020 to arm 1030. Thus, the medical device holder 1020 can slide along rail system 1050 from a first distal position to a second proximal position, such that the second proximal position places the medical device holder over a length of the arm 1030 in the folded configuration. In one embodiment, a handle (not shown) can be provided to manually push or pull medical device holder 1020 relative to arm 1030.

With reference to FIG. 10B-3, another embodiment is illustrated. A medical device holder 20, shown in broken lines, may include a z-axis control lever 1060 to activate position sensor switches 1062 located at the distal rotary joint of the arm via pushrods 1064. The pushrods 1064, located under the medical device holder 20, are connected to a rotatable handle 1066. Rotation of the handle 1066 moves the pushrods proximally and distally, causing proximal portions of the pushrods to actuate switches 1062, the outputs of which may be used to activate a motor, such as motor 810. Inclusion of z-axis control lever 1060 may eliminate the need for any electrical control wires on the medical device holder 20 and the subsequent need for a rolling wire loop which may take up extra volume. Alternatively, a direct connector may be provided between a lever and the sensor(s), with a rolling loop for the wires using a segmented energy chain to control the flexing of the wires.

In yet additional embodiments, a mechanism is included which ensures that the medical device holder 20 is fully extended upon arm deployment. This may assist to both prevent collision with the third link member when it is moved vertically by the motor, and also to allow rotational movement of the medical device holder without damaging an installed drape. Such a mechanism may be positioned just above the linear rail (e.g., 210) in the base (e.g., 510). The medical device holder 20 is raised and lowered with respect to the most distal rotary arm joint, depending on the deployment position. When retracted, the medical device holder 20 is lifted up using the floating hand parallelogram linkage by contact with a sliding cam surface fixed to the base. Starting from the fully retracted position within the base (reference being made to FIGS. 6A-6C), the following sequence occurs. The first link member is locked into the base by the detent, as described above. Pulling on the distal end of the medical device holder results in the holder sliding on its linear slide until it is fully extended, at which time the cam surface on the base allows the medical device holder to move down and drop into a recess formed in the most distal rotary link member, thereby locking the holder in a fully extended position. This action trips a lever attached to the base that releases the first link member and allows the entire arm to slide out of the base. Once the arm is out of the base, continued pulling on the medical device holder results in unfolding of the second link, as described above. After a small amount of unfolding, the lever that is contained within the first link member (also described above) becomes locked into the base, preventing the first link member from retracting into the base. Continued unfolding then can occur to prepare the arm for draping, including unfolding the trough bar of the holder.

Retracting the arm is the reverse of the foregoing, once the motorized parallelogram is made level. This may be enforced by user-messaging based on the z-axis parallelogram position sensors and the drape presence sensor.

Figure 11A:
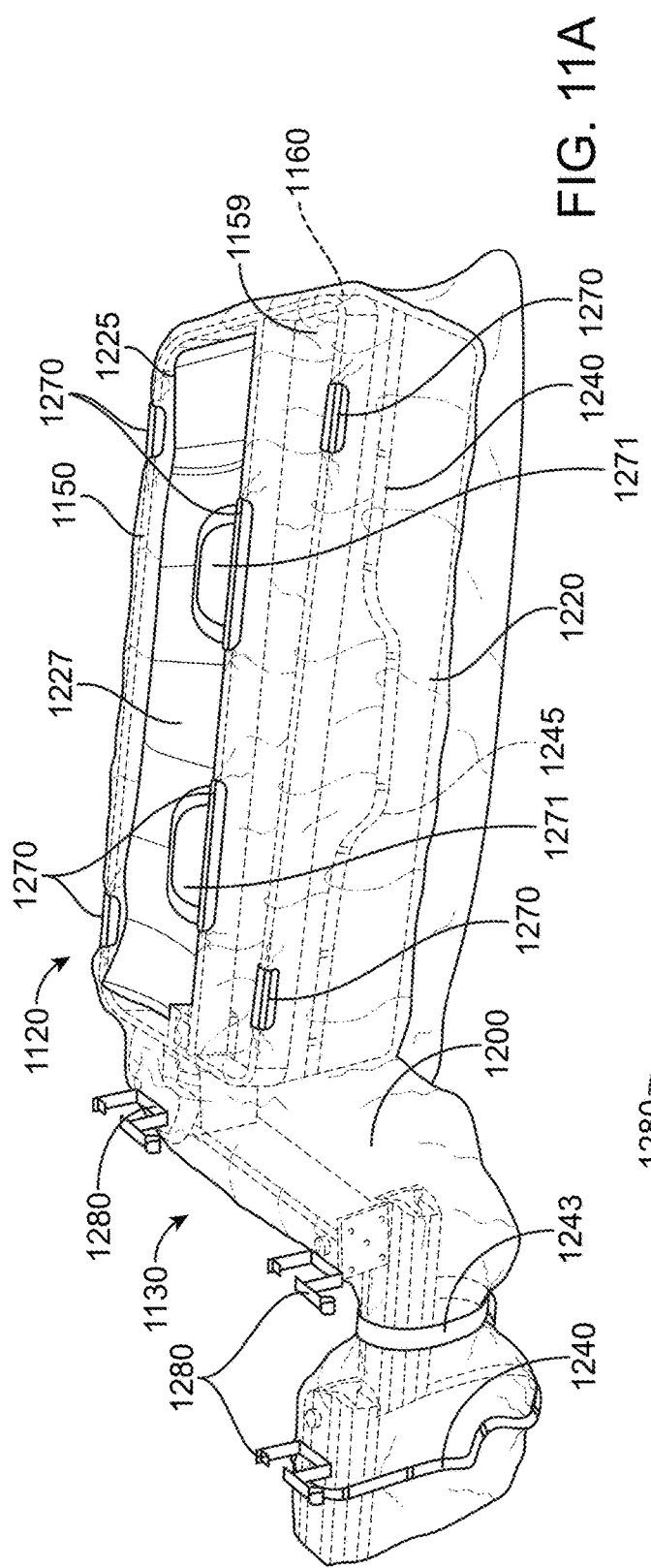
FIGS. 11A and 11B show perspective views of exemplary embodiments of various arms, holders, and drapes in accordance with the present disclosure.

Arms 30 in accordance with various exemplary embodiments also may have various transmission line routing features disposed along the arm or attachable thereto so that such transmission lines can be routed along an entire length of the arm in an organized manner from surgical instruments on the medical device 20 holder to auxiliary function supply equipment. For example, the various hooks, such as the hook described with reference to FIG. 4, cable guides, clips, and other mechanisms that can support and route transmission lines can be attached to the arm. Moreover, as shown in the embodiment of FIGS. 11A and 11E, described further below, an arm 30 in accordance with the present disclosure can have receiving features that allow sterile transmission line routing structures to be removably received within the arm, such as at the locations of the joints where link members of the arms are coupled together. The arm can directly receive such members, or they can be provided as part of sterile draping that is intended to be placed over the arm, which will be described in more detail below. In an exemplary embodiment, each link member is approximately 2.75 inches wide×3 inches tall. First link member may be 10 inches long, second link member may be 9.5 inches long, and third link member may be 14 inches long, with a joint diameter of 2.75 inches. Link lengths may be optimized so that proper extension into the sterile field can be obtained, and that the arm may be folded into the base cavity without contacting the side of the cavity and without protruding excessively out of the base.

Figure 17:
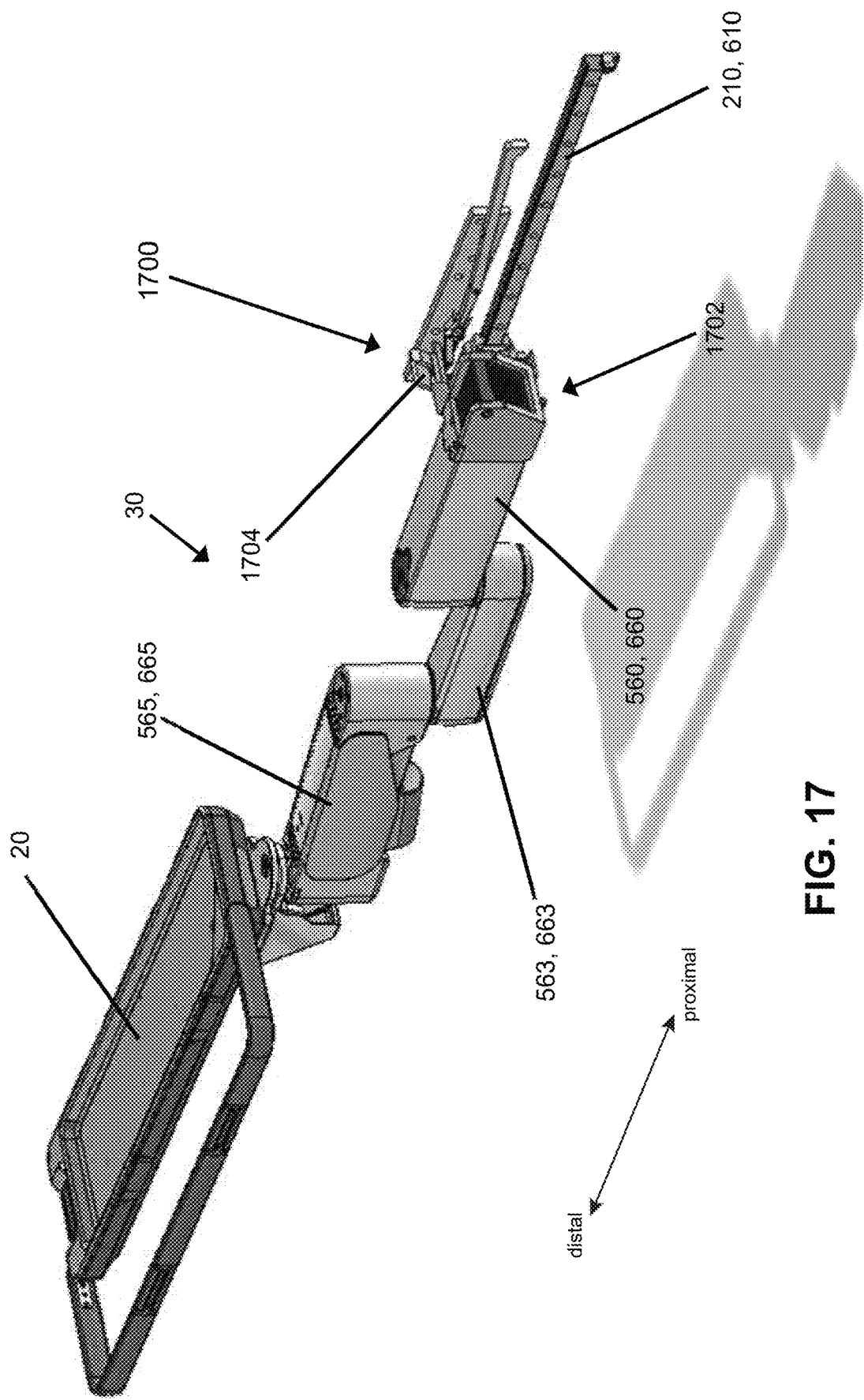
FIG. 17 shows a perspective view of another exemplary embodiment of an arm and medical device holder including exemplary locking and breakaway mechanisms.

FIGS. 17-26 illustrates yet further embodiments of various mechanisms that can be included in or used in conjunction with embodiments of the arm 30. In FIGS. 17-26, an embodiment of the arm 30 that has three link members is illustrated, and various parts of the arm 30 are referred to using references numbers that were used above in relation to similar parts of the arms 530 and 630. FIG. 17 shows an exemplary embodiment of a locking mechanism 1700. In general terms, a locking mechanism, as described herein, is provided for staged deployment of an arm 30. More specifically, a locking mechanism 1700 controls the motion of the link members of the arm 30 relative to each other, and to the base, from a folder, stowed configuration when pulling on an end of the medical device holder 20. According to one embodiment, the medical device holder 20 may first slide out, then the first link member 560, 660 is allowed to deploy by sliding on rail 210, 610. Then the links are permitted to pivot and deploy until in a fully extended configuration, such as that illustrated in FIG. 17.

With continued reference to FIG. 17, an arm 30 includes a first link member 560, 660, a second link member 563, 663, and a third link member 565, 665. A medical device holder 20 is attached to the distal end of the arm 30, and more specifically to the distal end of the third link member 565, 665. FIG. 17 also illustrates an exemplary embodiment of a breakaway mechanism 1702, as well as the rail 210, 610. Breakaway mechanism 1702 is described in greater detail below.

Figure 18:
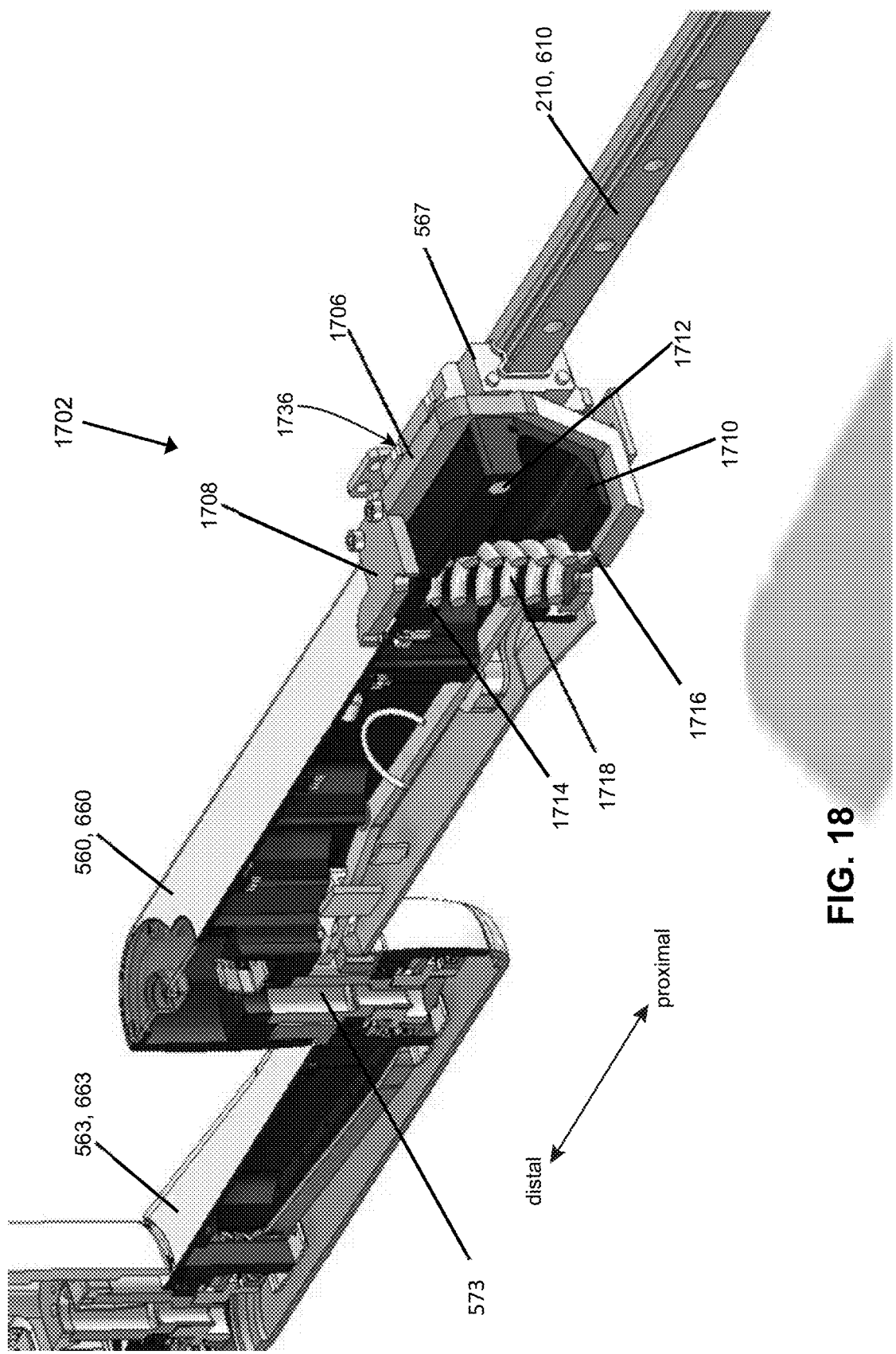
FIG. 18 shows a cross-sectional view, with portions broken away, of an exemplary embodiment of a breakaway mechanism.

FIG. 18 illustrates a sectional view, with portions broken away, of a first link member 560, 660, joined with a second link member 563, 663, at a rotatable joint 573. With continued reference to FIG. 18, an exemplary embodiment of the breakaway mechanism 1702 is illustrated. The breakaway mechanism 1702 includes a structural yoke 1706 which at least partially surrounds the proximal end portion 1710 of the first link member 560, 660, and which is mounted to the bearing block 567. The yoke 1706 may be attached to the proximal end portion 1710 at a pivot pin 1712 so that the yoke and proximal end portion 1710 can pivot relative to each other. A recess 1714 is formed on an inner surface of the proximal end portion 1710 and a vertically aligned recess 1716 is formed on the oppositely facing inner surface of the yoke 1706. A spring 1718, which may be a coil spring, a set of stacked disc or wave springs, or the like, has a preselected spring force, for reasons described elsewhere herein. The spring 1718 is positioned between the recess 1714 and the recess 1716, by which spring preloads the entire arm 30 up against a hard stop 1708. As the yoke 1706 is biased against the proximal end portion 1710, both can pivot relative to each other about pivot pin 1712 against the force of the spring 1718. The hard stop 1708 is attached to or formed with upper portions of the yoke 1706, so that the range of rotary motion of the first link member 560, 660 relative to the yoke 1706 is limited in one direction. FIG. 18 also illustrates the bearing block 567 interacting with the rail 210, 610 as described elsewhere herein.

Bearing block 567 may include one or more notches or recesses 1736 on a top surface thereof, for reasons that will be described in greater detail elsewhere here in. Hard stop 1708 may take a number of different forms, with the exemplary embodiment of FIG. 18 being a plate attached to the yoke 1706 adjacent to the upper surface of the link 560, 660. In this manner, if the arm 30 is overloaded, e.g., is leaned on by a practitioner, the arm 30 can deflect downwards against the force of the spring 1718, as the proximal end portion 1710 of the link 560, 660, rotates about the pivot pin 1712 relative to the yoke 1706. When the overload condition is removed, the force of the spring 1718 between the proximal end portion 1710 and the yoke 1706 forces the arm 30 to resume the configuration illustrated in FIG. 18 until it reaches hard stop 1708. Thus, a breakaway mechanism as described herein may inhibit or prevent overbalance due to vertical overloading of medical device holder 20 or arm 30. Optionally, a position sensor (not illustrated) may be mounted on the hard stop 1708, e.g., at the tip of hard stop, that detects when the hard stop is no longer in contact with the first line (i.e., an overload condition occurs), and thus the system can warn the user about potential overload/overbalance.

Figure 19:
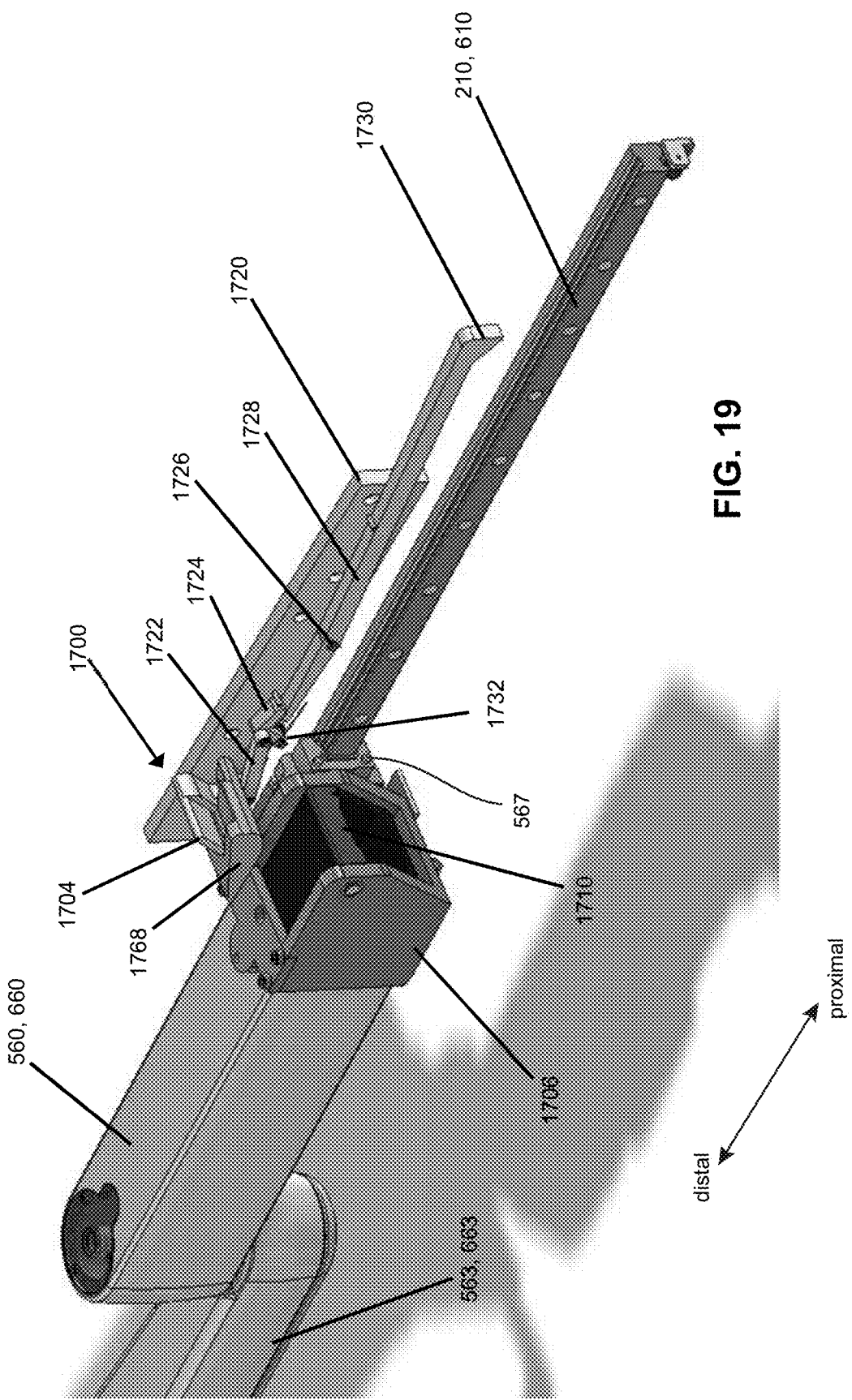
FIG. 19 shows a perspective of an exemplary embodiment of a locking mechanism.

Turning now to FIG. 19, an exemplary locking and deployment mechanism 1700 (also referred to herein as locking mechanism) is illustrated. The exemplary locking mechanism 1700 may include a first generally horizontally extending finger 1722 and a second generally horizontally extending finger 1724, which fingers are joined together at one or more pivots 1732. A spring may be employed at pivots 1732 to bias the first and second fingers 1722, 1724 into an unlocked or locked orientation, as will be described in greater detail elsewhere herein. The locking mechanism 1700 further includes a pivot pin 1726 about which a lock arm 1728, which extends generally longitudinally, is pivotally secured to a linkage support 1720 which in turn may be attached to the base 10. The lock arm 1728 includes at least one detent 1730 at or adjacent to a proximal end of the lock arm 1728, as illustrated in FIG. 19. According to further embodiments, the one or more springs which bias the lock arm 1728 and the fingers 1722, 1724 into a locked or unlocked configuration may be located at other positions in the locking mechanism 1700, such as acting directly between the lock arm 1728 and the support 1720, as will be readily apparent to those of ordinary skill in the art. FIG. 19 also illustrates a pivoting ramp 1704 which, when push by the medical device holder 20 as will be described elsewhere herein, pivots to engage distal portions of finger 1722 and thereby engage the locking mechanism 1700. A fixed ramp 1768 is fixedly positioned relative to the linkage support 1720, against which the pivoting ramp 1704 is hingedly attached so that it can pivot between the configuration of FIG. 19 and the configuration of FIG. 20, described in greater detail below. FIG. 19 also illustrates first link member 560, 660, second link member 563, 663, yoke 1706, end portion 1710 of the first link member, as well as rail 210, 610.

Figure 20:
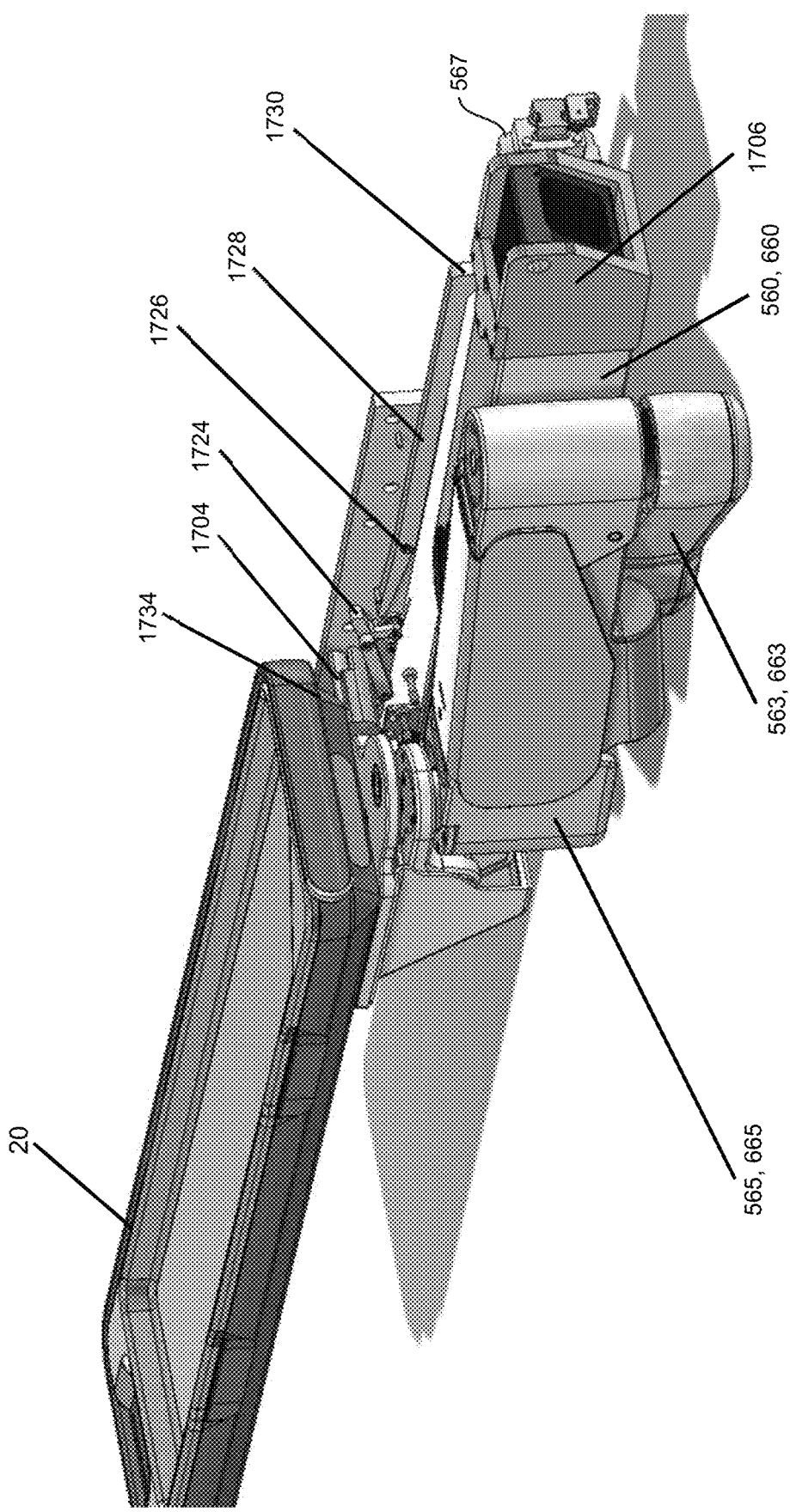
FIG. 20 shows another view of the embodiment of FIG. 19 in a folded configuration.

With the reference to FIG. 20, an exemplary arm 30 and medical device holder 20 are illustrated, with the arm in a folded configuration as similar to configurations described elsewhere herein. The arm 30 may include first link member 560, 660, second link member 563, 663, and third link member 565, 665. In the illustration of FIG. 20, the medical device holder 20 has been pushed back, that is, proximally, toward the yoke 1706, which causes a bottom surface 1734 of the medical device holder 20 to push against the pivoting ramp 1704 and push the pivoting ramp 1704 down. When the pivoting ramp 1704 is pushed down by the medical device holder 20, it rotates down relative to the fixed ramp 1768 and portions of the pivoting ramp 1704 push down against the distal portions of the first finger 1722. When the first finger 1722 is pushed down, because it is pivotally connected to the second finger 1724, the second finger 1724 pivots upwardly, allowing the lock arm 1728 to pivot about pivot 1726. When lock arm 1728 pivots upwardly, its proximal end, and more particularly the detent 1730, pivots downwardly and engages against the top surface of the bearing block 567, and more particularly into the notch or recess 1736. In this manner proximal motion of the medical device holder 20 relative to the arm 30 causes the mechanism to engage and inhibit or prevent first link member 560, 660, and therefor the entire arm 30, from further motion, which in turn permits medical device holder 20 to be further pushed proximally, as described in greater detail below.

FIG. 21 illustrates an exemplary embodiment arm 30 which includes an internal lock mechanism for the first link member 560, 660. The mechanism includes a striker block 1738 which is mounted to the base 10 and includes a recess therein oriented toward the first link member. A pivoting lock link 1740, which may be J- or L- or T-shaped, is mounted within the first link member 560, 660, and is actuatable between locked and unlocked positions, as described in greater detail below.

Figure 22:
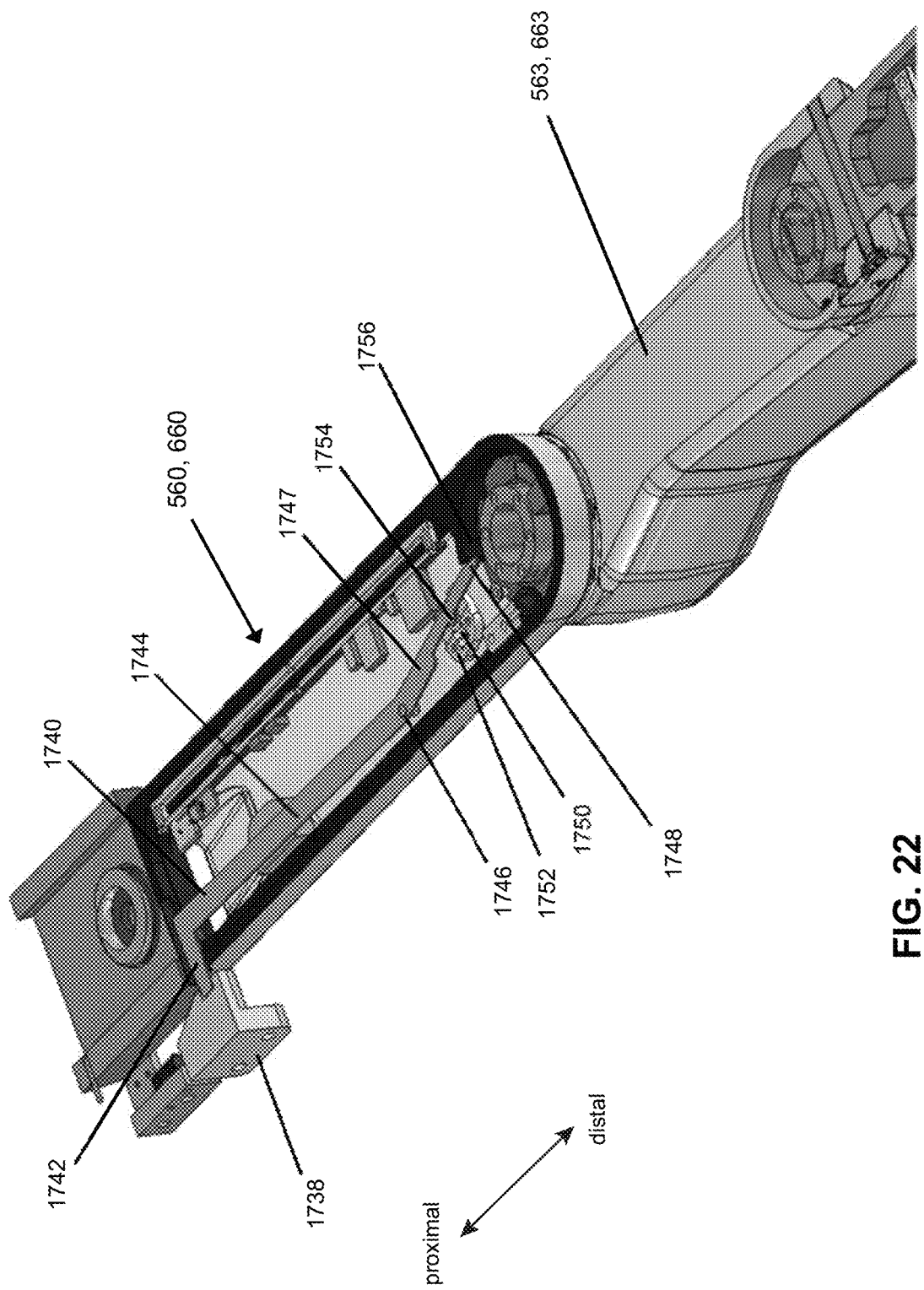
FIG. 22 shows a perspective view, with portions broken away, of the embodiment of FIG. 21.

With continued reference to FIG. 22, internal portions of first link member 560, 660, are illustrated. The locking link 1740 includes a latterly extending locking finger 1742, which extends through the body of the link member, and into the recess in the striker block 1738, thereby locking the link member 560, 660 from movement relative to the striker block 1738 and, therefore, relative to the base 10. The locking link 1740 may include a longitudinally extending arm 1744 which may be connected at a pivot pin 1746 to the link member 560, 660. Extending further distally from the pivot pin 1746, the locking link 1740 includes a distal portion 1747 which extends generally longitudinally toward the second link 563, 663. The distal portion 1747 is biased in one direction by a spring 1750 which may be housed in a recess in a block 1752, and the distal portion 1747 may include a detent 1754 to engage an end of the spring 1750 and thus retain the spring against the distal portion. A distal tip 1748 of the distal portion 1747 is located adjacent to a block, tab, or protuberance 1756 which is attached to or otherwise rotates with second link 563, 663.

Figure 23:
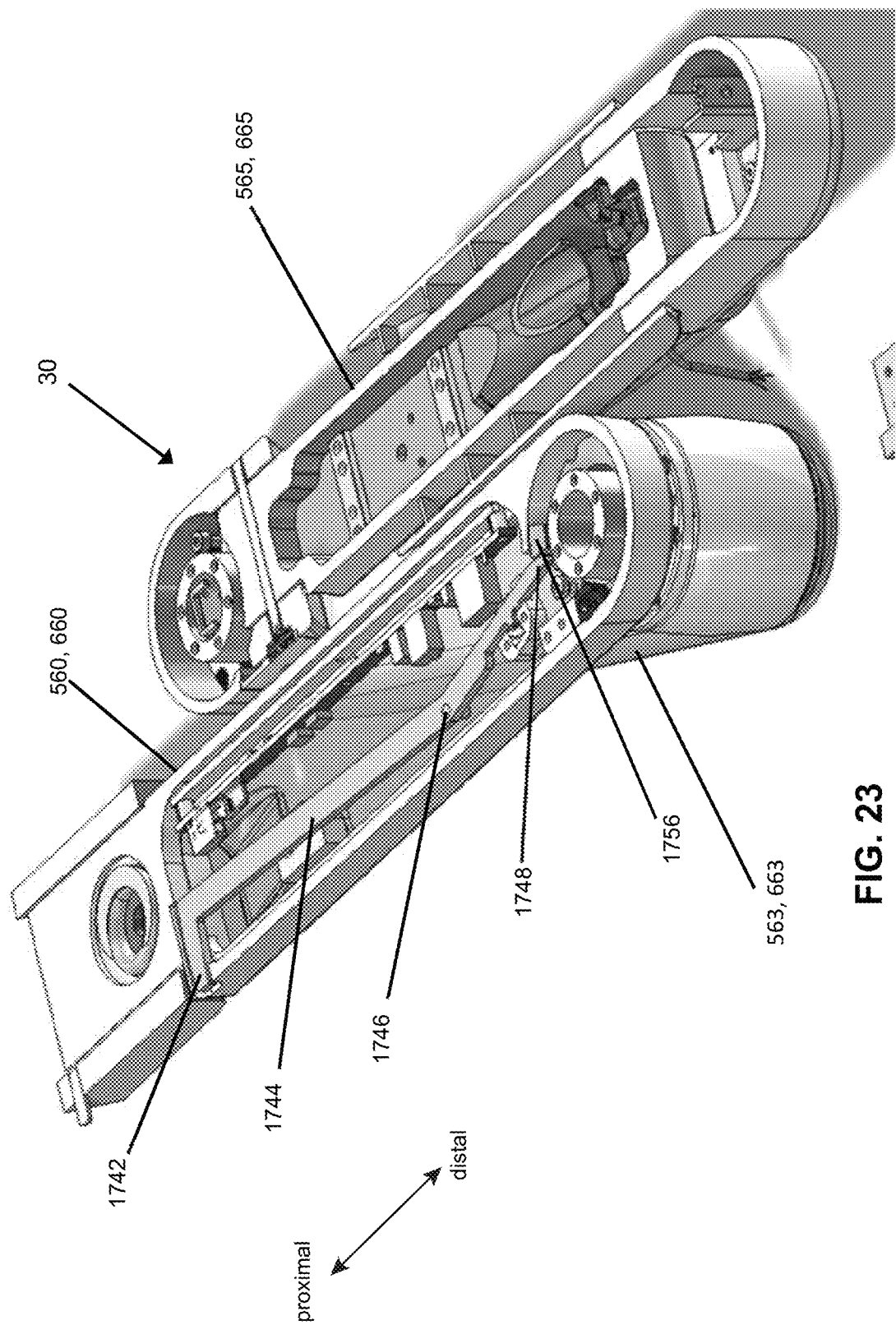
FIG. 23 shows a perspective view, with portions broken away, of the embodiment of FIG. 21 in an unlocked configuration.

With reference to FIG. 23, the arm 30 is shown in a folded configuration, as described elsewhere herein. As the second link 563, 663 rotates relative to the first link member 560, 660, the block 1756 moves relative to the first link member 560, 660, and engages against the distal tip 1748 of the locking link 1740. This causes the locking link 1740 to rotate about pivot 1746, causing the laterally extending locking finger 1742 to move out of the recess in the striker block 1738, and thus unlock the link member 560, 660 and allow it to slide longitudinally along the rail 210, 610.

Figure 24:
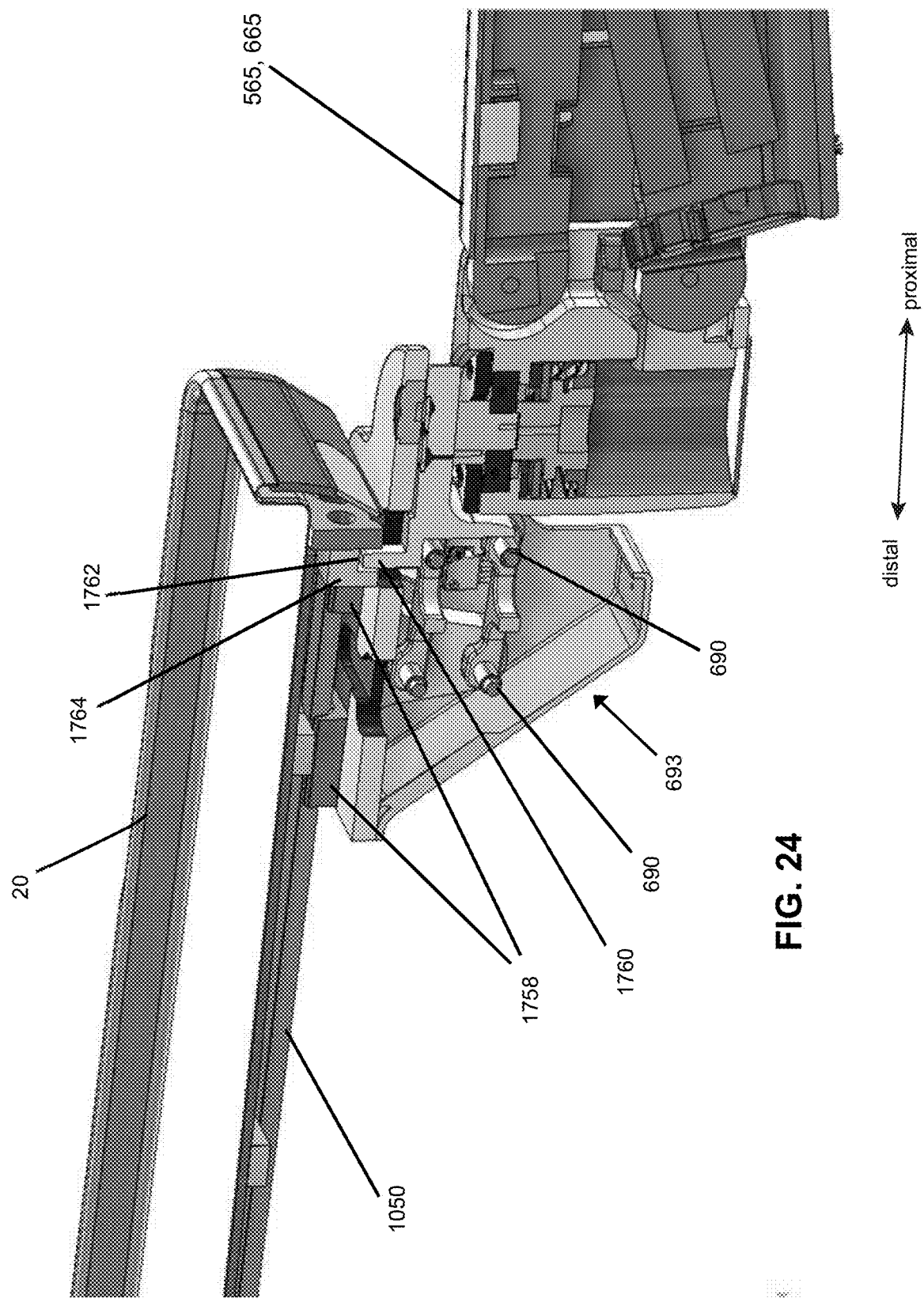
FIG. 24 shows a perspective view, with portions broken away, of an exemplary embodiment of a medical device holder locking mechanism.
Figure 25:
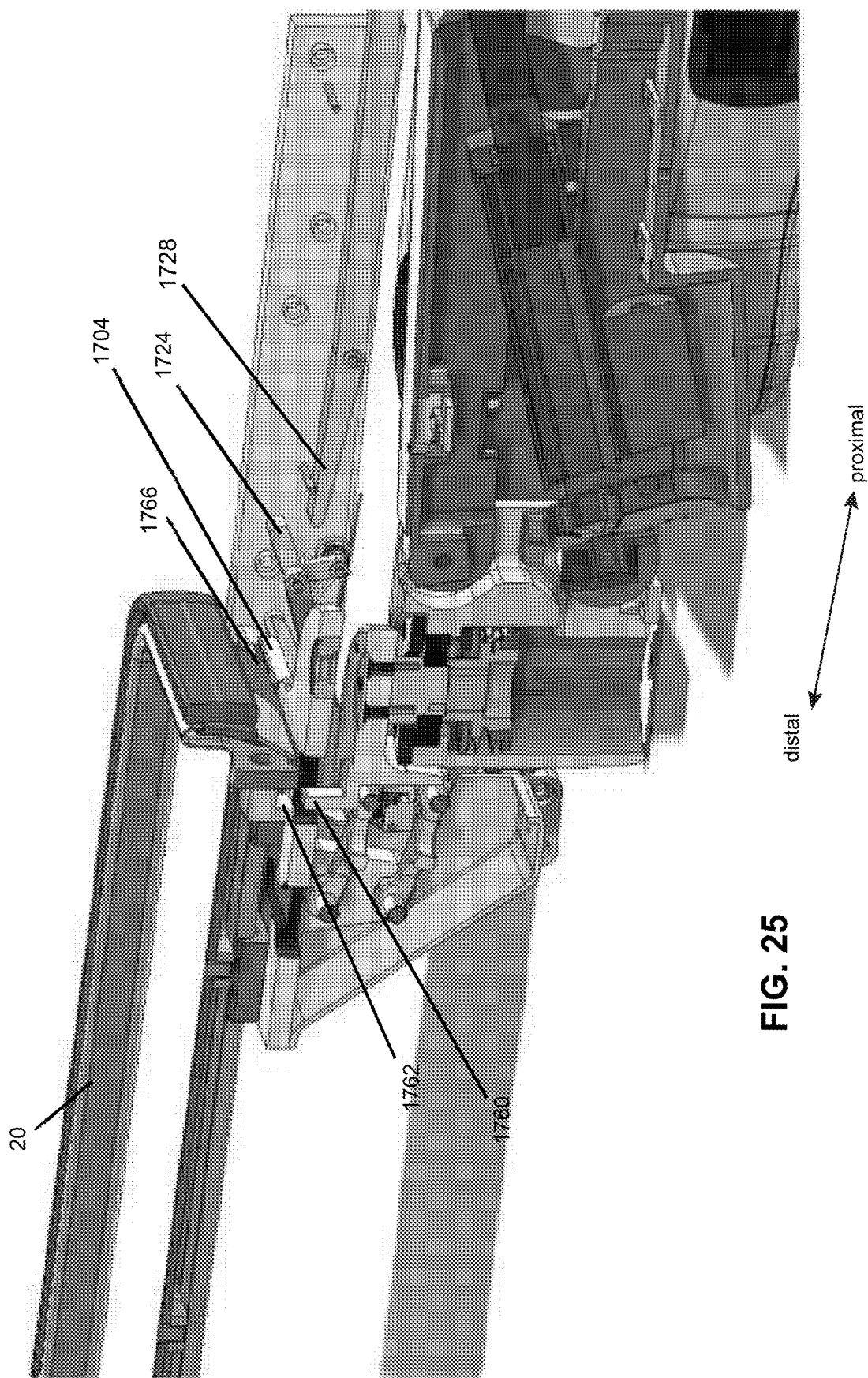
FIG. 25 shows a perspective view, with portions broken away, of the embodiment of FIG. 24 in an unlocked configuration.

FIG. 24 illustrates yet further embodiments. The medical device holder 20 may include rails 1050 which may be received in rail blocks 1758 mounted to the connecting member 693. As described elsewhere herein, the connecting member 693 includes pivots (i.e., via needle bearings 690) which permit the connecting member 693 to tilt upward. A block 1764 is attached to the connecting member 693 and may include a recess 1762 in which a finger 1760 extends and prevents the tray from moving proximally or distally relative to the connecting member. The finger 1760 is fixedly attached to the third link member 565, 665. With reference to FIG. 25, the medical device holder 20 has moved proximally relative to the third link member 565, 665 (as illustrated in FIG. 24), and a proximal portion 1766 of the tray has engaged the pivoting ramp 1704 and has pushed the pivoting ramp 1704 to rotate downward relative to the fixed ramp 1768. The proximal portion 1766 of the medical device holder 20 is caused to move upward as it engages against the fixed ramp 1768, causing the finger 1760 to no longer be held in the recess 1762, and thus permits medical device holder 20 to continue to be pushed proximally (that is, to the right in FIG. 25), because the finger 1760 no longer locks the medical device holder 20 at recess 1762. This proximal motion of the medical device holder 20, as discussed elsewhere herein, also causes the lock arm 1728 and finger 1724 to pivot and lock the arm 30 to the bearing block 567.

Figure 26:
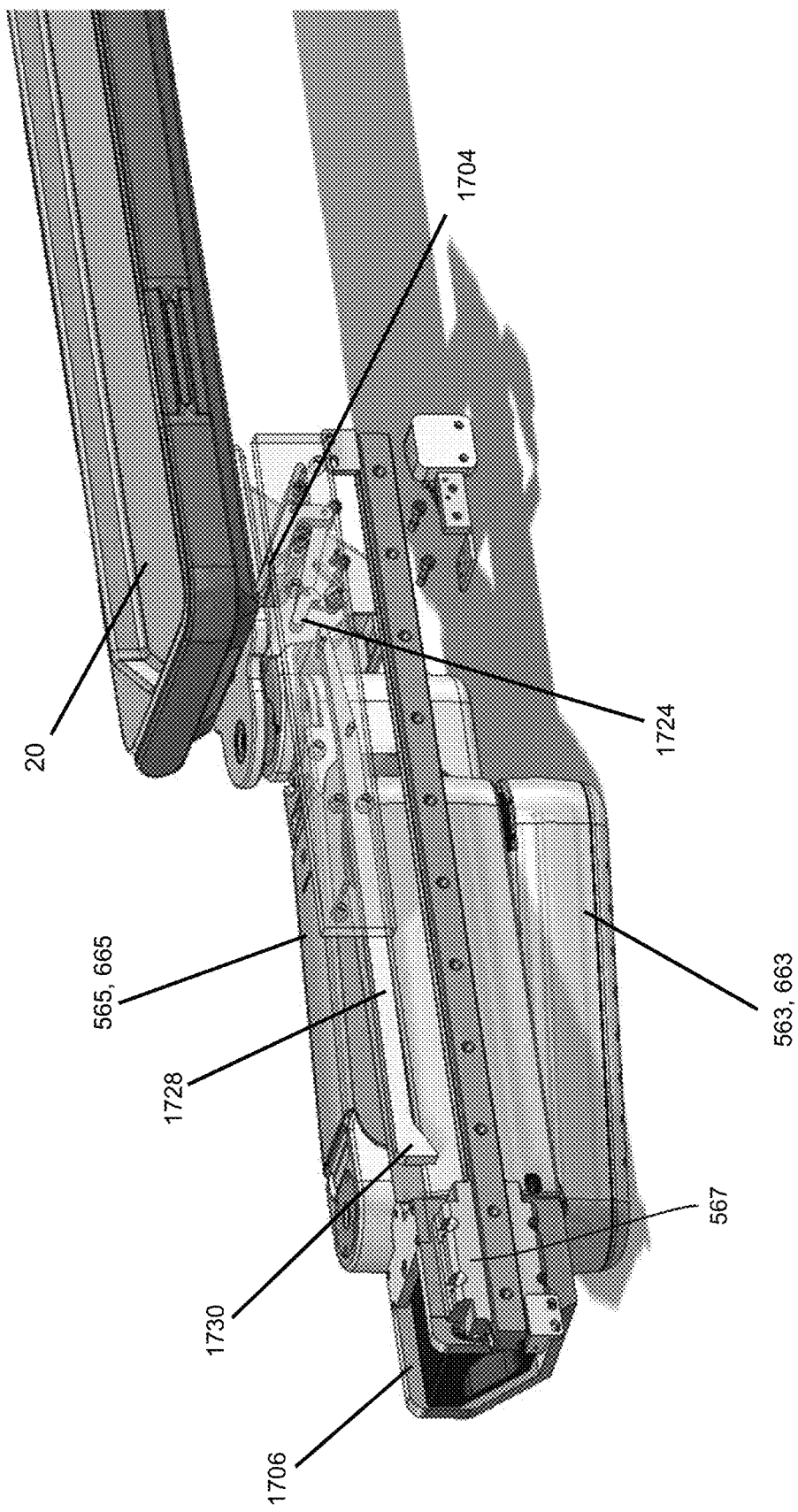
FIG. 26 shows a perspective reverse angle view of the configuration shown in FIG. 25.

FIG. 26 illustrates a reverse angle view of the arm 30 in a folded configuration, as compared to the view of FIG. 25. As Illustrated in FIG. 26, the medical device holder 20 is in a position to engage against the pivoting ramp 1704 to cause the finger 1724 to rotate upward and to cause the lock arm 1728 to rotate downward, causing detent 1730 to engage against the recess in the bearing block 567, as described elsewhere herein.

Drapes

To permit an arm in accordance with various embodiments of the present disclosure to be a reusable structure with sufficient stability, and optionally including sophisticated electronics and controls, extending from a base located in a nonsterile field to a sterile field, sterile draping over at least the arm can be used. Thus, it is envisioned that a sterile drape can have a sleeve-like configuration, which can be provided as an enclosed sleeve with an opening at one end to slide the sleeve over the arm. Alternatively, the sterile drape can be generally elongated and planar and configured to wrap around the arm and then be secured along its length to form the sleeve over the arm. In either case, a sterile drape can be secured over the arm, while having the medical device holder provided as a sterile component.

In an alternative embodiment, as has been discussed above, a sterile draping that covers both the arm and the medical device holder is contemplated. Such sterile draping would be useful so that medical device holders also can be reused without needing to be sterilized between each procedure and/or without needing to be made sterilizable (e.g., autoclavable). Moreover, a sterile drape in accordance with various embodiments can be used in conjunction with a medical device holder having an open frame member such that when the sterile drape is placed over the medical device holder it can form a well that can hold medical devices in a safe, secure, and convenient manner. Further, a sterile drape, whether extending along the arm only or both the arm and the medical device holder, can be provided with transmission line routing features to assist with routing and organization of transmission lines.

FIGS. 11A-13B show embodiments of sterile drapes configured to be placed over a three-link jointed arm and a medical device holder having a configuration as discussed with reference to the embodiment of FIG. 2A-1-2A-5. For example, the sterile drapes may be designed to cover the arm/medical device holder combination of FIGS. 10A-1-10B-3. FIGS. 11A-11D illustrate an embodiment of a sterile drape 1200, which receives the medical device holder 20 and at least a portion of arm 30 and thus provides a sterile environment all around the holder 20 and received portions of the arm 30. FIGS. 11E and 11F illustrate another embodiment of a sterile drape 1300, which is placed over the medical device holder 20 and the arm 30 without necessarily receiving the holder 20 and arm 30 within the drape 1300 or covering all sides of the holder 20 or arm 30.

Figure 11B:
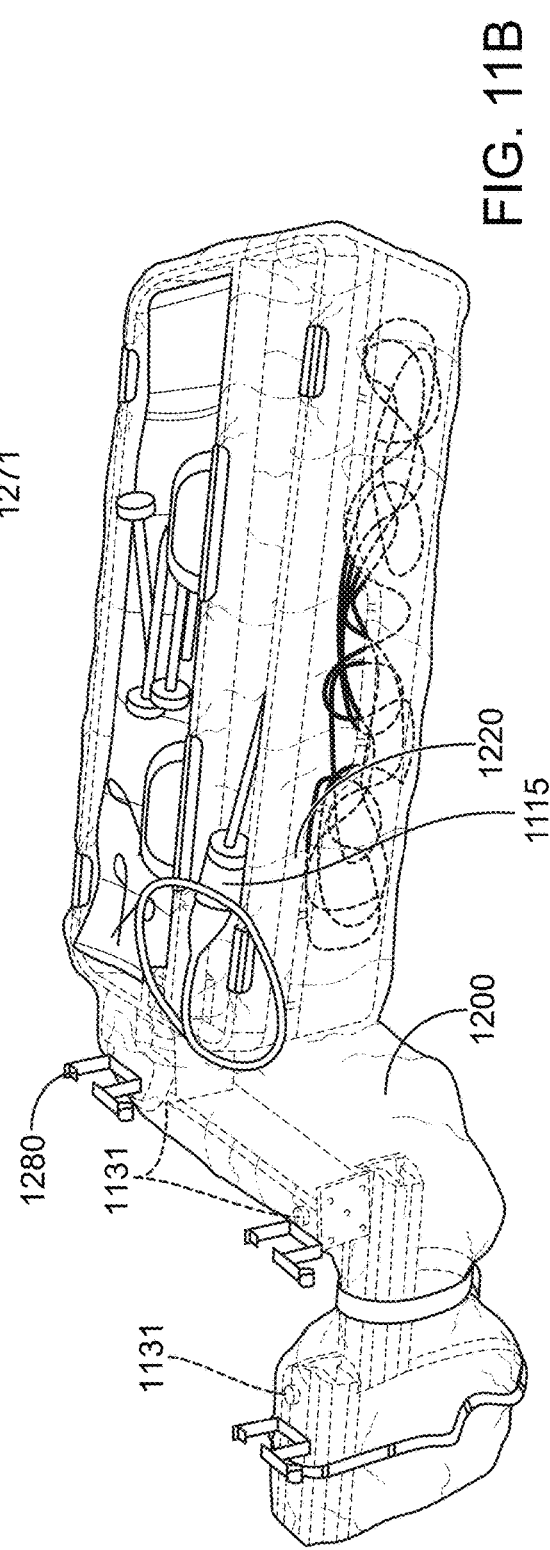
Figure 11C:
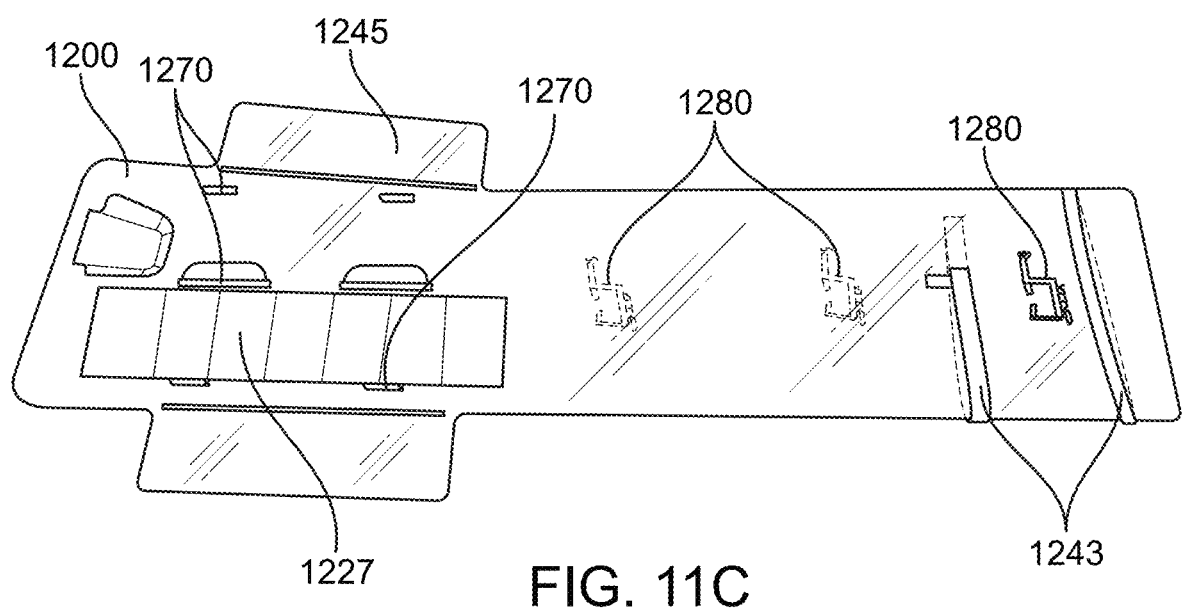
FIGS. 11C and 11D show perspective views of the drapes of FIGS. 11A and 11B when laid flat.
Figure 11D:
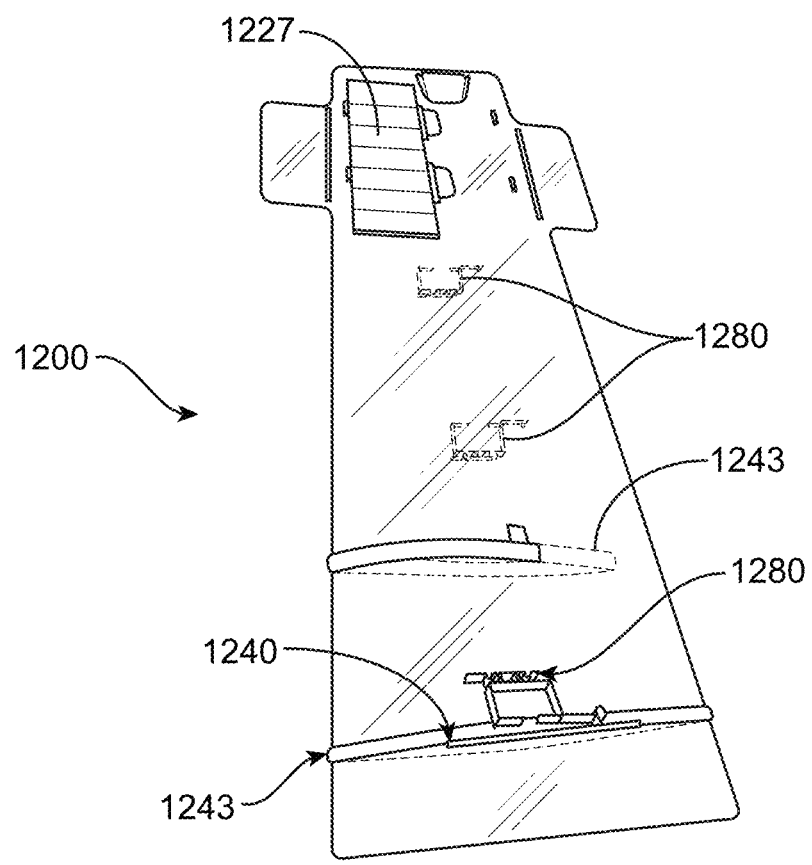

FIGS. 11A and 11B show two perspective views of an exemplary embodiment of a sterile drape 1200 in position over an arm 1130 and medical device holder 1120, which can have a configuration of the embodiments of FIGS. 2A-1-2A-5 and 10A-1-10B-3. FIGS. 11C and 11D show perspective views of the drape 1200 removed from the arm 1130 and medical device holder 1120. Drape 1200 is configured to provide a sterile environment entirely around medical device holder. Additionally, drape 1200 is configured to provide a sterile environment entirely around the arm from the distal end where it couples to the medical device holder and proximally to a position of at least a distal end portion of the first link member where the arm attaches to a base. This provides a large extension of the sterile field, thus providing greater workflow to a user during a medical procedure.

The drape 1200 has a configuration such that a portion 1220 of the sterile drape 1200 is received in the opening 1159 defined by a frame portion 1160 of the medical device holder 1120 to form a well/trough configured to receive and hold medical devices therein. As shown in FIG. 11B, in an exemplary application, the trough formed by placing the portion 1220 of the drape 1200 around the medical device holder 1120 provides a convenient storage area for an imaging instrument, such as an endoscope 1115. The portion 1225 of the drape 1200 that covers the tray portion 1150 of the medical device holder 1120 can be fitted over the tray portion and include an absorbent material layer 1227 on its outer surface that is placed over the support surface of the tray portion 1150. The absorbent material layer 1227 can be formed of, for example, cotton, and may be used to absorb any liquids, such as blood and other bodily fluids, that are retained on the medical instruments placed on the tray portion 1150 of the draped medical device holder 1120. In addition to absorbing fluids from medical devices, the absorbent material layer 1227 also may provide protection from a sharp end of a medical device damaging the sterile drape 1200. The absorbent material layer 1227 may be adhered to the portion 1225 of the drape using any well-known attachment means such as, for example, tape, adhesive, hook-and-loop-pile type fasteners (e.g., Velcro) or stitching (e.g., sewn together with the portion 1225 of the drape 1200). While the majority of the supporting surface of the tray portion 1150 of the medical device holder 1120 is covered with the absorbent material layer 1227 of the drape 1200 in the embodiment of FIGS. 11A and 11B, one of ordinary skill in the art would appreciate that the absorbent material layer 1227 can be of a variety of sizes and still fall within the scope of the disclosure. For example, the absorbent material layer 1227 may be placed only on one end or around the perimeter of the tray portion 1150 of the medical device holder 1120, or in any location that is more likely to receive soiled portions of medical devices. In an exemplary embodiment, a drape may include an absorbent material portion approximately 29 inches×7 inches, and a trough portion approximately 30 inches×6 inches×6 inches.

At least the portion 1220 of the drape 1200 that forms the trough and/or the portion 1225 that is disposed over the tray portion 1150 of the medical device holder can be made of a same or different material than a material of the portions of the drape covering the arm 1130. In an embodiment, the portions 1220, 1225 can be made of a thicker, more durable material (e.g., plastic) than other portions of the drape, to provide sufficient strength to hold the height of medical devices placed in the trough and to provide protection additional against puncture and tears. The material(s) of drape, in particular where the drape lies over the medical device holder 1120, can be so as to allow the drape 1200 to lie relatively flat and unwrinkled, in particular over the tray portion 1150 of the medical device holder 1120. In some embodiments, one or both portions 1220, 1225 are formed of a polyurethane (PU) film and the remaining portions of the drape 1200 are formed of low-density polyethylene. Additionally, the material of one or both portions 1220, 1225 can have a thickness that differs from remaining portions of the drape 1200. In one embodiment, one or both portions 1220, 1225 of the drape 1200 has a thickness of about 0.004 inches and other portions of the drape 1200 have a thickness of about 0.0012 inches. When laid flat, an embodiment of a drape 1200 is approximately 18 inches wide×32 inches long, not including any pockets, if provided.

Drape 1200 can have one or more features to help secure drape 1200 in place and the medical device holder 1120 and/or arm 1130. For example, as show in FIGS. 11A-11D, drape 1200 includes cuff tape 1240 to help cloak and wrap drape 1200 over medical device holder 20 and/or arm 30. Additionally, drape 1200 can include cinch tape 1243 along a length of drape 1200 where it covers the arm 1130. Once drape 1200 is initially disposed over, for example, arm 1130, drape 1200 may be bulky in certain areas. Cinch tape 1243 may be used to reduce this bulk so that drape 1200 can be made to more closely adhere to the shape and size of arm 1130. In various embodiments, drape 1200 also can include side pockets 1245 that are appended to one or more opposing lateral sides of the portion of the drape 1200 that covers the medical device holder 1120. These pockets 1245 can provide additional storage, and cuff tape 1240 can also be used to identify the location of pockets 1245.

To further assist retention of the drape 1200 in position over the medical device holder 1120, one or more clips can be used. As shown in FIGS. 11A and 11B, clips 1270 are U-shaped plastic members that snap over the drape 1200 to the frame portion 1160 and protruding lip surrounding the tray portion 1150. The clips 1270 can secure the drape 1200 in place and help to prevent ballooning of the drape 1200 when medical devices are placed in either the trough formed by portion 1220 or the on the tray portion 1150, thereby enhancing protection of medical devices against falling off the medical device holder 1120. Clips 1270 can be provided around the outer perimeter of the medical device holder 1120 as well as along a center separating the tray portion 1150 from the frame portion 1160. Clips 1270, when positioned in the center of the tray portion 1150, also prevent the tray portion of the drape 1200 from shifting or sliding when devices are inserted into the trough formed by portion 1220. The clips 1270 in the center can also be provided with vertically protruding guide ramps 1271 that can assist with guiding transmission lines up and over medical devices that may lie on the tray portion 1150 or in the trough formed by portion 1220, to provide an additional measure of protection from transmission lines accidentally engaging medical devices and causing unintended movement thereof.

As shown in FIG. 12B, a planform schematic view, and a perspective schematic view in FIG. 12A of the portions 1220 and 1225 of drape 1200 are shown, along with a detailed view of a clip 1270 (without the transmission line guide ramp) in FIG. 12C. While various exemplary embodiments contemplate the clips 1270 being provided as separate components, in an embodiment, the clips 1270 may be attached to the drape 1200 and come as part of the drape structure, as shown for example, in the embodiment shown in FIGS. 11C and 11D, which show perspective views of the drape 1200 removed from the arm 1130 and medical device holder 1120 in FIGS. 11A and 11B. Clips 1270 can be formed of, for example, injection molded acrylonitrile butadiene styrene (ABS). Clips 1270 can include protrusions 1273 (only one being shown) on an internal surface of the leg members forming the U-shape to provide a snap-fit retention with the lip surrounding the tray portion and frame member of the medical device holder.

Figure 13A:
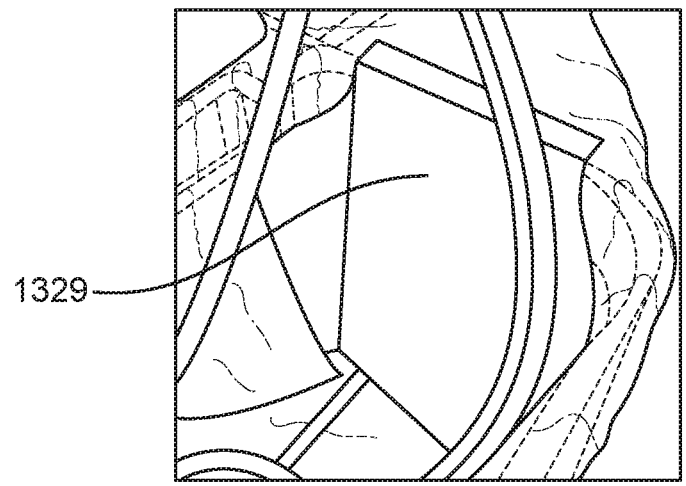
FIGS. 13A and 13B show perspective views of and exemplary embodiment of an end cap in accordance with the present disclosure.
Figure 13B:
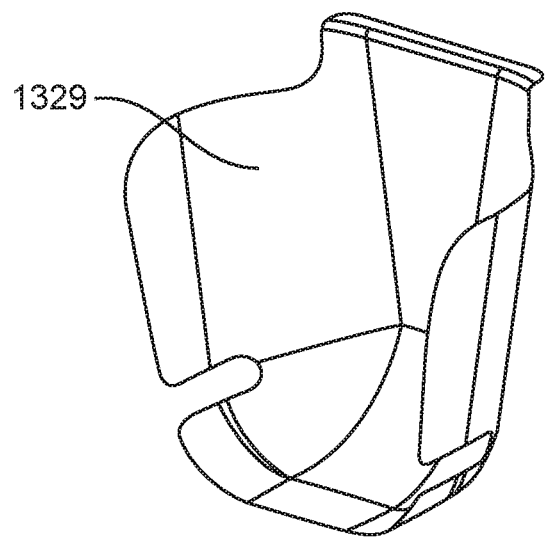

In another embodiment, an end cap can be fit within the drape to better form the trough part of the drape and to further increase resistance to puncture. Reference is made to FIGS. 13A and 13B, which show an end cap 1329 in isolation (FIG. 13B) and fitted within the trough portion of a drape in position over an end of the frame member of a medical device holder (FIG. 13A). A similar trough end cap 1329 can optionally be provided at an opposite end of the medical device holder and trough. As shown, trough end cap 1329 can include a relatively thicker plastic or paperboard material, such as, for example, low-density polyethylene (LDPE) or coated paperboard that can be snap-fit over the end of the trough and medical device holder frame. In some embodiments, as shown in FIGS. 13A and 13B, trough end caps 1329 may be a separate member that is snap fitted onto medical device holder 1120 over drape 1200. Trough end caps 1329 may be configured to prevent drape 1200 from being punctured by the tip of a medical instrument when the instrument is disposed (or is in the process of being disposed) within the trough formed by portion 1220 of the drape 1200, and also provide a smooth surface over which to run various transmission lines (as illustrated in FIG. 13A).

Drapes 1200 and 1300 also can include (or be used in conjunction with) cable guides 1280 which comprise transmission line routing features, such as one or more clips and/or guideposts to receive and route transmission lines from medical devices supported on the medical device holder to equipment outside of the sterile field. In an embodiment, the cable guides 1280 also can help secure the drape 1200, 1300 to the arm 1130. The cable guides 1280 can be provided at joints 1131 of the arm 1130 and can be permitted to swivel to allow for slack in and prevent pulling of transmission lines as the arm 1130 and/or medical device holder 1120 are moved. Additionally, the cable guides 1280 can minimize any shifting or moving of drape 1200, 1300 when items are placed in the trough portion.

Figure 14C:
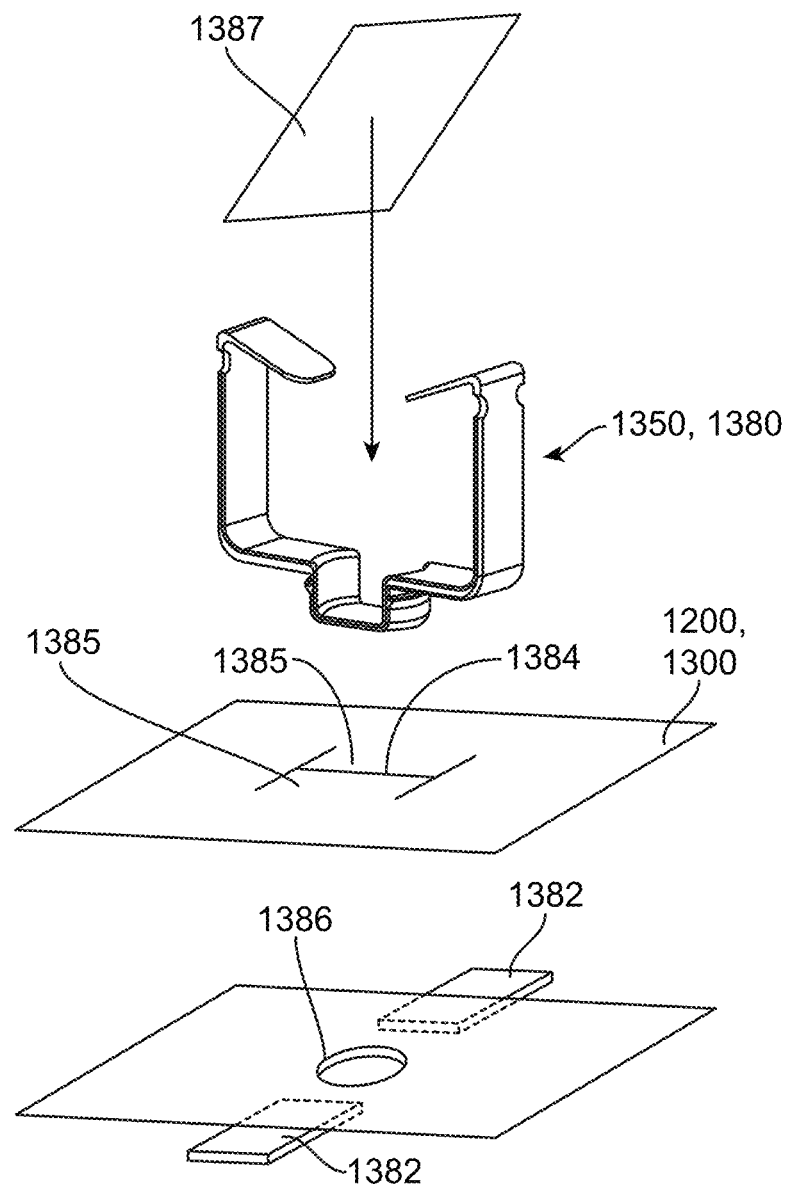
FIG. 14C shows an exploded view of an exemplary embodiment of attaching a cable guide to a drape in accordance with the present disclosure.
Figure 14D:
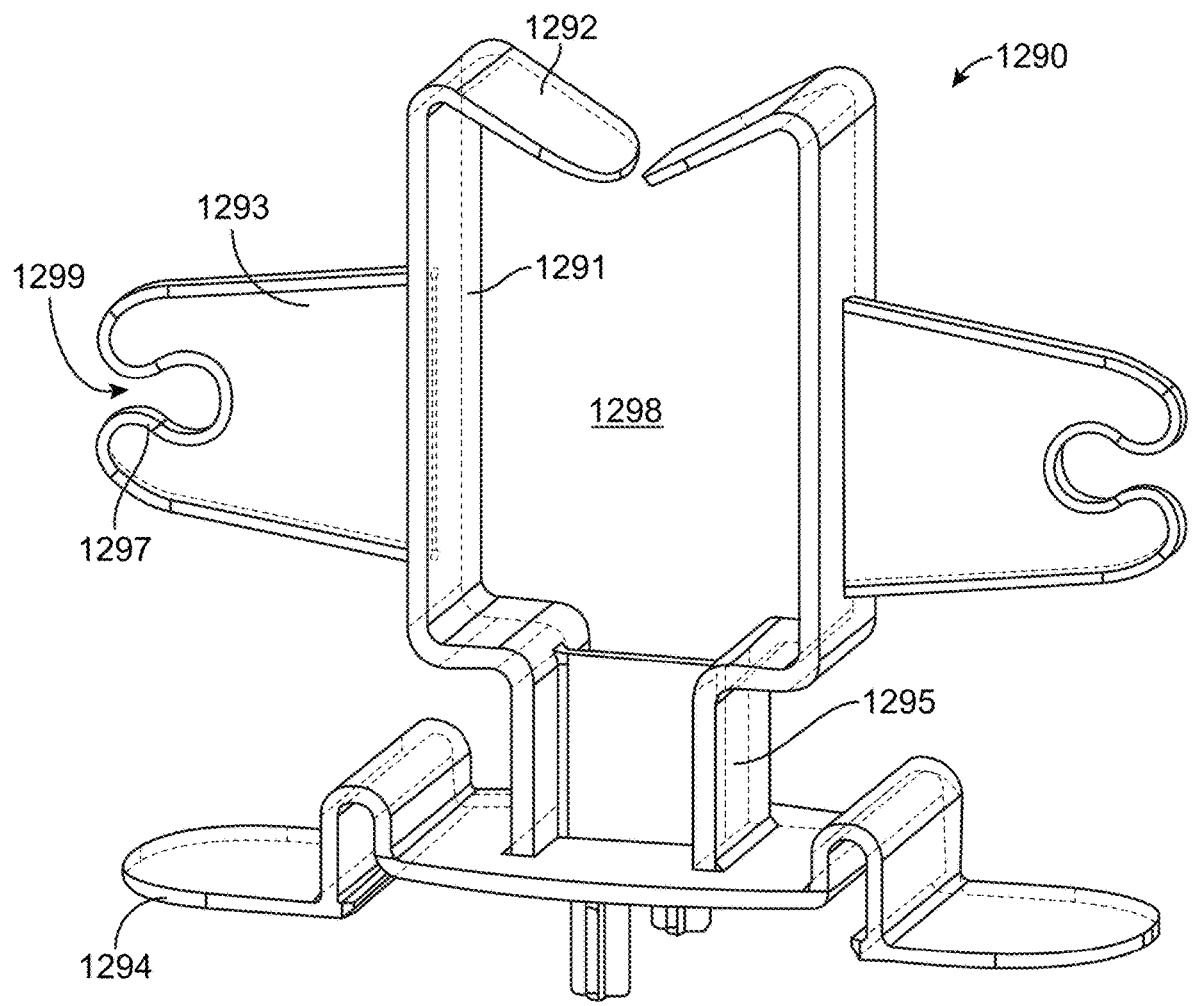
FIG. 14D shows perspective view of yet another embodiment of a cable guide in accordance with the present disclosure.

Reference is made to FIGS. 11A-11F for various views of examples of how the cable guides 1280 can be used in relation to drapes 1200, 1300 and/or arm 30. The detailed view of FIG. 11E shows transmission lines TL routed through the routing features of the cable guides 1280. As shown in the FIGS. 11A-11F, cable guides 1280 can be secured along a length of the drape 1200, 1300 that covers the arm 30 to organize and direct transmission lines. Generally, embodiments of the cable guides 1280, as shown in FIGS. 11A-11F and 14A-1-14D, have a U-shaped central portion formed by guidepost arms, which define an opening to receive and route transmission lines. Some embodiments of the cable guides 1280, as shown in in FIGS. 11A-11F and 14D, also include one or more side arms extending laterally from the guidepost arms to define an additional opening to receive and route an additional transmission line. In other embodiments of the cable guides 1280, as shown in FIGS. 14A-1-14C, such side arms are omitted. Specific embodiments of the cable guides 1280 are illustrated in FIGS. 14A-1-14D and are described in greater detail below.

FIG. 14D illustrates an embodiment of a cable guide 1290, which can be used as the cable guides 1280. In one embodiment, as shown in FIG. 14D, the cable guide 1290 comprises guidepost arms 1291 that extend in one direction and side arms 1293 that extend laterally from the guidepost arms 1291 in another direction, on one or both sides. The side arms 1293 comprise clips 1297, for example at an end of the side arms 1293, that are intended to receive transmission lines associated with a monopolar or a bipolar electrosurgical instrument. Separating such transmission lines can help to avoid capacitive coupling between the lines if they were located too close together. It may be sufficient to have only one side arm 1293 and route one of the bipolar or monopolar electrical transmission line through the side arm 1293 and the other through the main opening 1298 of the cable guide 1290.

As mentioned above, the cable guide 1290 with side arms 1293 can be configured to be attached to the drape 1200 and through the drape 1200, 1300 to the arm 1130. FIG. 14D shows an exemplary structure of a cable guide 1290 with side arms 1293 for attachment to a drape 1200 and for subsequent attachment of the drape 1200, 1300 to an arm 1130. The cable guide 1290 includes opposing guidepost arms 1291 that define boundaries of an opening 1298 between the guidepost arms 1291 to receive and route a bundle of transmission lines (not illustrated). Retention elements 1292 extend from top portions of the guidepost arms 1291 and further define boundaries of the opening 1298. The retention elements 1292 are oriented and slanted toward each other to provide a barrier for transmission lines, which helps to retain transmission lines within the opening 1298 formed between the guidepost arms 1291. Bottom portions of the guidepost arms 1291 are coupled to a base portion 1295. In this embodiment, the cable guide 1290 further includes a separate base 1294 that can be disposed on the inside of drape 1200, 1300. The upper portion of the cable guide 1290 that is outside the drape 1200 (e.g., base portion 1295) can fasten through the drape 1200, 1300 to the base 1294. Such fastening can occur via a mechanical connection or via magnetic connection. The guidepost arms 1291 can be flexible, e.g., are formed of a flexible material, such as a flexible plastic, e.g., ABS, and may bend in order to accommodate a large number of transmission lines and to allow a user to easily place them within the opening.

In some embodiments, the side arms 1293 can extend laterally outward from one or both of the guidepost arms 1291, and can comprise clips 1297 that define openings 1299 that can receive, separate, and route transmission lines, such as, for example bipolar or monopolar electrical energy transmission lines as discussed above.

FIGS. 14A-1-14C depict other structural arrangements and features of embodiments of the cable guides 1280 in accordance with the present disclosure. FIGS. 14A-1 and 14A-2 show perspective and top plan views, respectively, of a cable guide 1350 according to yet another embodiment, which can be used as the cable guides 1280. With reference to FIG. 14A-1, a cable guide 1350 includes a pair of upwardly extending guidepost arms 1352 and slanted retention elements 1392 extending from the guidepost arms 1352, which together define at least some boundaries of an opening 1356 between them. The pair of upwardly extending guidepost arms 1352 are integral with the retention elements 1392 and extend up from a pair of latterly extending members 1354. Together, the retention elements 1392, the guidepost arms 1352, and the members 1354 define the opening 1356 to accommodate transmission lines. The members 1354 extend laterally from a cylindrical or semi-cylindrical boss 1358 (also referred to herein as a base portion) which has an optionally hollow interior. One or more ramped, snap fit features 1360 are formed on an exterior surface of the boss 1358. The boss 1358 is sized to cooperate with a receptacle 1364 formed in a portion 1362 of the arm 30 and/or the holder 20. The receptacle 1364 defines an opening or hole 1365 into which the boss 1358 may be received. The portion 1362 includes a ramp 1366 which is sized to cooperate with the snap fit feature 1360 on the boss 1358 so that the boss 1358 can be forced into the receptacle 1364 and held therein by the snap fit features 1360 and ramps 1366, while still permitting the boss 1358 to swivel within the receptacle 1364 (and hence permitting the cable guide 1350 to swivel relative to the arm 30). While the boss 1358 is being forced into the receptacle 1364, the snap fit feature 1360 and/or ramps 1366 flex as the snap fit feature 1360 passes over the ramps 1366, and then once the snap fit feature 1360 has passed the ramps 1366, the snap fit feature 1360 and/or ramps 1366 snap back into place to hold the boss 1358 within the receptacle 1364.

FIGS. 14B-1 to 14B-3 illustrate another exemplary embodiment of a cable guide 1380, which may be used as the cable guide 1280. The cable guide 1380 is similar in some respects to cable guide 1350 and common reference numerals have been used to designate similar or the same features. Cable guide 1380 includes a rib structure 1370 on the interior surface of one or both of the guidepost arms 1352. The rib structure 1370 helps to provide rigidity to the guidepost arms 1352 and to inhibit transmission lines from snagging on the arms 1352. In addition, a snap fit feature 1372 is provided on an exterior surface of boss 1358. The snap fit feature 1372 may also be formed as a ribbed structure similar to that of rib structure 1370. Similarly, snap fit feature 1372 is more rigid than the snap fit feature 1360 of cable guide 1350, but it performs the same general function of permitting the cable guide 1380 to be snapped into a receptacle in a portion of the arm 30, such as portion 1362, and permit the cable guide 1380 to swivel relative to that portion.

FIG. 14-C illustrates another exemplary embodiment of attaching cable guide 1280 as described herein to a drape 1200, 1300. As illustrated in FIG. 14C, a hole 1384, which may be formed by three slits arranged in the shape of an H, is made in the drape 1200, 1300 at a location that is (or will be) positioned over a receptacle 1386. The receptacle 1364 in the portion 1362 of the arm 30 or holder 20 may be used as the receptacle 1386. The drape 1200, 1300 comprises two opposing flaps 1385 at the hole 1384, which may be formed as a result of making the slits. The opposing flaps 1285 at least partially bound and define the hole 1384. A cable guide 1350, 1380 is then inserted through the hole 1384 into the receptacle 1386), displacing the opposing flaps 1385 into the receptacle 1386 as a result. A pair of fingers 1382 (also referred to herein as hole-closing members) adjacent to the receptacle 1385 are then pushed towards the receptacle 1386, which raises the flaps 1385 to be coplanar with the rest of the material of the drape 1200 and thus to at least partially cover the boss 1358. Lastly, a piece of tape 1387 or the like (also referred to herein as a sealing member) is then placed into the interior of the boss 1358 of the cable guide 1350, 1380 from above and secured to the drape 1200, 1300, thus capturing the cable guide 1350, 1358 in place and sealing the hole 1384.

The cable guides 1280 and other transmission line routing features described herein may be integral components with a drape (e.g., drape 40 or 1200), and they may be packaged together with a drape. Alternatively, they can be provided as separate components and attached to the drape when ready for use.

Figure 11F:
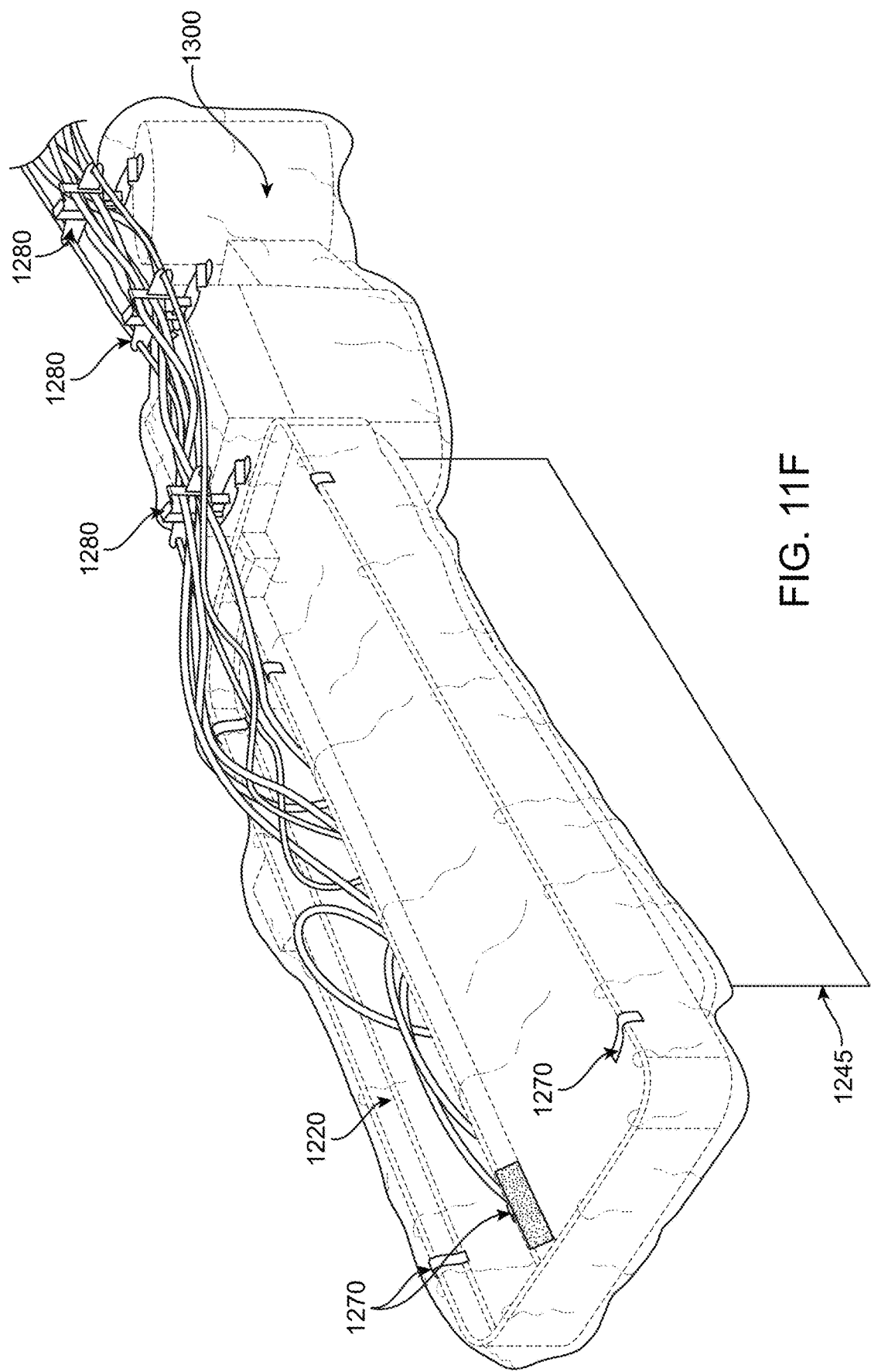

FIGS. 11E and 11F provides another perspective view of a drape 1300 having many of the features as drape 1200 described above, placed over a medical device holder and arm in accordance with an exemplary embodiment of the present disclosure. As shown in FIGS. 11E and 11F, the drape 1300 may be used in conjunction with cable guides 1280, clips 1270, and/or cinch tape 1243, as described above. As shown in FIG. 11F, the drape 1300 may also have a portion 1220 forming a trough and/or side pockets 1245, as described above.

In some embodiments, it is contemplated that separate drapes are provided over the medical device holder and the arm respectively. Thus, the size and shape of a first drape may be tailored for medical device holder 1120, and the size and shape of a second drape may be tailored for arm 1130. Various other features as described above may still be provided as the respective first and second drapes.

Base

As discussed above, base 10 may be any of a variety of structures. In an exemplary embodiment, the base 10 is an auxiliary system cart that includes equipment for supplying and controlling various auxiliary surgical functions, such as, for example, image processing, electrocautery energy generation, system central processing, and/or insufflation/suction. In other embodiments, base 10 may be any cart or fixed base sufficient to provide a stable support structure for an arm and medical device holder in accordance with various exemplary embodiments described herein. It is also contemplated that base 10 may be a patient's operating table or another telesurgical system component, such as a manipulator system or a master control unit (e.g., surgeon console). By way of a non-limiting example, one such base is 26 inches wide×27 inches deep×60 inches high.

Figure 15A:
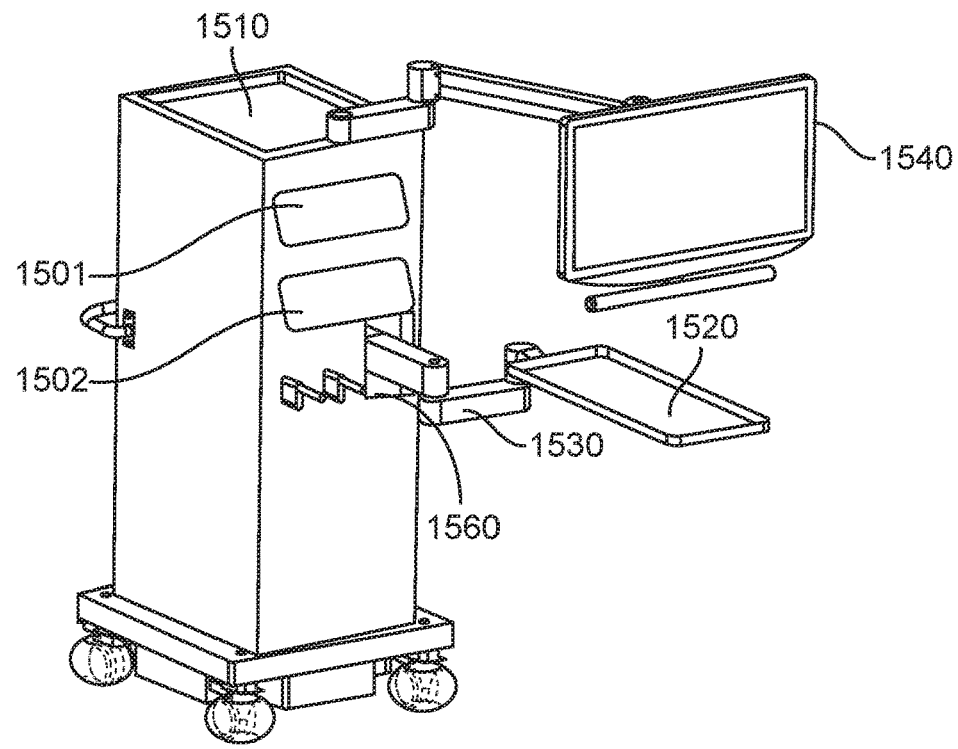
FIGS. 15A and 15B show perspective views of various exemplary embodiments of a combination of a base, arm, holder, and drape in accordance with the present disclosure
Figure 15B:
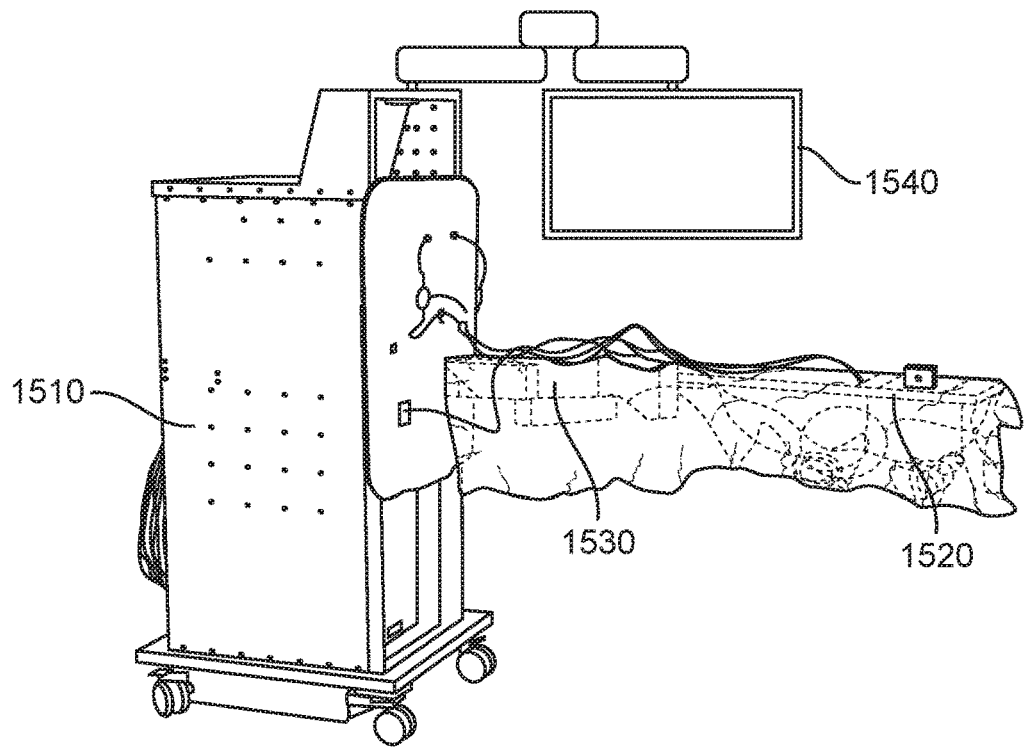

As shown in FIGS. 15A and 15B, the base to which an arm 1530 and medical device holder 1520 attach can be a wheeled auxiliary system cart 1510 (also referred to as base 1510) that holds one or more auxiliary function equipment 1501, 1502 (two such equipment components being depicted) and provides control functionality of a telesurgical system. Examples of such auxiliary function equipment include, but are not limited to endoscopic illumination and control units, electrosurgical energy generators, insufflation devices, robot system control and processing equipment, specialty instruments control units, saline and fluid dispensing. and suction units. The auxiliary system cart 1510 may be used as the base 10, the arm 1530 may be one of the embodiments of the arm 30 described herein, and the medical device holder 1520 may be one of the embodiments of the medical device holder 20 described herein. In an exemplary embodiment, the arm 1530, alone or with the medical device holder 1520 attached, can fold and retract into a cavity 1560 provided in the auxiliary system cart 1510, in a manner similar to that described above with regard to the exemplary embodiments of FIGS. 6A-6E. In an embodiment, the cavity 1560 may be Approximately 8 inches tall×9 inches wide×24 inches deep. Although not shown, connector ports, to receive the connectors on the transmission lines of medical devices, can be part of the auxiliary function equipment 1501, 1502 in order to connect medical devices on the medical device holder to the auxiliary function equipment 1501, 1502.

The base 1510 also includes one or more monitors and/or screens 1540 in order to show various functions and parameters associated with the patient, for example, oxygen concentration and heart rate, and also to show images of a remote surgical site being captured by an image capture device during the surgical procedure.

Base 1510 may remain outside of the sterile field. But, providing draping on the arm 1530 and the medical device holder 1520, or otherwise, provides a sterile medical device holder 1520 that allows medical devices supported by the medical device holder to be safely connected to the auxiliary equipment of the base 1510 without compromising the sterile field.

Figure 15C:
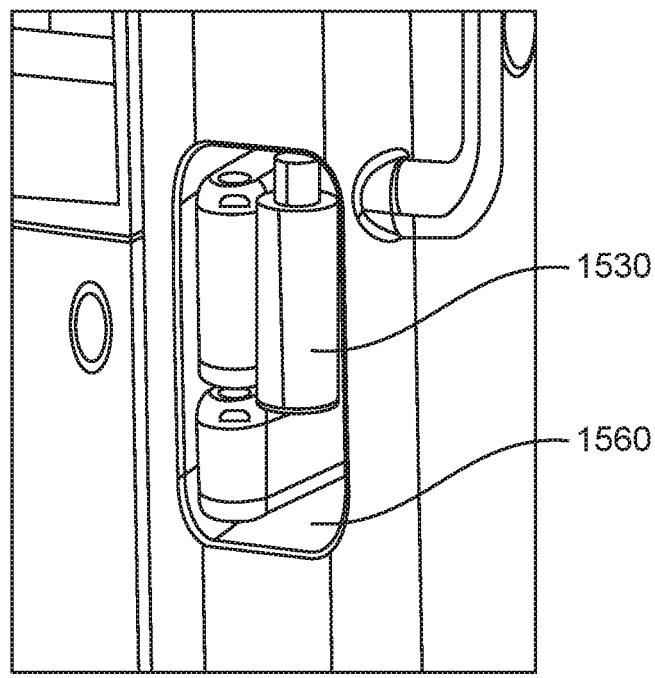
FIGS. 15C and 15D show detailed views of portion of the base of FIG. 15A or 15B.
Figure 15D:
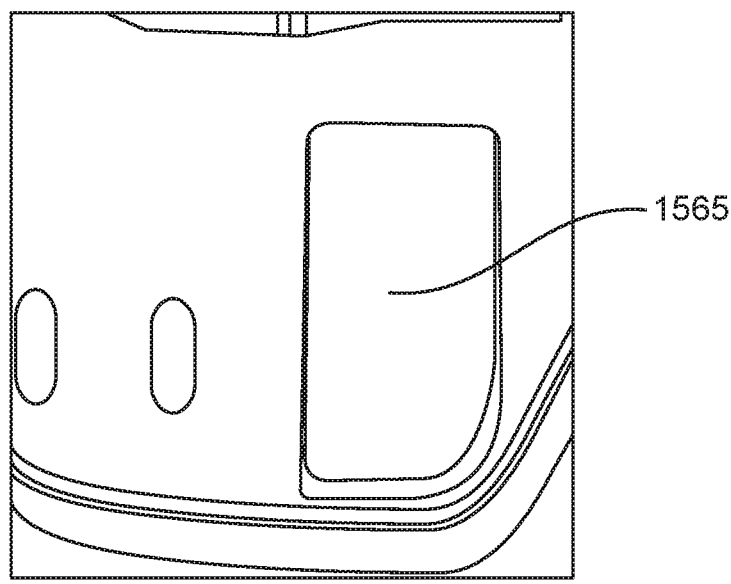

FIGS. 15A and 15B show medical device holder 1520 and arm 1530 in the extended configuration such that these members are disposed outward of cavity 1560. FIG. 15C shows medical device holder 1520 and arm 1530 in the retracted configuration such that these members are disposed within cavity 1560. As shown in FIG. 15D, cavity 1560 may be enclosed with a door 1565 to protect medical device holder 1520 and arm 1530 when they are stored within cavity 1560. The door 1565 may be manually opened and closed, or may be automated. Base 1510 is wide and heavy enough to prevent instability or overbalance due to typical loads applied to the arm or holder. Energy for the medical devices may be provided via electrically conductive cables (not illustrated) from any of the auxiliary or integrated devices described herein.

Figure 16A:
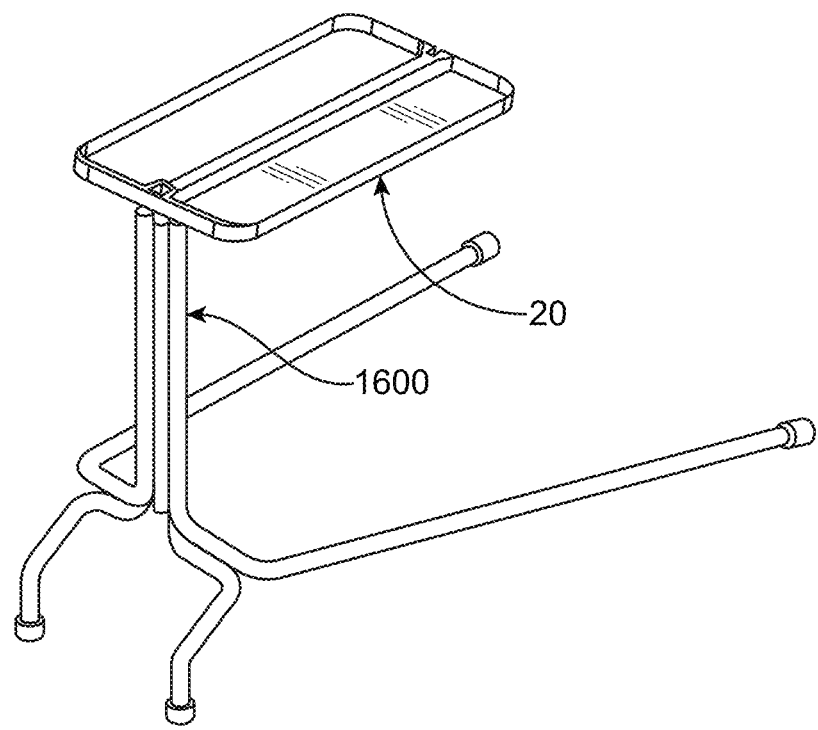
FIGS. 16A-16B show perspective views of exemplary embodiments of a medical device holder and an arm used with a stand.
Figure 16B:
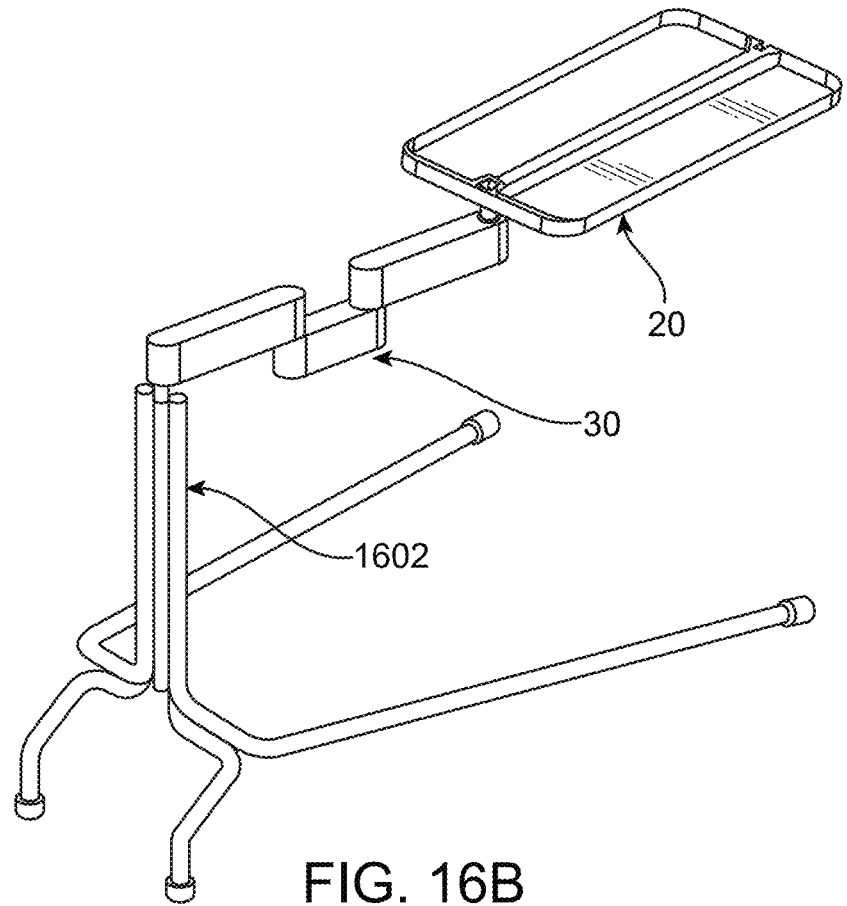

FIGS. 16A-16B show perspective views of exemplary embodiments of a tray and an arm used with a stand. Any of the embodiments described herein may be used with a conventional Mayo stand-type base, as generally illustrated in FIGS. 16A-B. FIG. 16A illustrates an exemplary medical device holder 20 used with, or mounted to, a stand 1600. FIG. 16B illustrates an exemplary arm 30 used with, or mounted to, a stand 1602.

Overall System

In various exemplary embodiments, an arm that provides a mechanical supporting link between a base and a medical device holder, such as, for example, a tray, receptacle, surface, or any combination thereof, may provide a stable structure that facilitates workflow by allowing sterilized medical devices to be connected, routed, and set up prior to and during surgery, The various exemplary embodiments may be used in any combination in a medical procedure in order to provide convenient and easy access to a sterile environment. A user may easily manipulate the location of each of the disclosed components to quickly and efficiently rearrange the layout of the sterile environment. Such may be useful if a user wants to access the surgical site from another angle, or if the user needs to quickly access the surgical site. Additionally, the easy manipulation of the system speeds up the process between pre-op and intra-op. For example, the various exemplary embodiments allow sterilized devices to be easily attached, routed, and staged prior to surgery. The various exemplary embodiments also provide superior cable management and storage compared with conventional systems. Furthermore, as discussed above, the various exemplary embodiments provide for easy and secure storage of an arm and a medical device holder within an outer base.

As discussed above, the features discussed herein provide instrument and cable storage and organization. Thus, the features discussed herein provide an improved workflow system.

Further modifications and alternative embodiments will be apparent to those of ordinary skill in the art in view of the disclosure herein. For example, the systems and the methods may include additional components or steps that were omitted from the diagrams and description for clarity of operation. Accordingly, this description is to be construed as illustrative only and is for the purpose of teaching those skilled in the art the general manner of carrying out the present teachings. It is to be understood that the various embodiments shown and described herein are to be taken as exemplary. Elements and materials, and arrangements of those elements and materials, may be substituted for those illustrated and described herein, parts and processes may be reversed, and certain features of the present teachings may be utilized independently, all as would be apparent to one skilled in the art after having the benefit of the description herein. Changes may be made in the elements described herein without departing from the spirit and scope of the present teachings and following claims.

It is to be understood that the particular examples and embodiments set forth herein are nonlimiting, and modifications to structure, dimensions, materials, and methodologies may be made without departing from the scope of the present teachings. For example, various aspects have been described in the context of an instrument used in a surgical robotic system. But these aspects may be incorporated into hand-held instruments as well.

Other embodiments in accordance with the present disclosure will be apparent to those skilled in the art from consideration of the specification, and practice of the teachings disclosed herein. It is intended that the specification and examples be considered as exemplary only, with a true scope and spirit being indicated by the following claims.

What is claimed is:

1. A sterile drape assembly comprising:
   a drape comprising:
      a first portion configured to cover a medical device holder; and
      a second portion configured to cover a portion of an arm that supports the medical device holder; and
   a cable guide coupled or configured to be coupled to the drape, the cable guide comprising:
      two opposing guidepost arms extending in a first direction and defining a first opening; and
      a side arm extending laterally from one of the guidepost arms, the side arm defining a second opening;
      wherein the first opening is configured to receive and route a first transmission line along a first path; and
      wherein the second opening is spaced from the first opening and is configured to receive and route a second transmission line along a second path spaced from the first path.

2. The sterile drape assembly of claim 1, wherein the side arm comprises a clip portion defining the second opening and configured to retain the second transmission line received in the second opening.

3. The sterile drape assembly of claim 1, wherein:
   the side arm extends in a second direction from a first one of the guidepost arms, and
   the cable guide comprises a second side arm extending laterally from a second one of the guidepost arms in a third direction opposite from the second direction, the second side arm defining a third opening configured to receive and route a third transmission line along a third path spaced from the first path and the second path.

4. The sterile drape assembly of claim 1, wherein the cable guide comprises a retention member extending from one of the guidepost arms and configured to retain the first transmission line positioned in the first opening.

5. The sterile drape assembly of claim 1, wherein:
   the cable guide comprises an interior base portion configured to be positioned on an interior of the drape and an exterior base portion configured to be positioned on an exterior of the drape;
   the guidepost arms are coupled together via the exterior base portion; and
   the interior base portion is attachable to the exterior base portion through the drape.

6. The sterile drape assembly of claim 5, wherein the interior base portion is mechanically attachable to the exterior base portion.

7. The sterile drape assembly of claim 6, wherein the interior base portion is magnetically attachable to the exterior base portion.

8. The sterile drape assembly of claim 1, wherein the cable guide comprises a base portion configured to be insertable through an opening in the drape into a complementary receptacle in the arm to attach the cable guide to the arm.

9. The sterile drape assembly of claim 8, wherein the base portion comprises a snap fit retention feature configured to rotatably couple the base portion to the complementary receptacle in the arm.

10. The sterile drape assembly of claim 8, wherein:
    the guidepost arms are on a side of the drape opposite to where the base portion is located to be insertable into the complementary receptacle in the arm.

11. The sterile drape assembly of claim 1, wherein the first portion of the drape defines a trough configured to receive a medical device.

12. The sterile drape assembly of claim 11, further comprising an end cap positioned within the trough, the end cap configured to maintain a contour of the trough.

13. The sterile drape assembly of claim 1, wherein the first portion of the drape is formed of a different material than the second portion of the drape.

14. The sterile drape assembly of claim 1, wherein the first portion of the drape has a different thickness than the second portion of the drape.

15. The sterile drape assembly of claim 1, wherein the first portion of the drape comprises a drape material to form a sterile barrier and absorbent material attached to an exterior surface of the drape material.

16. The sterile drape assembly of claim 1, wherein the drape has a closed end, an open end, and side wall portions extending between the open end and the closed end to define an interior space configured to receive the medical device holder and at least the portion of the arm.

17. The sterile drape assembly of claim 1, further comprising at least one pocket formed in the second portion of the drape on an exterior surface of the drape.

18. The sterile drape assembly of claim 1, wherein the first opening is configured to receive and route a plurality of transmission lines including the first transmission line.

19. The sterile drape assembly of claim 1, wherein, in a coupled state of the cable guide to the drape, the guidepost arms extend away from a surface of the drape with each guidepost arm terminating in a free end.

* * * * *